United States Patent
Gu

(10) Patent No.: US 7,358,335 B2
(45) Date of Patent: Apr. 15, 2008

(54) ARF-BP1 AS MEDIATOR OF P53-DEPENDENT AND INDEPENDENT TUMOR SUPPRESSION AND USES THEREOF

(75) Inventor: Wei Gu, Paramus, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/118,524

(22) Filed: Apr. 29, 2005

(65) Prior Publication Data

US 2006/0088847 A1    Apr. 27, 2006

Related U.S. Application Data

(60) Provisional application No. 60/610,506, filed on Sep. 15, 2004.

(51) Int. Cl.
*C07K 5/10* (2006.01)
*G01N 33/53* (2006.01)

(52) U.S. Cl. ....................... 530/350; 435/7.1
(58) Field of Classification Search .................. None
See application file for complete search history.

(56) References Cited

FOREIGN PATENT DOCUMENTS

WO     WO-03/063688 A2    8/2003

OTHER PUBLICATIONS

Beers and Berkow (eds.), The Merck Manual of Diagnosis and Therapy, 17th ed. (Whitehouse Station, N.J.: Merck Research Laboratories, 1999) 973-74, 976, 986, 988, 991.
Bertwistle, D, Sugimoto, M. Sherr, C.J., *Mol Cell* Biol 24:985-96, 2004.
Buchberger, A., *Trends in Cell Biol.* 12:216-221, 2002.
Chresta and Hickman, *Nature Medicine* 2:745-6, 1996.
Dornan, D., Wertz, L, Shimizu, H., Arnott, D., Frantz, G.D., Dowd, P., O'Rourke, K., Koeppen, H., Dixit, V.M., *Nature* 429:86-92, 2004.
Elbashir, S.M. et al., *Nature* 411:494-498, 2001.
Gu, J., Ren, K., Dubner, R., and Iadarola, M.J., *Brain Res Mol Brain Res.* 24:77-88, 1994.
Gu, W., Malik, S., Ito, M. Yuan, C.X., Fondeil, J.D., Zhang, X., Martinez, E., Qin, J., Roeder, R.G., *Mol Cell* 3:97-108, 1999.
Haupt et al., *Nature* 387:296-299, 1997.
Hicke, L., and Dunn. R., *Annu Rev Cell Dev Biol* 19:141-172, 2003.
Hollstein et al., *Mutat Res.* 431:199-209, 1999.
Honda, R., Tanaka, H., Yasuda, H., *FEBS Lett* 420:25-27, 1997.
Itahana, K et al., *Mol Cell* 12:1151-64, 2003.
Kamijo, T., et al., *Cell* 91:649-659, 1997.
Kelly-Sprat, K.S., Gurley, K.E., Yasui, Y., Kemp, C.J., *PloS Biol.* 2:E242, 2004.
Kubbutat, M.H., Jones, S.N., Vousden, K.H., *Nature* 387:299-303, 1997.
Kuo et al., *Genes Dev.* 18:1862, 2004.
Lane and Fisher, *Nature* 427:789-90, 2004.
Leng, R.P., Lin, Y., Ma, W., et al., *Cell* 112:779-91, 2003.
Levine, A.J., *Cell* 88:323-31, 1997.
Li, M., Brooks, C.L., Wu-Baer, F., Chen. D., Baer, R., Gu, W., *Science* 302:1972-1975, 2003.
Luo, J., Su, P., Chen, D., Shiloh, A., Gu. W., *Nature* 408:377-81, 2000.
Luo, J. et al., *Cell* 107:137-48, 2001.
Lutzker and Levine, *Cancer Treat Rep*, 87:345-56, 1996.
Michael, D., and Oren, M., *Semin Cancer Biol* 13:49-58, 2003.
Montes De Oca Luna, R., Wagner, D.S., Lozano, G., *Nature* 378:203-206, 1995.
Munger, K., Howley, P.M., *Virus Res* 89:213-228, 2002.
Nikolaev, A.Y., Li, M., Puskas, N., Qin, J., Gu, W., *Cell* 11:29-40, 2003.
Nilsson, J.A. Cleveland, J.L. *Oncogene* 22:9007-21, 2003.
Normand, G., Hemmati, P.G., Verdoodt, B. et al., *J. Biol Chem* 280:7118-30, 2005.
Oren, M., *J. Biol. Chem.* 274:36031-034, 1999.
Rocha, S., Campbell, K.J., Perkins, N.D., *Mol Cell*, 12:15-25, 2003.
Sharpless, N.E., DePinho, R.A., *J. Clin Invest* 113:160-8, 2004.
Sherr, C.J., *Nat Rev Mol Cell Biol* 2:731-737, 2001.
Surendran, A., *Nature Medicine*, 10:9, 2004.
Vassilev L. T. et al., *Science* 303:844-8, 2004.
Vogelstein et al., *Nature* 408:307-310, 2000.
Weber, J.D., et al., *Genes Dev.* 14:2358-65, 2000.
Xirodimas, D.P., Stephen, C.W., Lane, D.P., *Oncogene* 20:4972-83, 2001.
Yarbrough, W.G. et al., *Cancer Res* 62:1171-7, 2002.
Zhang, Y., Xiong, Y., Yarborough, W.G., *Cell* 92:725-34, 1998.
Yoon et al.; Over-expression of Human UREB1 in Colorectal Cancer: HECT domain of human UREB1 inhibits the activity of Tumor Suppression p53 Protein, Biochem Biophys Res Comm, Nov. 2004, 326: 7-17.
Gu et al., "UREB1, a tyrosine phosphorylated nuclear protein inhibits p53 transactivation." Oncogene, 1995, 11:2175-2178.

(Continued)

Primary Examiner—Misook Yu
Assistant Examiner—Mark Halvorson
(74) *Attorney, Agent, or Firm*—Wilmer Cutler Pickering Hale and Dorr LLP

(57) ABSTRACT

The present invention relates to the mechanism of ARF-mediated cell growth suppression. ARF-BP1 is identified as a novel ubiquitin ligase, and a major component of ARF-containing nuclear complexes in human cells. The present invention discloses a novel mechanism of ARF-mediated p53 activation and that ARF-BP1 is a critical mediator of both p53-independent and p53-dependent tumor suppression functions of ARF. Inactivation of ARF-BP1 in normal cells stabilizes p53 and induces p53-dependent apoptosis. Inactivation of ARF-BP1, but not Mdm2, in p53-wildtype cells promotes cell growth inhibition in a manner reminiscent of ARF induction. ARF-BP1 directly binds and ubiquitinates p53 and inactivation of endogenous ARF-BP1 is crucial for ARF-mediated p53 stabilization in Mdm2-null cells. ARF-BP1 is advantageous over Mdm2 as a target for suppressing tumor cell growth regardless of p53 status.

6 Claims, 23 Drawing Sheets

OTHER PUBLICATIONS

Liu et al., "Characterization of E3Histone, a Novel Testis Ubiquitin Protein Ligase Which Ubiquinates Histones," Mol Cell Biol, 2005, 25:2819-2831.

Sequence Search (SEQ ID No. 35 is 99.9% identical to SEQ ID No. 2) WO 03/063688 (INCYTE) Aug. 7, 2003.

International Search Report and Written Opinion issued for International Patent Application No. PCT/US2005/032835.

```
   1  MKVDRTKLKK  TPTEAPADCR  ALIDKLKVCN  DEQLLLELQQ  IKTWNIGKCE  LYHWVDLLDR  FDGILADAGQ  TVENMSWMLV
  81  CDRPEREQLK  MLLLAVLNFT  ALLIEYSFSR  HLYSSIEHLT  TLLASSDMQV  VLAVLNLLYV  FSKRSNYITR  LGSDKRTPLL
 161  TRLQHLAESW  GGKENGFGLA  ECCRDLHMMK  YPPSATTLHP  EFYADPGAEV  KIEKRTTSNT  LHYIHIEQLD  KISESPSEIM
 241  ESLTKMYSIP  KDKQMLLFTH  IRLAHGFSNH  RKRLQAVQAR  LHAISILVYS  NALQESANSI  LYNGLIEELV  DVLQITDKQL
 321  MEIKAASLRT  LTSIVHLERT  PKLSSIIDCT  GTASYHGFLP  VLVRNCIQAM  IDPSMDPYPH  QFATALFSFL  YHLASYDAGG
 401  EALVSCGMME  ALLKVIKFLG  DEQDQITFVT  RAVRVVDLIT  NLDMAAFQSH  SGLSIFIYRL  EHEVDLCRKE  CPFVIKPKIQ
 481  RPNTTQEGEE  METDMDGVQC  IPQRAALLKS  MLNFLKKAIQ  DPAPSDGIRH  VMDGSLPTSL  KHIISNAEYY  GPSLFLLATE
 561  VVTVFVPQEP  SLLSSLQDNG  LTDVMLHALL  IKDVPATREV  LGSLPNVFSA  LCLNARGLQS  FVQCQPFERL  FKVLLSPDYL
 641  PAMRRRRSSD  PLGDTASNLG  SAVDELMRHQ  PTLKTDATTA  IIKLLEEICN  LGRDPKYICQ  KPSIQKADGT  ATAPPPRSNH
 721  AAEEASSEDE  EEEEVQAMQS  FNSTQQNETE  PNQQVVGTEE  RIPIPLMDYI  LNVMKFVESI  LSNNTTDDHC  QEFVNQKGLL
 801  PLVTILGLPN  LPIDFPTSAA  CQAVAGVCKS  ILTLSHEPKV  LQEGLLQLDS  ILSSLEPLHR  PIESPGGSVL  LRELACAGNV
 881  ADATLSAQAT  PLLHALTAAH  AYIMMFVHTC  RVGQSEIRSI  SVNQWGSQLG  LSVLSKLSQL  YCSLVWESTV  LLSLCTPNSL
 961  PSGCEFGQAD  MQKLVPKDEK  AGTTQGGKRS  DGEQDGAAGS  MDASTQGLLE  GIGLDGDTLA  PMETDEPTAS  DSKGKSKITP
1041  AMAARIKQIK  FLLSASSRLG  RALAELFGLL  VKLCVGSPVR  QRRSHHAAST  TTAPTPAARS  TASALTKLLT  KGLSWQPPPY
1121  TPTLRFRLTF  FICSVGFTSP  MLFDERKYPY  HLMLQKFLCS  GGHNALFETF  NWALSMGGKV  PVSEGLEHSD  LPDGTGEFLD
1201  AWLMLVEKMV  NPTTVLESPH  SLPAKLPGGV  QNFPQFSALR  FLVVTQKAAF  TCIKNLWNRK  PLKVYGGRMA  ESMLAILCHI
1281  LRGEPVIRER  LSKEKEGSRG  EEDTGQEEGG  SRREPQVNQQ  QLQQLMDMGP  TREHAMEALL  NTSTMEQATE  YLLTHPPPIM
1361  GGVVRDLSMS  EEDQMMRAIA  MSLGQDIPMD  QRAESPEEVA  CRKEEEERKA  REKQEEEEAK  CLEKFQDADP  LEQDELHTFT
1441  DTMLPGCFHL  LDELFPDTVYR  VCDLIMTAIK  RNGADYRDMI  LKQVVNQVWE  AADVLIKAAL  PLTTSDTKTV  SEWISQMATL
1521  PQASNLATRI  LLLTLLFEEL  KLPCAWVVES  SGILNVLIKL  LEVVQPCLQA  AKEQKEVQTP  KWITPVLLLI  DFYEKTAISS
1601  KRRAQMTKYL  QSNSNNWRWF  DDRSGRWCSY  SASNNSTIDS  AWKSGETSVR  FTAGRRRYTV  QFTTMVQVNE  ETGNRRPVML
1681  TLLRVPRLNK  NSKNSNGQEL  EKTLEESKEM  DIKRKENKGN  DTPLALESTN  TEKETSLEET  KIGEILIQGL  TEDMVTVLIR
1761  ACVSMLGVPV  DPDTLHATLR  LCLRLTRDHK  YAMMFAELKS  TRMILNLTQS  SGFNGFTPLV  TLLLRHIIED  PCTLRHTMEK
1841  VVRSAATSGA  GSTTSGVVSG  SLGSREINYI  LRVLGPAACR  NPDIFTEVAN  CCIRIALPAP  RGSGTASDDE  PENLRIKGPN
1921  AVQLVKTTPL  KPSPLPVIPD  TIKEVIYDML  NALAAYHAPE  EADKSDPKPG  VMTQEVGQLL  QDMGDDVYQQ  YRSLTRQSSD
2001  FDTQSGPSIN  SQVPAADGAS  TETSASGTSQ  GEASTPEESR  DGKKDKEGDR  ASEEGKQKGK  GSKPLMFTST  ILRLLAELVR
2081  SYVGIATLIA  NYSYTVGQSE  LIKEDCSVLA  FVLDHLLPHT  QNAEDKDTPA  LARLFLASLA  AAGSGTDAQV  ALVNEVKAAL
2161  GRALAMAEST  EKHARLQAVM  CIISTIMESC  PSTSSFYSSA  TAKTQHNGMN  NIIRLPLKKG  LVNDLARVPH  SLDLSSPNMA
2241  NTVNAALKPL  ETLSRIVNQP  SSLFGSKSAS  SKNKSEQDAQ  GASQDSSSNQ  QDPGEPGEAE  VQEEDHDVTQ  TEVADGDIMD
2321  GEAETDSVVI  AGQPEVLSSQ  EMQVENELED  LIDELLERDG  GSGNSTIIVS  RSGEDESQED  VLMDEAPSNL  SQASTLQANR
2401  EDSMNILDPE  DEEEHTQEED  SSGSNEDEDD  SQDEEEEEEB  DEEDDQEDDE  GEEGDEDDDD  DGSEMBLDED  YPDMNASPLV
2481  RPERFDREDD  LIIEFDNMFS  SATDIPPSPG  NIPTTHPLMV  RHADHSSLTL  GSGSSTTRLT  QGIGRSQRTL  RQLTANTGHT
2561  IHVHYPGNRQ  PNPPLILQRL  LGPSAAADIL  QLSSSLPLQS  RGRARLLVGN  DDVHIIARSD  DELLDDPFHD  QSTATSQAGT
2641  LSSIPTALTR  WTEBCKVLDA  ESMHDCVSVV  KVSIVNHLEP  LRDEELEERR  EKRRKQLAEE  ETKITDKGKE  DKENRDQSAQ
2721  CTASKSNDST  EQNLSDGTPM  PDSYPTTPSS  TDAATSESKE  TLGTLQSSQQ  QPTLFTPPAL  GEVPQELQSP  AGEGGSSTQL
2801  LMPVEPEELG  PTRPSGEAET  TQMELSPAPT  ITSLSPERAE  DSDALTAVSS  QLEGSPMDTS  SLASCTLEEA  VGDTSAAGSS
2881  EQPRAGSSTP  GDAPPAVAEV  QGRSDGSGES  AQPPEDSSPP  ASSESSSTRD  SAVAISGADS  RGILEEPLPS  TSSEEEDPLA
2961  GISLPEGVDP  SFLAALPDDI  RREVLQNQLG  IRPPTRTAPS  TNSSAPAVVG  NPGVTEVSPE  FLAALPPAIQ  EEVLAQQRAE
3041  QQRRELAQNA  SSDTPMDPVT  FIQTLPSDLR  RSVLEDMEDS  VLAVMPPDIA  AEAQALRREQ  EARQRQLMHE  RLFGHSSTSA
3121  LSAILRSPAF  TSRLSGNRGV  QYTRLAVQRG  GTFQMGGSSS  HNRPSGSNVD  TLLRLRGRLL  LDHEALSCLL  VLLFVDEPKL
3201  NTSRLHRVLR  NLCYHAQTRH  WVIRSLLSIL  QRSSBSELCI  ETPKLTTSEE  KGKKSSKSCG  SSSHENRPLD  LLHKMESKSS
3281  NQLSWLSVSM  DAALGCRTNI  FQIQRSGGRK  HTEKHASGGS  TVHIHPQAAP  VVCRHVLDTL  IQLAKVFPSH  FTQQRTKETN
3361  CESDRERGNK  ACSPCSSQSS  SSGICTDFWD  LLVKLDNMNV  SRKGKNSVKS  VPVSAGGEGE  TSPYSLEASP  LGQLMNMLSH
3441  PVIRRSSLLT  EKLLRLLSLI  SIALPENKVS  EAQANSGSGA  SSTTTATSTT  STTTTTAAST  TPTPPTAPTP  VTSAPALVAA
3521  TAISTIVVAA  STTVTTPTTA  TTTVSISPTT  KGSKSPAKVS  DGGSSSTDFK  MVSSGLTENQ  LQLSVEVLTS  HSCSEEGLED
3601  AANVLLQLSR  GDSGTRDTVL  KLLLNGARHL  GYTLCKQIGT  LLAELREYNL  EQQRRAQCET  LSPDGLPEEQ  PQTTKLLKGKM
3681  QSRFDMAENV  VIVASQKRPL  GGRELQLPSM  SMLTSKTSTQ  KFFLRVLQVI  IQLRDDTRRA  NKKAKQTGRL  GSSGLGSASS
3761  IQAAVRQLEA  EADAIIQMVR  EGQRARRQQQ  AATSESSQSE  ASVRREESPM  DVDQPSPSAQ  DTQSIASDGT  PQGEKEKEER
3841  PPELPLLSEQ  LSLDELWDML  GECLKELEES  HDQHAVLVLQ  PAVEAFFLVH  ATERESKPPV  RDTRESQLAH  IKDEPPPLSP
3921  APLTPATPSS  LDPFPSREPS  SMHISSSLPP  DTQKFLRPAE  THRTVLNQIL  RQSTTHLADG  PFAVLVDYIR  VLDFDVKRKY
4001  FRQELERLDE  GLRKEDMAVH  VRRDHVFEDS  YRELHRKSPE  EMKNRLYIVF  EGEEGQDAGG  LLREWYMIIS  REMFNPMYAL
4081  FRTSPGDRVT  YTINPSSHCN  PNHLSYPKFV  GRIVAKAVYD  NRLLECYFTR  SFYKHILGKS  VRYTDMESED  YHFYQGLVYL
4161  LENDVSTLGY  DLTFSTEVQE  PGVCEVRDLK  PNGANILVTE  ENKKEYVHLV  CQMRMTGAIR  KQLAAFLEGF  YEIIPKRLIS
4241  IFTEQELELL  ISGLPTIDID  DLKSNTEYHK  YQSNSIQIQW  FWRALRSFDQ  ADRAKFLQPV  TGTSKVPLQG  PAALEGMNGI
4321  QKFQIHRDDR  STDRLPSAHT  CFNQLDLPAY  ESFEKLRHML  LLAIQECSEG  FGLA
```

Figure 3

UBA

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| human ARF-BP1 | N | Q | Q | Q | L | Q | Q | L | M | D | M | G | F | T | R | E | H | A | M | E | A | L | L | N | T | S | T | M | E | - | Q | T | T | F | Y | L | T |
| mouse ARF-BP1 | N | Q | Q | Q | L | Q | Q | L | M | D | M | G | F | T | R | E | H | A | M | E | A | L | L | N | T | S | T | M | E | - | Q | T | T | F | Y | L | T |
| yeast RAD23 | L | S | S | E | I | E | N | L | M | S | Q | G | Y | S | Y | Q | D | I | Q | K | A | L | V | I | A | Q | N | H | I | E | M | A | K | N | I | L | R | E |
| human HHR23A | E | E | T | X | L | T | E | I | M | S | M | G | I | E | R | E | R | V | V | A | A | L | R | A | S | Y | N | N | P | H | R | A | V | F | Y | L | T |
| human Cbl | R | N | E | T | I | E | R | I | M | E | M | G | Y | Q | K | E | E | V | E | R | A | L | R | A | A | F | N | N | P | D | R | A | V | F | Y | L | L | M |
| human Cbl-b | V | D | A | K | I | A | K | L | M | G | E | S | Y | A | F | E | E | V | K | R | A | L | E | I | A | Q | N | N | V | E | V | A | R | S | I | L | R | E |

Figure 4

ARF-BP1 AS MEDIATOR OF P53-DEPENDENT AND INDEPENDENT TUMOR SUPPRESSION AND USES THEREOF

CROSS-REFERENCE TO RELATED APPLICATION

The present application claims the benefit of U.S. Provisional Application Ser. No. 60/610,506, filed on Sep. 15, 2004, which is incorporated herein by reference thereto.

STATEMENT OF GOVERNMENT INTEREST

This invention was made, in part, with government support under NIH grant No. CA097403. As such, the United States government has certain rights in this invention.

FIELD OF THE INVENTION

The present invention relates to the mechanism of ARF-mediated cell growth suppression, and more specifically to the p53/Mdm2-independent function of ARF.

BACKGROUND OF THE INVENTION

Neoplasia is a disease characterized by an abnormal proliferation of cell growth known as a neoplasm. Neoplasms may manifest in the form of a leukemia or a tumor, and may be benign or malignant. Malignant neoplasms, in particular, can result in a serious disease state, which may threaten life. Significant research efforts and resources have been directed toward the elucidation of antineoplastic measures, including chemotherapeutic agents, which are effective in treating patients suffering from neoplasia. Effective antineoplastic agents include those which inhibit or control the rapid proliferation of cells associated with neoplasms, those which effect regression or remission of neoplasms, and those which generally prolong the survival of patients suffering from neoplasia. Successful treatment of malignant neoplasia, or cancer, requires elimination of all malignant cells, whether they are found at the primary site, have extended to local/regional areas, or have metastasized to other regions of the body. The major therapies for treating neoplasia are surgery and radiotherapy (for local and local/regional neoplasms) and chemotherapy (for systemic sites).

Despite the various methods for detecting, diagnosing, and treating cancers, the disease remains prevalent in all segments of society, and is often fatal. Clearly, alternative strategies for detection (including the development of markers that can identify neoplasias at an early stage) and treatment are needed to improve survival in cancer patients. In particular, a better understanding of tumor suppressors, and tumor-suppression pathways, would provide a basis from which novel detection, diagnostic, and treatment regimens may be developed.

The p53 tumor suppressor exerts anti-proliferative effects, including growth arrest, apoptosis, and cell senescence, in response to various types of stress (Levine, A. J., Cell 88:323-31, 1997; Oren, M., J. Biol. Chem. 274: 36031-034, 1999). p53 can be thought of as the central node of a regulatory circuit that monitors signaling pathways from diverse sources, including DNA damage responses (e.g., ATM/ATR activation), abnormal oncogenic events (e.g., Myc or Ras activation) and everyday cellular processes (e.g., growth factor stimulation). While p53 mutations have been well documented in more than half of all human tumors (Hollstein et al., Mutat Res. 431:199-209, 1999), defects in other components of the p53 pathway, such as the ARF tumor suppressor, are observed in tumor cells that retain wildtype p53 (Sherr, C. J., Nat Rev Mol Cell Biol 2:731-737, 2001; Sharpless, N. E., DePinho, R. A., J Clin Invest 113:160-8, 2004). Activation of the p53 pathway appears to be a common, if not universal, feature of human cancer.

The mechanisms of p53 activation are not fully understood, but are generally thought to entail post-translational modifications, such as ubiquitination, phosphorylation and acetylation. Ubiquitination of p53 was first discovered in papilloma-infected cells, where p53 degradation is mediated by the viral E6 protein and a HECT-domain containing ubiquitin ligase called E6-AP (Munger, K., Howley, P. M., Virus Res 89:213-228, 2002). In normal cells, Mdm2 acts as a specific E3 ubiquitin ligase for p53, which, if malignantly activated, has the potential to counteract the tumor suppressor activity of p53. The critical role of Mdm2 in regulating p53 is illustrated by studies carried out in mice where inactivation of p53 was shown to completely rescue the embryonic lethality caused by loss of Mdm2 function (Montes de Oca Luna, R., Wagner, D. S., Lozano, G., Nature 378:203-206, 1995).

Although earlier studies suggested that Mdm2 is the primary factor in controlling p53 stabilities, the degradation of p53 is more complex than originally anticipated. The present inventor found that Mdm2 differentially catalyzes either monoubiquitination and polyubiquitination of p53 in a dosage-dependent manner (Li, M., Brooks, C. L., Wu-Baer, F., Chen. D., Baer, R., Gu, W., Science 302:1972-1975, 2003). Low levels of Mdm2 activity induce monoubiquitination and nuclear export of p53, whereas high levels promote polyubiquitination and nuclear degradation of p53. These mechanisms are exploited in different physiological settings. On one hand, Mdm2-mediated polyubiquitination and nuclear degradation may play a dominant role in suppressing p53 function when Mdm2 is malignantly overexpressed or during the late stages of a DNA damage response. On the other hand, Mdm2-mediated monoubiquitination and subsequent cytoplasmic translocation of p53 may represent an important means of p53 regulation in unstressed cells, where Mdm2 is maintained at low levels (Li et al., 2003, supra). Moreover, additional cellular factors may be necessary to facilitate p53 degradation, particularly when endogenous Mdm2 activities are not sufficient to catalyze p53 polyubiquitination directly. It was recently reported that ubiquitin ligases COP1 and Pirh2 are directly involved in p53 degradation (Dornan, D., Wertz, L, Shimizu, H., Arnott, D., Frantz, G. D., Dowd, P., O'Rourke, K., Koeppen, H., Dixit, V. M., Nature 429:86-92, 2004). Therefore, while Mdm2 is a key regulator of p53 function, p53 degradation acts through both Mdm2-dependent and Mdm2-independent pathways in vivo.

ARF (known as p14$^{ARF}$ in humans and p19$^{ARF}$ in mouse) was identified as an alternative transcript of the Ink4a, ARF tumor suppressor locus, a gene that encodes the p16$^{Ink4a}$ inhibitor of cyclin-dependent kinases. By virtue of its unique first exon, the ARF transcript encodes a protein that is unrelated to p16$^{Ink4a}$. Nevertheless, ARF, like p16$^{Ink4a}$, exhibits tumor suppression functions, as demonstrated by the tumor susceptibility phenotype of p14$^{ARF}$-deficient mice. ARF suppresses abherrant cell growth in response to oncogene activation, at least in part, by inducing the p53 pathway (Sherr, et al., 2001, supra). The ARF induction of p53 appears to be mediated through Mdm2, since overexpressed ARF interacts directly with Mdm2 and inhibits its ability to promote p53 degradation (Zhang, Y., Xiong, Y., Yarbrough, W. G., *Cell* 92:125-34, 1998). The mechanisms by which ARF modulates the Mdm2/p53 pathway appears to be complex, both stabilizing p53 by binding and sequestering Mdm2 and activating p53 function by directly inhibiting the ubiquitin ligase activity of Mdm2.

Interestingly, ARF also has tumor suppressor functions that do not depend on p53 or Mdm2. For example, although ARF can induce cell growth arrest in tumor cells that lack a functional p53 gene (Normand, G., Hemmati, P. G., Verdoodt, B. et al., *J. Biol Chem* 280:7118-30, 2005) or a gene encoding the p21 cyclin-dependent kinase inhibitor, a key transcriptional target of p53, ARF can also suppress the proliferation of MEFs lacking both Mdm2 and p53. Consistent with these findings, the tumor susceptibility of triple knockout mice that lack ARF, p53 and Mdm2 is significantly greater than that associated with mice lacking any one of these genes alone. It was recently shown that ARF suppresses the growth, progression, and metastasis of mouse skin carcinomas through both p53-dependent and p-53 independent pathways (Kelly-Sprat, K. S., Gurley, K. E., Yasui, Y., Kemp, C. J., *PLoS Biol.* 2:E242, 2004). Distinct downstream factors may exist that mediate the p53-independent functions of ARF. The identity of these factors and the mechanisms by which they mediate p53-independent tumor suppression by ARF are unknown. Accordingly, while regulation of the p53 pathway is of intense interest and presents a potential means of diagnosing and treating cancers, a greater understanding of this pathway and the factors and mechanisms that mediate the p53 independent functions of ARF would provide a valuable basis upon which new diagnostic and therapeutic methods may be developed.

SUMMARY OF THE INVENTION

The present invention is based upon the discovery of a novel protein, ARF-BP1, which, when inactivated induces cell growth inhibition in p53 null cells and p53-dependent apoptosis in p53 wild-type cells. This discovery has broad implications in the diagnosis, monitoring, and treatment of neoplasias, particularly cancers associated with p53.

According to the invention, it has surprisingly been found that inactivation of ARF-BP1 induced cell growth arrest in p53 null cells, indicating that ARF-BP1 is a critical mediator of the p53-independent pathway of tumor suppression. Inactivation of endogenous ARF-BP1, but not Mdm2, in p53-null cells induces cell growth repression to a manner reminiscent of ARF induction. Inactivation of ARF-BP1 in p53 positive cells induced p53 stabilization and activated a p53-dependent apoptotic response. Accordingly, one aspect of the invention features a novel regulatory pathway involving ARF-BP1 in mediating both the p53-independent and p53-dependent tumor suppressor functions of ARF.

Accordingly, the present invention provides a method for determining whether a subject has neoplasia, by assaying a diagnostic sample of the subject for ARF-BP1 peptide expression, wherein detection of ARF-BP1 expression is diagnostic of neoplasia in the subject.

The present invention provides a method for screening for preneoplastic and genetic predisposition for carcinomas, by assaying a diagnostic sample of the subject for ARF-BP1 peptide expression, wherein detection of ARF-BP1 expression is diagnostic of preneoplasia and genetic predisposition for carcinomas in the subject.

The present invention also provides a method for assessing the efficacy of therapy to treat neoplasia in a subject who has undergone or is undergoing therapy for neoplasia, by assaying a diagnostic sample of the subject for ARF-BP1 expression, wherein decreased or normal ARF-BP1 expression in the diagnostic sample is indicative of successful therapy, and ARF-BP1 expression elevated above normal in the diagnostic sample is indicative of a need to continue therapy to treat neoplasia.

The present invention further provides a method for assessing the prognosis of a subject who has neoplasia, by assaying a diagnostic sample of the subject for ARF-BP1 expression, wherein the subject's prognosis improves with a decrease in ARF-BP1 expression in the diagnostic sample, the subject's prognosis worsens with an increase in ARF-BP1 expression in the diagnostic sample.

The present invention also provides a kit for use in detecting neoplasia, comprising: (a) an agent reactive with ARF-BP1; and (b) reagents suitable for detecting expression of ARF-BP1.

Additionally, the present invention provides a method for treating neoplasia in a subject in need of treatment, by decreasing activity of ARF-BP1 in the subject. Also provided is a pharmaceutical composition, comprising an inhibitor of ARF-BP1 expression or an ARF-BP1 protein, in an amount effective to treat neoplasia in a subject to whom the composition is administered, and a pharmaceutically acceptable carrier.

The present invention further provides a method for deubiquitinating p53 in a cell, by contacting the cell with ARF-BP1, in an amount effective to deubiquitinate p53. Also provided is a method for treating neoplasia in a subject in need of treatment, by deubiquitinating p53 in a cell of the subject.

Additionally, the present invention is directed to a method for identifying an agent that is reactive with p53, by: (a) contacting a candidate agent with p53, in the presence of ARF-BP1; and (b) assessing the ability of the candidate agent to inhibit ARF-BP1-p53 interaction. Optionally, this method of the present invention may further comprise the steps of: (c) contacting the candidate agent with one or more cells containing p53; and (d) determining if the agent has an effect on a p53-associated biological event in the one or more cells.

The present invention further provides a method for treating a p53-associated condition in a subject in need of treatment, by administering to the subject an amount of an ARF-BP1 inhibitory agent effective to treat the p53-associated condition in the subject.

In one aspect of the invention ARF-BP1 directly binds ARF and its ubiquitin ligase activities are strongly inhibited by ARF. Accordingly, the present invention also provides a complex comprising ARF and ARF-BP1, and a mutant ARF-BP1 comprising the ARF-BP1 amino acid sequence.

Finally, the present invention is directed to a transgenic non-human animal whose genome comprises a disruption in its endogenous ARF-BP1 gene, wherein the transgenic animal exhibits decreased expression of functional ARF-BP1 protein relative to wild-type.

According to the invention, ARF-BP1 has been identified as a major component of ARF-containing protein complexes from p53-null human cells. In particular, the present invention characterizes ARF-BP1, a HECT (homology to E6-AP-C-terminus)-containing ubiquitin ligase.

Another aspect of the invention provides that ARF-BP1 interacts with both ARF and p53, respectively, but not with Mdm2. ARF-BP1 is required for ARF-mediated p53 stabilization in Mdm2 nulls The present invention provides a practical approach for therapeutic intervention in tumors regardless of p53 status where ARF-BP1 may serve as a universal target.

Yet another aspect of the invention provides that ARF-BP1 is widely expressed and contains signature motifs (HECT and UBA) commonly associated with protein ubiquitination. ARF-BP1 catalyzes in vitro ubiquitination of p53 and RNAi-mediated inactivation of endogenous ARF-BP1 in p53-wild-type cells and stabilizes p53 and activates p53 function.

Additional aspects of the present invention will be apparent in view of the description which follows.

BRIEF DESCRIPTION OF THE FIGURES

FIG. 1A is a schematic representation of the HA-ARF-Flag-protein. FIG. 1B depicts the expression levels of HA-ARF-Flag and endogenous ARF in ARF-stable lines using Western blot analysis of cell extracts from parental H1299 cell line (lane 1), ARF stable cell line clone #1 (lane 2), and ARF stable cell line clone #2 (lane 3) with an anti-ARF antibody. FIG. 1C illustrates the silver staining of affinity-purified ARF-complexes from a nuclear extract of the HA-ARF-Flag/H1299 stable cell line (lane 2) and a control eluate from a parental H1299 nuclear cell extract (lane 1). Specific ARF-interacting protein bands were analyzed by mass spectrometry, and the p500/ARF-BP1 and B23/NPM (Nucleophosmin) peptide sequences (SEQ ID NOS. 3-6 from top to bottom in FIG. 1C).

FIG. 2A is a schematic representation of the ARF-BP1 polypeptides. FIG. 2B depicts an alignment of the HECT domain of human ARF-BP1 (SEQ ID NO:7) with mouse ARF-BP1 (SEQ ID NO:8) and human E6-AP (SEQ ID NO:9) where the homologous amino acid residues are highlighted in outline and shadow. FIG. 2C depicts the expression of ARF-BP1 in different types of human tissue. A multiple tissue Northern filter was hybridized with ARF-BP1 (upper) or actin (lower) cDNA probes.

FIG. 3 sets forth the amino acid sequence of ARF-BP1 and is identified as SEQ ID NO: 2.

FIG. 4 illustrates the presence of a UBA domain of ARF-BP1 with alignment of human ARF-BP1 (SEQ ID NO:10), mouse ARF-BP1 (SEQ ID NO:11), yeast rad23 (SEQ ID NO:12), human HHR23A (SEQ ID NO:13), human Cb1 (SEQ ID NO:14) and Cb1-b (SEQ ID NO:15) and homologous amino acid residues highlighted in outline and shadow.

FIG. 5A depicts the direct interaction of ARF-BP1 with GST-ARF using the wild-type GST-ARF full-length protein (GST-ARF) (lanes 3, 9), the mutant GST-ARF (GST-ARF (GST-ARF Δ1-14) (lane 4), the N terminus of ARF protein (1-64) (lane 5), the C terminus of ARF (65-132) (lane 6), or GST alone (lanes 2, 8) in a pull-down assay either with an in vitro translated $^{35}$S-labeled ARF-BP1 (1015-4374) (lanes 1-6), or with in vitro translated $^{35}$S-labeled ARF-BP1 (1-1014) (lanes 7-9). FIG. 5B depicts coimmunoprecipitation of ARF with ARF-BP1 from H1299 cells using a Western blot analysis of indicated whole cell extract (lane 1) and immunoprecipitates with an ARF-BP1-specific antibody (lane 3) or a control IgG (lane 2) by anti-ARF monoclonal antibody (lower) or anti-ARF-BP1 antibody (top). FIG. 5C depicts coimmunoprecipitation of ARF-BP1 with ARF from H1299 cells using a Western blot analysis of whole cell extract (lane 1) or immunoprecipitates with anti-ARF polyclonal antibody (lane 3) or a control anti-serum (lane 2) by an ARF-BP1-specific antibody (lower) or anti-ARF monoclonal antibody (top). FIG. 5D shows the ubiquitination activity of ARF-BP1 is inhibited by ARF using Western blot analysis of the ubiquitin conjugates by anti-GST antibody. The in vitro ubiquitination assay was set up by incubating GST-ARF-BP1 (3760-4374) with E1, E 2 (His-UBCH5a), and ubiquitin (lane 2), or in the presence of GST-ARF (lane 3), GST-NARF (lane 4) or GST-CARF (lane 5), respectively.

FIG. 6A depicts ablation of endogenous ARF-BP1 and Mdm2 proteins by RNAi using Western blot analysis of cell extracts of H1299 cells treated with a control RNAi (GFP-RNAi) (lane 1), Mdm2 RNAi (lane 2), or ARF-BP1 RNAi #1 (lane 3) with the antibodies against ARF-BP1, Mdm2, p21 and actin. FIG. 6B depicts overall cell growth of H1299 cells treated with a control RNAi (GFP-RNAi), Mdm2 RNAi, or ARF-BP1 RNAi # 1 stained with crystal violet three days after siRNA treatment. FIG. 6C depicts BrdU incorporation of H1299 cells treated with a control RNAi (GFP-RNAi), Mdm2 Nai, or ARF-BP1 RNAi #1 with labeling and staining of the cells one day after RNAi treatment. FIG. 6D is a bar graph showing that RNAi-mediated ablation of ARF-BP1 induces cell growth inhibition in p53 null SaoS-2 cells and the percentages of BrdU positive cells, 24 hours after transfection with control RNAi, Mdm2-RNAi or ARF-BP1-RNAi where the cells were counted and averaged in three independent experiments. FIG. 6E is a bar graph showing that RNAi-mediated ablation of ARF-BP1 induces cell growth inhibition in p53 null SaoS-2 cells and the number of Saos2 cells after being treated with control RNAi, Mdm2-RNAi or ARF-BP1-RNAi where the cells were counted and averaged in three independent experiments.

FIG. 7A depicts ablation of endogenous ARF-BP1 and Mdm2 proteins by RNAi and shows Western blot analysis of H1299 cell extracts treated with a control RNAi (GFP-RNAi) (lane 1), Mdm2 RNAi (lane 2), or ARF-BP1 RNAi #2 (lane 3) with the antibodies against ARF-BP1, Mdm2, p21 and actin. FIG. 7B is a line graph showing the growth curves of H1299 cells treated with a control RNAi (GFP-RNAi), Mdm2 RNAi, or ARF-BP1 RNAi#2. After treatment with different types of siRNA, the cells were seeded with 2×10$^6$ cells per plate in fresh medium, and counted each day. FIG. 7C depicts overall cell growth of the H1299 cells treated with a control RNAi (GFP-RNAi), Mdm2 RNAi, or ARF-BP1 RNAi#2 where the cells were stained with crystal violet three days after siRNA treatment. FIG. 7D depicts endogenous ARF-BP1 ablated by RNAi in human U2OS cells and shows Western blot analysis of cell extracts of native U2OS cells (lane 1), U2OS cells treated with a control RNAi (GFP-RNAi) (lane 2), or ARF-BP1 RNAi#2 (lane 3) with the antibodies against ARF-BP1, P53, p21, bax and actin.

FIG. 8A shows the cell cycle profile of control RNAi plus control virus treatment (i), ARF-BP1 RNAi (ii), adenovirus-ARF treatment (iii) and ARF-BP1 RNAi plus adenovirus-ARF treatment. FIG. 8B is a bar graph representation of G2M arrest in H1299 cells.

9A depicts endogenous ARF-BP1 knockdown by RNAi in human U2OS cells and shows Western blot analysis of cell extracts of native U2OS cells (lane 1), the U2OS cells treated with a control RNAi (GFP-RNAi) (lane 2), or ARF-BP1 RNAi # (lane 3) with the antibodies against ARF-BP1, p53, p21, bax and actin. FIG. 9B depicts the inactivation of ARF-BP1 extending the half life of endogenous p53 protein and showing Western blot analysis of cells extracts with an anti-p53 (DO-1) antibody from ARF-BP1-RNAi, or control-RNAi-transfected cells, harvested at indicated time points (min.) after cyclohexamide (CHX) treatment. FIG. 9C shows that inactivation of ARP-BP1 induced apoptosis. U2OS cells transfected with either ARF-BP1-RNAi or control-RNAi were analyzed for apoptotic cells (sub-G1) according to DNA content (PI staining). FIG. 9D depicts the reintroduction of ARF-BP1 (R) as abrogating ARF-BP1 RNAi-mediated p53 upregulation and shows Western blot analysis of cell extracts of U2OS cells treated with control-RNAi (GFP-RNAi) (lane 1), ARF-BP1-RNAi #2 (lane 2), or a combination of ARF-BP1-RNAi #1 and ARF-BP1 (R) (lane 3), ARF-BP1-RNAi #1 and ARF-BP1M (R) (lane 4) with the antibodies against ARF-BP1, p53, p21 and actin. FIG. 9E shows Western blot analysis of cell extracts from parental HCT116 cells (lane 1, 2) or HCT116-p53$^{-/-}$ cells (lane 3, 4) treated with either control RNAi (lanes 1, 3) or ARF-BP1-RNAi (lanes 2, 4), with the antibodies against ARF-BP1, Mdm2, p53, p21, Myc and actin.

FIG. 14A is a schematic of ARF-BP1 mutation (ARF-BP1(M)), ARF-BP1#1RNAi resistant construct (ARF-BP1(R)) and its mutation (ARF-BP1M(R)). The nucleic acid AATTGCTAT-GTCTCTG (SEQ ID NO:16) has been mutated to AAT-TGATATCCTCTG (SEQ ID NO:17) for both ARF-BP1(R) and ARF-BP1M(R).

FIG. 16A shows direct interactions of ARF-BP1 with GST-p53. The GST-p53 protein (lane 3, 7), the GST-Mdm2 (line 4, 8), or GST alone (lanes 2, 6) were used in a GST pull-down assay with in vitro translated $^{35}$S-labeled ARF-BP1 (1015-4374) (lane 1-4) or ARF-BP1 (1-1014) (lane 5-8). FIG. 16B depicts coimmunoprecipitation of p53 with ARF-BP1 from U2OS cells. Western blot analysis of whole-cell extract (WCE) (lane 1) or immunoprecipitates with anti-ARF-BP1 specific antibody (lane 3) or a control IgG (lane 2) by a p53 monoclonal antibody DO-1 (lower) or ARP-BP1 specific antibody (top). FIG. 16C depicts coimmunoprecipitation of ARF-BP1 with p53 from U2OS cells. Western blot analysis of indicated whole-cell extract (WCE) (lane 1) and immunoprecipitates with a p53 monoclonal antibody DO-1 (lane 3) or control antibody (lane 2) by anti-ARF-BP1 specific antibody (lower) or anti-p53 DO-1 antibody (top). FIG. 16D depicts that ARF-BP1-mediated ubiquitination of p53 is inhibited by ARF. After incubation of Flag-p53 with GST-ARF-BP1 (3760-4374) in the presence of E1, E2 and ubiquitin (HA-Ub), the generated ubiquitin-conjugates were immunoprecipitated by the Flag/M2 beads and analyzed by Western blot with the anti-p53 DO1-antibody. The recombinant bacteria expressed protein GST-ARF, NARF (1-64), or CARF-(65-132) were added in the reactions in lanes 3, 4 or 5 respectively.

FIG. 17A shows ARF stabilizes p53 in Mdm2-null cells. Western blot analysis of cell extracts from MEF p53/Mdm2-double null cells transfected with expression vectors of p53 and ARF with a p53 antibody (DO-1). FIG. 17B shows inactivation of ARF-BP1 stabilizes p53 in Mdm2-null cells. Western blot analysis of cell extracts from MEF p53/Mdm2-double null cells transfected with the p53 expression vector together with either ARF-BP1 RNAi or Mdm2 RNAi, by a p53 antibody (DO-1). FIG. 17C demonstrates that ARP-BP1 is required for ARF-mediated p53 stabilization in Mdm2-null cells. Western blot analysis of cell extracts from MEF p53/Mm2-double null cells transfected with expression vectors of p53 and ARF, together with either ARF-BP1 RNAi or Mdm2 RNAi, by a p53 antibody (DO-1), anti-ARF, anti-ARF BP1 and anti-GFP antibodies.

FIG. 18A shows Western blot analysis of cells extracts with an anti-p53 (DO-1) antibody, from ARF-BP1-RNAi, or control RNAi transfected MEF p53/Mdm2-double null cells, harvested at indicated time points (hr) after cyclohexamide (CHX) treatment. The exposure time in the left panel (lane 1-4) is longer than that in the right panel (lane 5-8) so that the base intensity of p53 at time 0 between control RNAi and ARF-BP1 RNAi is comparable. FIG. 18B is a line graph showing the quantitation of the p53 half life in the MEF p53/Mdm2-double null cells treated with control RNAi or ARF-BP RNAi as shown in FIG. 18A.

FIG. 19A shows that reduction of ARF-BP1 has the most significant effect on p53 levels when compared with the known ligases for p53, including Mdm2, COP1, Pirh2. Western blot analysis of cell extracts from U2OS treated with control RNAi (lane 1), Mdm2 RNAi (lane 2), COP1 RNAi (lane 3), Pirh2 RNAi (lane 4) and ARF-BP1 RNAi (lane 5), with the antibodies against ARF-BP1, Mdm2, Pirh2, p53, p21, Bax and actin. FIG. 19B is a model for cooperative controls of the p53-dependent and p53-independent functions of ARF by ARF-BP1 and Mdm2. FIG. 19C shows ARF-BP1 expressions in breast cancer cell lines. Western blot analysis of cell extracts from a number of breast cancer cell lines compared with the normal breast cell line MCF-10A as well as the normal human fibroblast NHF cell line by anti-ARF-BP1 specific antibody and anti-actin antibody.

FIG. 22A shows ARF-BP1 interacts with B23 in vitro. The GST-B23 protein (lane 3), or GST alone (lane 2) were used in a GST pull-down assay with in vitro translated $^{35}$S-labeled ARF-BP 1 (1015-4374) (lanes 1-3) or ARF-BP1 (1-1014) (lanes 4-6). FIG. 22B shows ARF-BP1 interacts with B23 in vivo. Western blot analysis of whole cell extracts (lanes 1 and 2) or immunoprecipitates with the anti-FLAG M2 beads (IP/M2) (lanes 3 and 4) from cells stably transfected with FLAG-B23 (lanes 2 and 4) or control without transfection (lane 1 and 3) by anti-ARF-BP1 specific antibody. FIG. 22C shows that ARF-BP1 does not mediate B23 ubiquitination. After incubation of GST-B23 with GST-ARF-BP1 in the presence of E1, E2 and ubiquitin (HA-Ub), the reactions were analyzed by Western blot with the anti-B23-antibody. FIG. 22D shows ablation of ARF-BP1 does not affect B23 levels. Western blot analysis of cell extracts of SJSA (lane 1-3) or U2OS cells (lane 4-6) treated with a control RNAi (GFP-RNAi) (lanes 2, 5), ARF-BP 1 RNAi (lanes 3, 6), or without treatment (lanes 1, 4) with the antibodies against ARF-BP1, p53, B23 and actin.

DETAILED DESCRIPTION OF THE INVENTION

Figure 1:
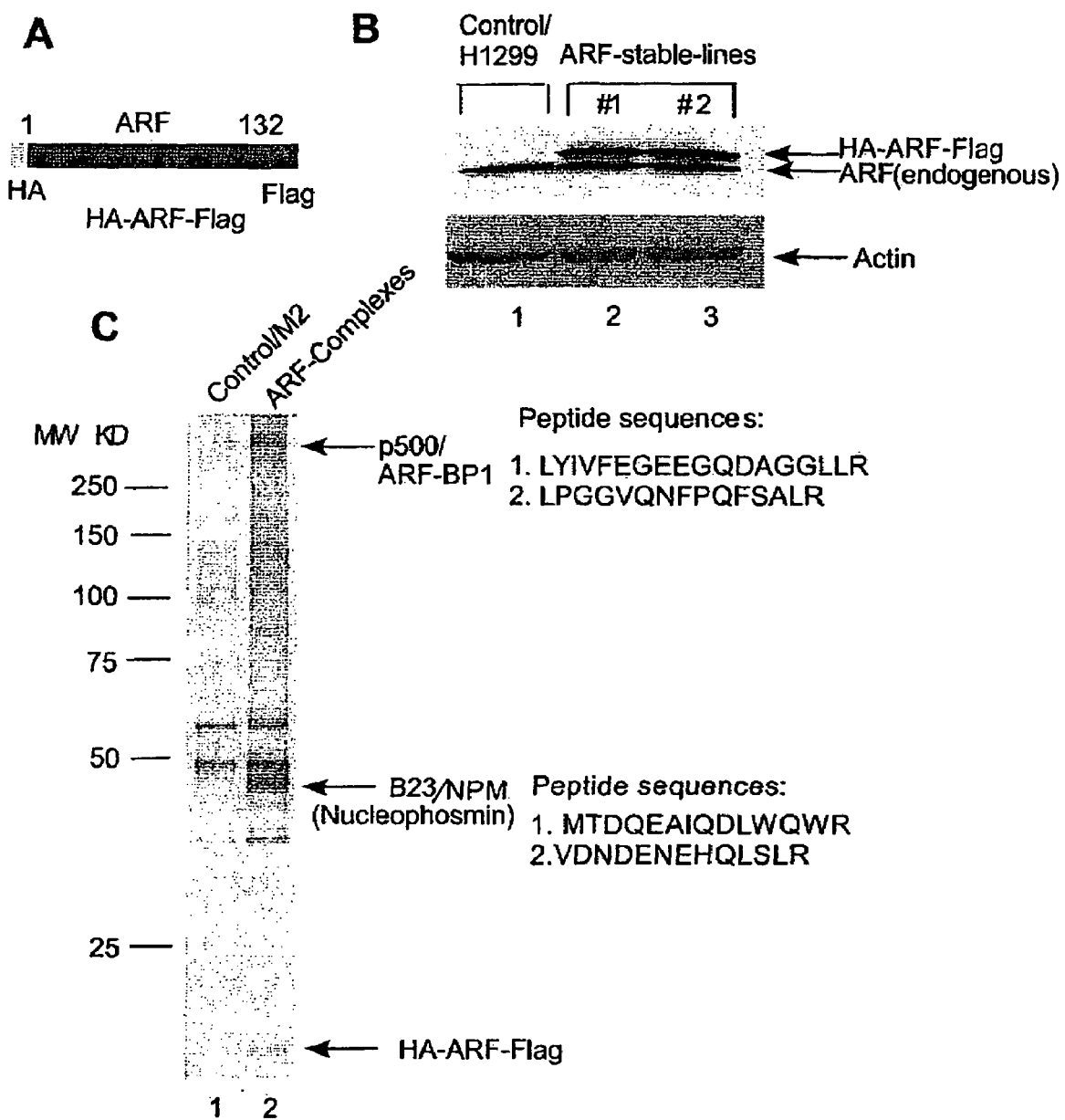
FIGS. 1A-C illustrate identification of ARF-BP1 as a major component of the ARF-associated nuclear complexes in human cells.

Since ARF can stabilize p53 in an Mdm2-independent manner and inactivation of ARF-BP1 directly leads to p53 activation, this invention modifies the current view about how ARF activates p53 in vivo, whose primary target has been presumed to be Mdm2. Moreover, given that inactivation of ARF-BP1 induces cell growth inhibition in p53 null cells and p53-dependent apoptosis in p53-wild-type cells, ARF-BP1 is a universal target for therapeutic intervention in tumors regardless of p53 status.

Beside use for regulating p53 protein and hence application in the control of cell proliferation, the ARF-BP1 peptide of the invention is also useful for in vitro screening methods for therapeutic agents (e.g., antineoplastic agents), for diagnosis and treatment of neoplastic or preneoplastic pathological conditions and genetic diseases.

The Identification of ARF-BP1 Reveals a Novel Aspect of ARF-Mediated Effect In p53 Activation It is well accepted that the ARF polypeptide, as a product of an alternative reading frame of the INK4a locus, is a bona fide tumor suppressor (Sherr et al., 2001, supra; Sharpless, N. E., DePinho, R. A., 2004, supra). The first clue for ARF in activating the p53 pathway came from the tissue culture experiments showing that p53 stabilization is crucial for ARF-mediated function (Kamijo, T., et al., Cell 91:649-659, 1997). At the time, the role of Mdm2 in ubiquitination and degradation of p53 was just discovered (Haupt et al., Nature 387:296-299, 1997; Honda, R., Tanaka, H., Yasuda, H., FEBS Lett 420:25-27,1997; Kubbutat, M. H., Jones, S. N., Vousden, K. H., Nature 387:299-303, 1997). Mostly based on the results derived from over-expression settings, this seemingly obvious connection between ARF and Mdm2 was immediately accepted as the primary pathway for ARF-mediated p53 activation (Sherr et al., 2001, supra), which apparently leaves no room for the possibility of other factors involved in this pathway.

However, several lines of evidence indicate that ARF-mediated activation of p53 is much more complicated than a simple ARF-Mdm2 model. For example, the ARF-Mdm2 interaction was discovered in overexpression settings. However, the expression levels of Mdm2 in normal cells are low; whether endogenous ARF interacts with endogenous Mdm2 in normal cells remains an unsolved issue. Furthermore, low levels of Mdm2, which are commonly observed in normal cells, preferentially catalyze monoubiquitination of p53 (Li et al., 2003, supra); interestingly, however, recent studies from Lane's group showed that ARF can block polyubiquitination of p53 but is incapable of inhibiting Mdm2-mediated monoubiquitination of p53 in cells (Xirodimas, D. P., Stephen, C. W., Lane, D. P., Oncogene 20:4972-83, 2001). These studies raise a critical question: how does ARF stabilize p53 in the cells where the levels of Mdm2 are low? Recent studies showing an important role of Pirh2 and COP1 in p53 degradation further support the notion that stabilization of p53 may act through different pathways in vivo (Leng, R. P., Lin, Y., Ma, W., et al., Cell 112:779-91, 2003; Dornan, D. et al., Nature 429: 86-92, 2004).

The present invention has discovered a novel, Mdm2-independent pathway for ARF-mediated activation of p53. The present invention discloses that ARF-BP1 interacts directly with p53 both in vitro and in vivo and catalyzes ubiquitination of p53 in an Mdm2-independent manner. Moreover, ARF-BP1-mediated ubiquitination of p53 is severely inhibited by ARF and inactivation of endogenous ARF-BP1 is critical for ARF-mediated p53 stabilization in Mdm2-null cells. Thus, ARF-mediated p53 stabilization may act through both Mdm2-dependent and Mdm2-independent manners.

Figure 19:
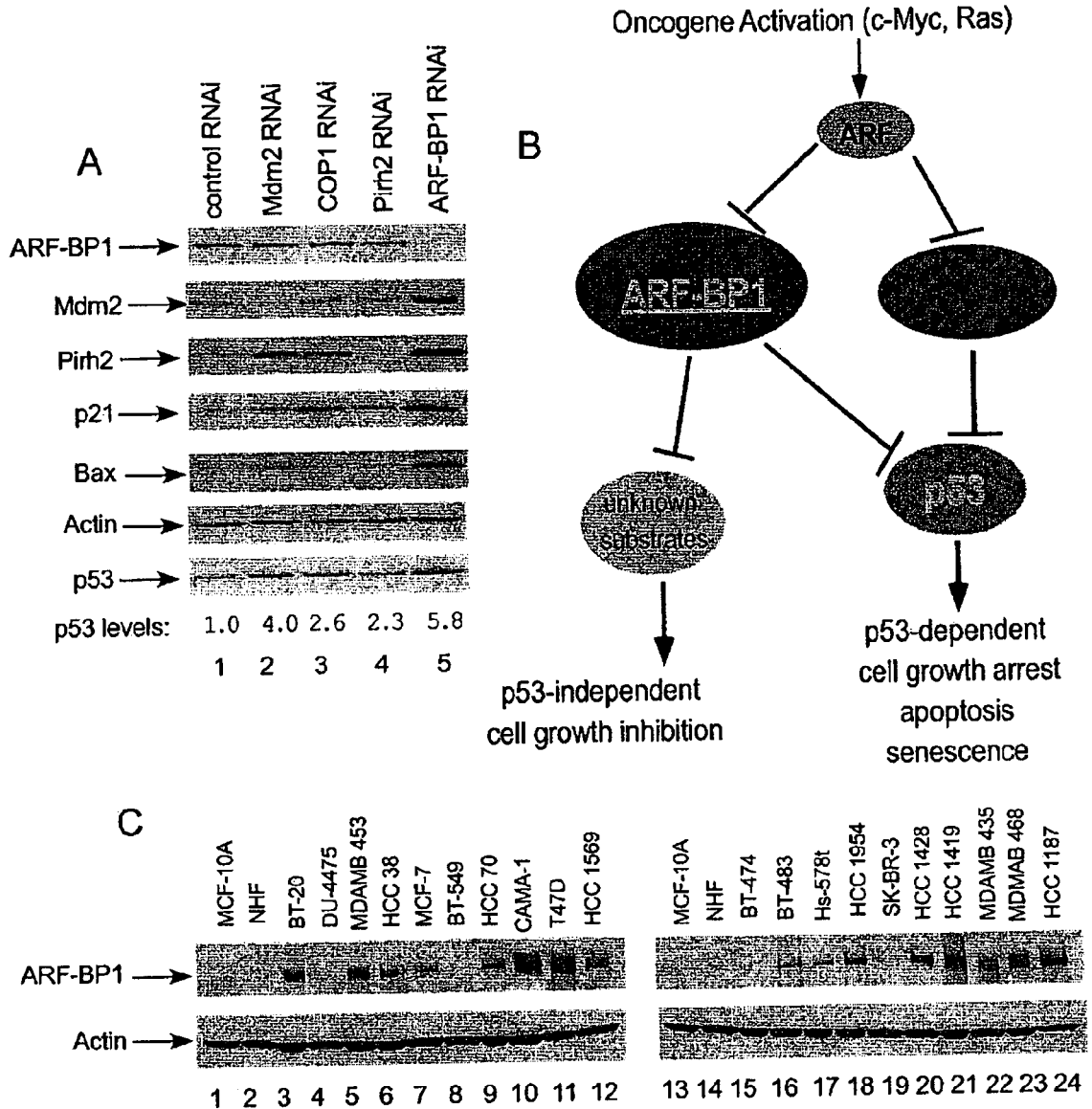
FIGS. 19A-C depict that ARF-BP1 is a critical mediator of ARF tumor suppressor function.
Figure 20:
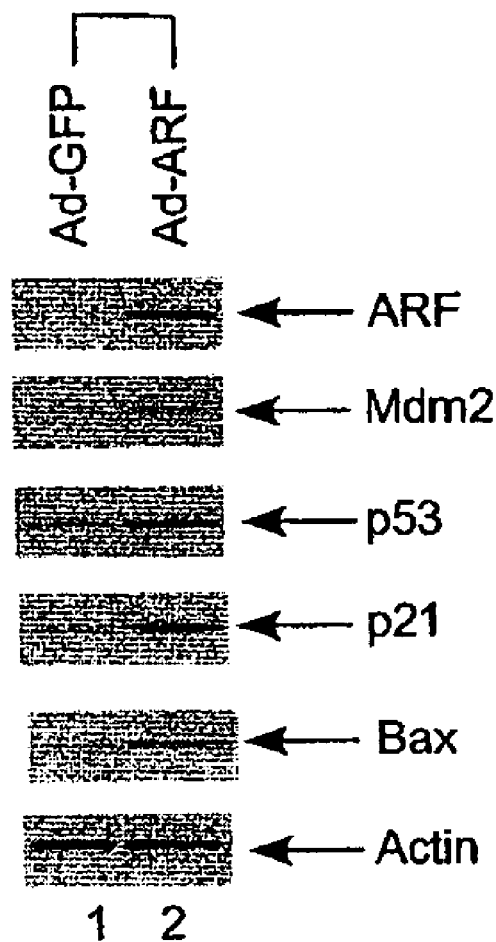
FIG. 20 depicts overexpression of ARF activates p53 and other transcriptional factors (p21, Mdm2, Bax ) via Western blot analysis of cell extracts from U2OS infected with adenovirus-GFP (lanes 1), or adenovirus-ARF (lane 2) with the antibodies against ARF, Mdm2, p53, p21, Bax and actin.

The invention identifies the relationship between ARF-BP1- and Mdm2-mediated regulations on p53 by ARF. Since ARF-BP1 was identified as a major target for ARP through biochemical purification and the interaction between the endogenous ARF-BP1 and ARF proteins is easily detected in normal cells, ARF-mediated p53 activation in normal cells acts, at least in part, though inhibiting ARF-BP1 function in vivo. Thus, ARF-mediated regulation on both ARF-BP1 and Mdm2 may cooperatively control the stability of p53 and more effectively activate p53-mediated functions. For example, when the levels of endogenous Mdm2 are high, p53 may be mainly degraded by Mdm2-mediated polyubiquitination. Thus, the ARF-Mdm2 interaction might be critical for up-regulating p53 activities. In contrast, when the levels of endogenous Mdm2 are low, ARF-mediated regulation of ARF-BP1 may become the key factor to activate p53 (FIG. 19). Several recent studies support the notion that p53 degradation is mediated by both Mdm2-dependent and Mdm2-independent pathways in vivo (Leng et al., 2003, supra; Dornan et al., 2004, supra). By using RNAi knocking down approaches, the differential effects on p53 stabilization by each of known E3 ligases of p53 were evaluated. As expected, inactivation of Mdm2 promoted p53 stabilization while inactivation of either COP1 or Pirh2 also modestly stabilized p53. Notably, inactivation of ARF-BP1 strongly induced p53 stabilization and activated p53-mediated transcription (FIG. 8); the levels of p21 and Bax induction induced by ARF-BP1 RNAi were higher than the levels induced by other types of E3 siRNAs for p53 (FIG. 19A), and very close to the effects by ARF over-expression (FIG. 20). These data indicate that ARF-BP1 is one of the major ubiquitin ligases of p53 in human cells and more importantly, is a key target for ARF-mediated tumor suppressor function.

The existence of two distinct pathways for ARF-mediated p53 activation, one based on the ARF-BP1 ubiquitin ligase and another on the Mdm2 ubiquitin ligase, allows for more versatile control of p53 functions (FIG. 19B) but also raises the question regarding their biological significances. For example, the critical role of Mdm2 in tumorigenesis is well established. Gene amplification and protein overexpression of Mdm2 are found in varies types of tumors (Michael, D., and Oren, M., *Semin Cancer Biol* 13:49-58, 2003). Thus, the ARF-Mdm2 interaction might be particularly important in the cells expressing high levels of Mdm2. Interestingly, the inventor found that ARF-BP1 is highly expressed in 80% (16/20) of breast cancer lines while the expression level of ARF-BP1 in normal breast cells (MCF-10A) is low (FIG. 19C), suggesting a potential role of ARF-BP1 in breast cancer tumorigenesis.

ARF-Mediated Inhibition of ARF-BP1 is Critical for P53-Independent Cell Growth Regulation Although the role of ARF in stabilizing and activating p53 is well accepted, ARF is also found mutated or down-regulated in the tumors that lack functional p53 (Sherr et al., 2001, supra), suggesting that ARF mediated p53-independent function is also critical for its tumor suppression function. Consistent with this notion, a number of studies indicate that ARF can induce p53-independent cell growth repression (Weber, J. D., et al., *Genes Dev.* 14:2358-65, 2000; Rocha, S., Campbell, K. J., Perkins, N. D., *Mol Cell,* 12:15-25, 2003). Based on our observations that ARF-BP1 is the major binding partner of ARF in p53-null cells, the inventor proposes that ARF-BP1 is a critical target for ARF-mediated, p53-independent function. This is supported by the fact that inactivation of ARF-BP1, but not Mdm2, in p53-null cells induces cell growth repression in a manner reminiscent of ARF induction.

The precise mechanism by which ARF-mediated regulation of ARF-BP1 leads to p53-independent cell growth arrest needs future investigation. Since ARF-BP1 is a bona fide ubiquitin ligase, ARP-mediated p53-independent function may act by regulating unidentified substrates of ARF-BP1 (FIG. 19). In the light of recent studies showing that nucleoplasmin/B23 and ribosomal subunits are involved in the regulation of ARF-mediated ribosomal RNA processing (Itahana, K et al., *Mol Cell* 12:1151-64, 2003; Bertwistle, D, Sugimoto, M. Sherr, C. J., *Mol Cell Biol* 24:985-96, 2004), whether ARF-BP1 is directly involved in regulating B23 function or ribosomal RNA processing was examined. The present invention determined that ARF-BP1 interacts with B23 in vivo and in vitro, but does not ubiquitinate and degrade B23 (FIG. 22B). ARF-BP1 did not mediate B23 ubiquitination (FIG. 22C) and ablation of ARF-BP1 did not affect B23 levels. These results indicate that B23 is not the target for ARF-BP1 ubiquitin ligase activity. Moreover, since the ARF pathway is intimately linked with oncogene activation in vivo (Sherr, 2001, supra; Nilsson, J. A. Cleveland, J. L. *Oncogene* 22:9007-21, 2003; Sharpless and Depinho, 2004, supra), the ARF-BP1 and ARF interaction as well as the ubiquitin ligase activity of ARF-BP1 may be regulated upon oncogene activation or other types of stress in the cells.

Potential Implications in Cancer Therapy

Activation of the p53 pathway is a critical and perhaps obligatory step in cancer development. Numerous studies have shown that p53 activation is crucial for the function of many cancer therapeutic agents and that p53-dependent function plays a crucial role in the clinical effectiveness of these agents (Lane and Fisher, *Nature* 427:789-90, 2004; Lowe et al, 1994; Chresta and Hickman, *Nature Medicine* 2:745-6, 1996; Lutzker and Levine, *Cancer Treat Rep,* 87:345-56, 1996). Recent studies on new drug discovery related to p53 also shed light on this matter. For example, the p53 gene therapy was approved for cancer treatment (Surendran, A., *Nature Medicine,* 10:9, 2004). Nutlin, a small molecule the blocks the p53-Mdm2 interaction, was found to effectively kill the tumor cells in vivo by activating the p53 pathway (Vassilev L. T. et al., *Science* 303:844-8, 2004). However, the 53 gene is found mutated in more than 50% of human tumors and many tumor derived p53 point-mutants even have dominant negative effects (Vogelstein et al., *Nature* 408:307-310, 2000). The drugs specifically targeting the p53 pathway may encounter difficulty in killing tumor cells that lack functional p53.

In several aspects, the ARF-BP1 protein is an appropriate candidate target for therapeutic interventions in tumors. Inactivation of ARF-BP1 in the tumor cells expressing wild-type p53, leads to p53 stabilization and activates p53-mediated apoptosis. Importantly, inhibition of ARF-BP1 in the tumor cells that lack functional p53 induces cell growth inhibition. ARF-BP1 is also an enzyme and its ubiquitin ligase activity is critical for its mediated function. Thus, drug screening for inhibitors of its enzymatic activity will be a promising strategy for therapeutic interventions in tumors. In contrast to targeting the proteins specifically inhibiting p53 function such as Mdm2, inhibitors of ARF-BP1 should be effective in preventing tumor cells growth regardless of p53 status.

In view of the foregoing, the present invention provides a method for determining whether a subject has neoplasia. As used herein, the "subject" is a mammal, including, without limitation, a cow, dog, human, monkey, mouse, pig, or rat. Preferably, the subject is a human. The inventor has demonstrated herein (see, e.g., FIGS. 16A-D) the detection of significant enhancement of ARF-BP1 interaction, and enhanced ARF-BP1 expression, in cells subjected to DNA damage, as compared with normal (undamaged) cells. Accordingly, the method of the present invention comprises assaying a diagnostic sample of the subject for expression of ARF-BP1, wherein detection of ARF-BP1 expression elevated above normal is diagnostic of neoplasia in the subject.

As used herein, "ARF-BP1" includes both a ARF-BP1 protein and an ARF-BP1 analogue, including "conservative substitutions". Unless otherwise indicated, "protein" shall include a protein, protein domain, polypeptide, or peptide. As further used herein, the ARF-BP1 protein has the amino acid sequence set forth in FIG. 3 (SEQ ID NO: 2).

A "ARF-BP1 analogue", as used herein, is a functional variant of the ARF-BP1 protein, having ARF-BP1 biological activity, that has 60% or greater (preferably, 70% or greater) amino-acid-sequence homology with the ARF-BP1 protein. An ARF-BP1 "analogue" includes a variant of the ARF-BP1 protein that has a homologous three-dimensional conformation. ARF-BP1 and ARF-BP1 analogues may be produced synthetically or recombinantly, or may be isolated from native cells. ARF-BP1 is preferably produced recombinantly, using conventional techniques and cDNA encoding ARF-BP1 (SEQ ID NO:1).

As used herein, "conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The term "conservative substitutions", as defined herein, includes substitutions having an inconsequential effect on the ability of ARF-BP1 to interact with p53, particularly in respect of the use of said interaction for the identification and design of p53 inhibitors, for molecular replacement analyses, and/or for homology modeling.

The method of the present invention may be used to determine whether a subject has neoplasia, thereby permitting the diagnosis of such neoplasia in the subject. As used herein, "neoplasia" refers to the uncontrolled and progressive multiplication of cells of a neoplasm (i.e., neoplastic cells, such as tumor cells), under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of neoplastic cells having the unique trait of loss of normal controls, resulting in unregulated growth, lack of differentiation, local tissue invasion, and/or metastasis.

As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors (e.g., breast tumors) that are either invasive or noninvasive. Malignant neoplasms are distinguished from benign in that the former show a greater degree of anaplasia, or loss of differentiation and orientation of cells, and have the properties of invasion and metastasis. Examples of neoplasms or neoplasias which may be assessed, detected, diagnosed, monitored, or treated in accordance with inventions described herein include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease (Beers and Berkow (eds.), The Merck Manual of Diagnosis and Therapy, 17th ed. (Whitehouse Station, N.J.: Merck Research Laboratories, 1999) 973-74, 976, 986, 988, 991).

As indicated above, over 50% of all cancer cases are associated with p53 mutations. Accordingly, in one embodiment of the present invention, the methods and compositions of the present invention are directed to the assessment, detection, diagnosis, monitoring, and treatment of p53-associated neoplasias, including neoplasias associated with a defect in the p53 pathway. In another embodiment of the present invention, the methods and compositions of the present invention are directed to the assessment, detection, diagnosis, monitoring, and treatment of breast cancer, colon cancer, leukemia, lung cancer, malignant melanoma, ovarian cancer, or prostate cancer.

In another embodiment of the present invention, the methods and compositions of the present invention are directed to the assessment, detection, diagnosis, monitoring, and treatment of p53-independent neoplasias, including neoplasias not associated with a defect in the p53 pathway. In another embodiment of the present invention, the methods and compositions of the present invention are directed to the assessment, detection, diagnosis, monitoring, and treatment of breast cancer, colon cancer, leukemia, lung cancer, malignant melanoma, ovarian cancer, or prostate cancer.

According to the method of the present invention, the diagnostic sample of a subject may be assayed in vitro or in vivo. Where the assay is performed in vitro, a diagnostic sample from the subject may be removed using standard procedures. The diagnostic sample may be tissue, including any bone, brain tissue, breast tissue, colon tissue, muscle tissue, nervous tissue, ovarian tissue, prostate tissue, retinal tissue, skin tissue, or soft tissue, which may be removed by standard biopsy. In addition, the diagnostic sample may be a bodily fluid, including cerebrospinal fluid, pericardial fluid, peritoneal fluid, saliva, serum, and urine. Furthermore, the diagnostic sample taken from the subject or patient may be, for example, any tissue known to have a neoplasm, any tissue suspected of having a neoplasm, or any tissue believed not to have a neoplasm.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (e.g., with an antibody to ARF-BP1), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, neoplasia in a subject may be diagnosed by assaying a diagnostic sample of the subject for expression of ARF-BP1, wherein expression of ARF-BP1 elevated above normal is diagnostic of neoplasia. As used herein, "expression" means the transcription of a gene into at least one mRNA transcript, or the translation of at least one mRNA into a protein. For example, "expression of ARF-BP1" means the transcription of the ARF-BP1 gene into at least one mRNA transcript, or the translation of at least one mRNA into a ARF-BP1 protein, as defined above. Accordingly, a diagnostic sample may be assayed for ARF-BP1 expression by assaying for ARF-BP1 protein, ARF-BP1 cDNA, or ARF-BP1 mRNA. The appropriate form of ARF-BP1 will be apparent based on the particular techniques discussed herein.

Furthermore, it is contemplated that the diagnostic sample may be assayed for expression of any or all forms of ARF-BP1 protein (including precursor, endoproteolytically-processed forms, and other forms resulting from post-translational modification) in order to determine whether a subject or patient has neoplasia. It is also contemplated that the diagnostic sample may be assayed for expression of ARF-BP1 elevated above normal by detecting an increase in p53-ARF-BP1 interaction, as disclosed herein. Accordingly, in one embodiment of the present invention, ARF-BP1 expression elevated above normal is detected by detecting p53-ARF-BP1 interaction elevated above normal.

As used herein, the term "elevated above normal" refers to detection (e.g., of expression of ARF-BP1, of p53-ARF-BP1 interaction, of ARF-BP1-ARF interaction, etc.) at a level that is significantly greater than the level expected for the same type of diagnostic sample taken from a nondiseased subject or patient (i.e., one who does not have neoplasia) of the same gender and of similar age. As further used herein, "significantly greater" means that the difference between the level (e.g., of expression of ARF-BP1, of p53-ARF-BP1 interaction, of ARF-BP1-ARF interaction, etc.) that is elevated above normal, and the expected (normal) level (e.g., of expression of ARF-BP1, of p53-ARF-BP1 interaction, etc.), is of statistical significance.

Preferably, ARF-BP1 expression (or p53-ARF-BP1 interaction) elevated above normal is expression of ARF-BP1 (or p53-ARF-BP1 interaction) at a level that is at least 10% greater than the level of ARF-BP1 expression (or p53-ARF-BP1 interaction) otherwise expected. Where ARF-BP1 expression (or p53-ARF-BP1 interaction) is expected to be absent from a particular diagnostic sample taken from a particular subject or patient, the normal level of ARF-BP1 expression (or p53-ARF-BP1 interaction) for that subject or patient is nil. Where a particular diagnostic sample taken from a particular subject or patient is expected to have a low level of constitutive ARF-BP1 expression (or p53-ARF-BP1 interaction), that low level is the normal level of ARF-BP1 expression (or p53-ARF-BP1 interaction) for that subject or patient.

Expected or normal levels of ARF-BP1 expression for a particular diagnostic sample taken from a subject or patient may be easily determined by assaying nondiseased subjects of a similar age and of the same gender. For example, diagnostic samples may be obtained from at least 30 normal, healthy men between the ages of 25 and 80, to determine the normal quantity of ARF-BP1 expression in males. A similar procedure may be followed to determine the normal quantity of ARF-BP1 expression in females. Once the necessary or desired samples have been obtained, the normal quantities of ARF-BP1 expression in men and women may be determined using a standard assay for quantification, such as flow cytometry, Western-blot analysis, or an ELISA for measuring protein quantities, as described below. For example, an ELISA may be run on each sample in duplicate, and the means and standard deviations of the quantity of the ARF-BP1 protein may be determined. If necessary, additional subjects may be recruited before the normal quantities of ARF-BP1 expression are quantified. A similar type of procedure may be used to determine expected or normal levels of p53-ARF-BP1 interaction for a particular diagnostic sample taken from a subject or patient.

In accordance with the method of the present invention, a diagnostic sample of a subject may be assayed for ARF-BP1 expression (or p53-ARF-BP1 interaction), and ARF-BP1 expression (or p53-ARF-BP1 interaction) may be detected in a diagnostic sample, using assays and detection methods readily determined from the known art (e.g., immunological techniques, hybridization analysis, fluorescence imaging techniques, and/or radiation detection, etc.), as well as any assays and detection methods disclosed herein (e.g., immunoprecipitation, Western-blot analysis, etc.). For example, a diagnostic sample of a subject may be assayed for ARF-BP1 expression using an inhibitor of ARF-BP1. As used herein, "inhibitor" means the agent has affinity for, binds to, inhibits or is directed against a target of interest (e.g., ARF-BP1). As further used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. Preferably, the agent of the present invention is labeled with a detectable marker or label.

In one embodiment of the present invention, the inhibitor of ARF-BP1 is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified protein (e.g., ARF-BP1). Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation, such as $^{35}$S, $^{32}$P, $^{125}$I, $^3$H, or $^{14}$C. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody (e.g., α-ARF-BP1) labeled with a detectable marker or label.

Where the agent of the present invention is an antibody reactive with ARF-BP1, a diagnostic sample taken from the subject may be purified by passage through an affinity column which contains ARF-BP1 antibody (e.g., α-ARF-BP1) as a ligand attached to a solid support, such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The ARF-BP1 antibody (e.g., α-ARF- BP1) may be further attached to the solid support through a spacer molecule, if desired. Appropriate binding conditions (e.g., temperature, pH, and salt concentration) for ensuring binding of the agent and the antibody may be readily determined by the skilled artisan. In a preferred embodiment, the ARF-BP1 antibody (e.g., α-ARF-BP1) is attached to a sepharose column, such as Sepharose 4B.

Where the agent is an antibody, a diagnostic sample of the subject may be assayed for ARF-BP1 expression using binding studies that utilize one or more antibodies immunoreactive with ARF-BP1, along with standard immunological detection techniques. For example, the ARF-BP1 protein eluted from the affinity column may be subjected to an ELISA assay, Western-blot analysis, flow cytometry, or any other immunostaining method employing an antigen-antibody interaction. Preferably, the diagnostic sample is assayed for ARF-BP1 expression using Western blotting.

Alternatively, a diagnostic sample of a subject may be assayed for ARF-BP1 expression using hybridization analysis of nucleic acid extracted from the diagnostic sample taken from the subject. According to this method of the present invention, the hybridization analysis may be conducted using Northern-blot analysis of mRNA. This method also may be conducted by performing a Southern-blot analysis of DNA using one or more nucleic acid probes, which hybridize to nucleic acid encoding ARF-BP1. The nucleic acid probes may be prepared by a variety of techniques known to those skilled in the art, including, without limitation, the following: restriction enzyme digestion of ARF-BP1 nucleic acid; and automated synthesis of oligonucleotides having sequences which correspond to selected portions of the nucleotide sequence of the ARF-BP1 nucleic acid, using commercially-available oligonucleotide synthesizers, such as the Applied Biosystems Model 392 DNA/RNA synthesizer.

The detection of ARF-BP1 expression (or p53-ARF-BP1 or ARF-BP1-ARF interactions) in the method of the present invention may be followed by an assay to measure or quantify the extent of ARF-BP1 expression in a diagnostic sample of a subject. Such assays are well known to one of skill in the art, and may include immunohistochemistry/immunocytochemistry, flow cytometry, mass spectroscopy, Western-blot analysis, or an ELISA for measuring amounts of ARF-BP1 protein. For example, to use an immunohistochemistry assay, histological (paraffin-embedded) sections of tissue may be placed on slides, and then incubated with an antibody against ARF-BP1. The slides then may be incubated with a second antibody (against the primary antibody), which is tagged to a dye or other calorimetric system (e.g., a fluorochrome, a radioactive agent, or an agent having high electron-scanning capacity), to permit visualization of ARF-BP1 that is present in the sections.

It is contemplated that the diagnostic sample in the present invention frequently will be assayed for ARF-BP1 expression (or p53-ARF-BP1 interaction) not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for ARF-BP1 expression.

Similarly, the present invention provides a method for determining whether a subject has neoplasia, by assaying a diagnostic sample of the subject for ARF-BP1 expression, wherein detection of ARF-BP1 expression elevated above normal in the diagnostic sample is diagnostic of neoplasia in the subject. As discussed above, cancer has been associated with defects in the p53 pathway, including defects in ARF-BP1, Mdm2, and/or p53. Accordingly, in one embodiment, the methods and compositions of the present invention are directed to the assessment, detection, diagnosis, monitoring, and treatment of p53-associated neoplasias. In another embodiment, the methods and compositions of the present invention are directed to the assessment, detection, diagnosis, monitoring, and treatment of p-53 independent neoplasias.

In accordance with the method of the present invention, a diagnostic sample may be assayed for ARF-BP1 expression by assaying for ARF-BP1 protein, ARF-BP1 cDNA, or ARF-BP1 mRNA, as described above. Expected or normal levels of ARF-BP1 expression for a particular diagnostic sample taken from a subject or patient may be easily determined by assaying nondiseased subjects of a similar age and of the same gender, as described above in connection with ARF-BP1.

It is contemplated that the diagnostic sample may be assayed for expression of any or all forms of ARF-BP1 proteins (including precursor, endoproteolytically-processed forms, and other forms resulting from post-translational modification) in order to determine whether a subject or patient has neoplasia. It is also contemplated that the diagnostic sample may be assayed for expression of p53 elevated above normal and ARF-BP1 elevated above normal by detecting an increase in p53-ARF-BP1 interaction. Accordingly, in one embodiment of the present invention, expression of p53 elevated above normal and expression of ARF-BP1 elevated above normal are detected in the diagnostic sample by detecting p53-ARF-BP1 interaction elevated above normal in the diagnostic sample. It is also contemplated that the diagnostic sample may be assayed for expression of ARF decreased below normal and ARF-BP1 elevated above normal by detecting an increase in ARF-ARF-BP1 interaction. Accordingly, in one embodiment of the present invention, expression of p53 elevated above normal and expression of ARF-BP1 elevated above normal are detected in the diagnostic sample by detecting p53-ARF-BP1 interaction elevated above normal in the diagnostic sample. In another embodiment of the present invention, expression of ARF below normal and expression of ARF-BP1 elevated above normal are detected in the diagnostic sample by detecting ARF-ARF-BP1 interaction elevated above normal in the diagnostic sample.

A diagnostic sample of a subject may be assayed for ARF, ARF-BP1 expression, and/or p53-ARF-BP1 interaction in accordance with methods described herein. p53 expression, ARF-BP1 expression, and/or ARF-ARF-BP1 interaction may also be detected in a diagnostic sample using assays and detection methods readily determined from the known art, as well as any assays and detection methods disclosed herein.

For example, a diagnostic sample of a subject may be assayed for ARF-BP1 expression using hybridization analysis of nucleic acid extracted from the diagnostic sample taken from the subject. This method preferably utilizes a nucleic acid probe which hybridizes to nucleic acid encoding ARF-BP1. In one embodiment, the nucleic acid probe is labeled with a detectable marker or label. In the alternative, a diagnostic sample of a subject may be assayed for ARF-BP1 expression using an agent reactive with ARF-BP1. Preferably, the agent of the present invention is labeled with a detectable marker or label. In one embodiment of the present invention, the agent reactive with ARF-BP1 is an antibody (e.g., anti-ARF-BP1 monoclonal antibody).

When the agent of the present invention is an antibody reactive with ARF-BP1, a diagnostic sample taken from the subject may be purified by passage through an affinity column which contains anti-ARF-BP1 antibody as a ligand attached to a solid support, such as an insoluble organic polymer in the form of a bead, gel, or plate, in accordance with techniques described above for detecting ARF-BP1. Additionally, where the agent is an anti-ARF-BP1 antibody, a diagnostic sample of the subject may be assayed for ARF-BP1 expression using binding studies that utilize one or more antibodies immunoreactive with ARF-BP1, along with standard immunological detection techniques, as described herein in connection with ARF-BP1.

The detection of ARF-BP1 expression, and/or ARF-ARF-BP1 interaction, and/or p53-ARF-BP1 interaction in the method of the present invention may be followed by an assay to measure or quantify the extent of ARF-BP1 expression, and/or ARF-ARF-BP1 or p53-ARF-BP1 interaction in the diagnostic sample of a subject. Additionally, the method of the present invention may further comprise the step of providing to a subject's or patient's consulting physician a report of the results obtained upon assaying a diagnostic sample of the subject or patient for ARF-BP1 expression, ARF-ARF-BP1 interaction, and/or p53-ARF-BP1 interaction.

The present invention further provides a method for assessing the efficacy of therapy to treat neoplasia in a subject or patient who has undergone or is undergoing treatment for neoplasia. The method of the present invention comprises assaying a diagnostic sample of the subject or patient for ARF-BP1 expression, wherein detection of a normal level of ARF-BP1 expression is indicative of successful therapy to treat neoplasia, and detection of ARF-BP1 expression elevated above normal is indicative of a need to continue therapy to treat neoplasia. In one embodiment of the present invention, ARF-BP1 expression elevated above normal is detected by detecting p53-ARF-BP1 or ARF-ARF-BP1 interactions elevated above normal. The neoplasia may be any of those described above, including p53-dependent and p53-independent neoplasias. The diagnostic sample may be a tissue or a bodily fluid, as described above, and may be assayed for expression of ARF-BP1 (or p53-ARF-BP1 and/or ARF-ARF-BP1 interaction) in vitro or in vivo. In addition, the diagnostic sample may be assayed for expression of ARF-BP1 (or p53-ARF-BP1 interaction and/or ARF-ARF-BP1 interaction) using all of the various assays and methods of detection and quantification described above. This method of the present invention provides a means for monitoring the effectiveness of therapy to treat neoplasia by permitting the periodic assessment of levels of ARF-BP1 expression (or p53-ARF-BP1 interaction and/or ARF-ARF-BP1 interaction) in a diagnostic sample taken from a subject or patient.

According to the method of the present invention, a diagnostic sample of a subject or patient may be assayed, and levels of ARF-BP1 expression (or p53-ARF-BP1 interaction and/or ARF-ARF-BP1 interaction) may be assessed, at any time following the initiation of therapy to treat neoplasia. For example, levels of ARF-BP1 expression (or p53-ARF-BP1 interaction and/or ARF-ARF-BP1 interaction) may be assessed while the subject or patient is still undergoing treatment for neoplasia. Where levels of ARF-BP1 expression (or p53-ARF-BP1 interaction and/or ARF-ARF-BP1 interaction) detected in an assayed diagnostic sample of the subject or patient continue to remain elevated above normal, a physician may choose to continue with the subject's or patient's treatment for the neoplasia. Where levels of ARF-BP1 expression (or p53-ARF-BP1 interaction and/or ARF-ARF-BP1 interaction) in an assayed diagnostic sample of the subject or patient decrease through successive assessments, it may be an indication that the treatment for neoplasia is working, and that treatment doses could be decreased or even ceased. Where levels of ARF-BP1 expression (or p53-ARF-BP1 interaction and/or ARF-ARF-BP1 interaction) in an assayed diagnostic sample of the subject or patient do not rapidly decrease through successive assessments, it may be an indication that the treatment for neoplasia is not working, and that treatment doses could be increased. Where ARF-BP1 expression (or p53-ARF-BP1 interaction and/or ARF-ARF-BP1 interaction) is no longer detected in an assayed diagnostic sample of a subject or patient at levels elevated above normal, a physician may conclude that the treatment for neoplasia has been successful, and that such treatment may cease.

It is within the confines of the present invention to assess levels of ARF-BP1 expression following completion of a subject's or patient's treatment for neoplasia, in order to determine whether the neoplasia has recurred in the subject or patient. Accordingly, an assessment of levels of ARF-BP1 expression (or p53-ARF-BP1 interaction and/or ARF-ARF-BP1 interaction) in an assayed diagnostic sample may provide a convenient way to conduct follow-ups of patients who have been diagnosed with neoplasias. Furthermore, it is within the confines of the present invention to use assessed levels of ARF-BP1 expression (or p53-ARF-BP1 interaction and/or ARF-ARF-BP1 interaction) in an assayed diagnostic sample as a clinical or pathologic staging tool, as a means of determining the extent of neoplasia in the subject or patient, and as a means of ascertaining appropriate treatment options.

The present invention also provides a method for assessing the efficacy of therapy to treat neoplasia in a subject who has undergone or is undergoing treatment for neoplasia, by assaying a diagnostic sample of the subject for ARF-BP1 expression and ARF-BP1 expression, wherein detection of normal ARF-BP1 expression in the diagnostic sample is indicative of successful therapy to treat neoplasia, and detection of ARF-BP1 expression elevated above normal in the diagnostic sample is indicative of a need to continue therapy to treat neoplasia. In one embodiment of the present invention, ARF-BP1 expression elevated above normal are detected in the diagnostic sample by detecting p53-ARF-BP1 interaction elevated above normal in the diagnostic sample. The neoplasia may be any of those described above, including p53-dependent and p-53 independent neoplasias. Suitable diagnostic samples, assays, and detection and quantification methods for use in the method of the present invention have already been described.

A correlation exists, in general, between tumor burden and the survival of a patient who has cancer. Therefore, it is also contemplated in the present invention that assaying a diagnostic sample of a subject for ARF-BP1 expression may be a useful means of providing information concerning the prognosis of a subject or patient who has neoplasia. Accordingly, the present invention further provides a method for assessing the prognosis of a subject who has neoplasia, comprising assaying a diagnostic sample of the subject for ARF-BP1 expression, wherein the subject's prognosis improves with a decrease in ARF-BP1 expression in the diagnostic sample of the subject, and the subject's prognosis worsens with an increase in ARF-BP1 expression in the diagnostic sample of the subject. In one embodiment of the present invention, ARF-BP1 expression elevated above normal is detected by detecting p53-ARF-BP1 interaction elevated above normal. Suitable diagnostic samples, assays, and detection and quantification methods for use in the method of the present invention have already been described. This method of the present invention provides a means for determining the prognosis of a subject or patient diagnosed with neoplasia based upon the level of ARF-BP1 expression (or p53-ARF-BP1 interaction and/or ARF-ARF-BP1 interaction) in an assayed diagnostic sample of the subject or patient.

According to the method of the present invention, a diagnostic sample of a subject or patient may be assayed, and levels of ARF-BP1 expression (or p53-ARF-BP1 interaction and/or ARF-ARF-BP1 interaction) may be assessed, at any time during or following the diagnosis of neoplasia in the subject or patient. For example, levels of ARF-BP1 expression (or p53-ARF-BP1 interaction and/or ARF-ARF-BP1 interaction) in an assayed diagnostic sample may be assessed before the subject or patient undergoes treatment for neoplasia, in order to determine the subject's or patient's initial prognosis. Additionally, levels of ARF-BP1 expression (or p53-ARF-BP1 interaction and/or ARF-ARF-BP1 interaction) in an assayed diagnostic sample may be assessed while the subject or patient is undergoing treatment for neoplasia, in order to determine whether the subject's or patient's prognosis has become more or less favorable through the course of treatment.

By way of example, where levels of ARF-BP1 expression (or p53-ARF-BP1 interaction and/or ARF-ARF-BP1 interaction) detected in an assayed diagnostic sample of the subject or patient are, or continue to remain, significantly high, a physician may conclude that the subject's or patient's prognosis is unfavorable. Where ARF-BP1 expression (or p53-ARF-BP1 interaction and/or ARF-ARF-BP1 interaction) in an assayed diagnostic sample of the subject or patient decreases through successive assessments, it may be an indication that the subject's or patient's prognosis is improving. Where levels of ARF-BP1 expression (or p53-ARF-BP1 interaction and/or ARF-ARF-BP1 interaction) in an assayed diagnostic sample of the subject or patient do not decrease significantly through successive assessments, it may be an indication that the subject's or patient's prognosis is not improving. Finally, where ARF-BP1 expression (or p53-ARF-BP1 interaction and/or ARF-ARF-BP1 interaction) is low, or is normal, in a diagnostic sample of the subject or patient, a physician may conclude that the subject's or patient's prognosis is favorable.

The discovery that ARF-BP1 can be detected in cells displaying neoplasias provides a means of identifying patients with neoplasias, and presents the potential for commercial application in the form of a test for the diagnosis of neoplasias. The development of such a test could provide general screening procedures. Such procedures can assist in the early detection and diagnosis of neoplasia, or preneoplasia or genetic predisposition to neoplasia and can provide a method for the follow-up of patients in whom ARF-BP1 expression (including p53-ARF-BP1 interaction and/or ARF-ARF-BP1 interaction) elevated above normal have been detected.

Accordingly, the present invention further provides a kit for use as an assay of neoplasia, comprising an agent reactive with ARF-BP1 and reagents suitable for detecting expression of ARF-BP1 (and p53-ARF-BP1 interaction and/or ARF-ARF-BP1 interaction). The present invention also provides a kit for use in detecting neoplasia, comprising: (a) at least one agent reactive with ARF-BP1; and (b) reagents suitable for detecting expression of ARF-BP1. The agents may be any of those described above, and may be used in any of the above-described assays or methods for detecting or quantifying ARF-BP1 expression, p53-ARF-BP1 interaction, and ARF-ARF-BP1 interaction. Preferably, at least one agent of the present invention is labeled with a detectable marker or label.

As indicated above, over 50% of all cancer cases are associated with p53 mutations. Therefore, p53 is the key for treating many cancers, and the p53 pathway is a particular focus of interest. p53 is generally not a stable protein; it has a half-life of approximately 20 min, and is degraded very rapidly by proteosomes in the protein-degradation pathway following ubiquitination (the binding of ubiquitin). It is believed that the stabilization of p53 is important for the protein's efficiency as a tumor suppressor.

It is expected that some cancers associated with defects in the p53 pathway result not from a defect in p53, but from a mutated ARF-BP1 (e.g., a mutation resulting from a genetic alteration at the coding region) and/or a defect in ARF-BP1 regulation at the expression level (e.g., a defect resulting from a genetic alteration at the promoter region of the ARF-BP1 gene). In view of the foregoing, it is clear that modulation of the levels of ARF-BP1 in cells provides a means for enhancing p53's tumor-suppressor function, and for supplementing this function with ARF-BP1's own tumor-suppressor activity. Accordingly, the present invention further provides a method for treating neoplasia in a subject in need of treatment therefore, comprising decreasing activity of ARF-BP1 in the subject. The neoplasia may be any of those described above, including p53 independent and p53-dependent neoplasia.

In accordance with the method of the present invention, activity of ARF-BP1 in a subject may be decreased by targeting ARF-BP1 directly. Additionally, activity of ARF-BP1 in a subject may be decreased indirectly, by targeting an enzyme or other endogenous molecule that regulates or modulates the functions or levels of ARF-BP1 in the subject. Preferably, ARF-BP1 activity in the subject is decreased by at least 10% in the method of the present invention. More preferably, ARF-BP1 activity is decreased by at least 20%.

For example, activity of ARF-BP1 in a subject may be decreased by directly or indirectly deactivating, inhibiting, binding or neutralizing one or more functions of ARF-BP1 in the subject (e.g., by the modulation or regulation of proteins that interact with ARF-BP1). The term "inhibiting", as used herein, means decreasing or negating the functions of ARF-BP1 in the subject, particularly the ubiquitination, and resulting destabilization, of p53. In the method of the present invention, ARF-BP1 in a subject may be inhibited, for example, by administering to the subject a small molecule or protein mimetic that inhibits ARF-BP1 or that is reactive with ARF-BP1, as defined above.

Activity of ARF-BP1 in a subject also may be decreased by directly or indirectly prohibiting, suppressing, or inhibiting the upregulation of ARF-BP1 expression within a subject. Accordingly, in one embodiment of the present invention, activity of ARF-BP1 is decreased in a subject by administering to the subject an inhibitor of ARF-BP1 expression in an amount effective to treat the neoplasia in the subject. As used herein, a "inhibitor of expression" may be any agent or combination of agents that that has an antagonistic (inhibitory) or agonistic (facilitatory) effect on expression of a specified protein. Thus, a modulator of expression may be an agonist or an antagonist. The modulators of the present invention include any protein, polypeptide, peptide, nucleic acid (including DNA or RNA), antibody, Fab fragment, F(ab')$_2$ fragment, molecule, compound, antibiotic, and drug, and an agent reactive with a protein of interest (e.g., ARF-BP1) that inhibits or downregulates expression of that protein.

Inhibitors of ARF-BP1 may be identified using a simple screening assay. For example, to screen for candidate inhibitors of ARF-BP1, human lung carcinoma cells (H1299) may be plated onto microtiter plates, then contacted with a library of drugs. Any resulting decrease in, or down regulation of, ARF-BP1 expression then may be detected using nucleic acid hybridization and/or immunological techniques known in the art, including an ELISA. Additional inhibitors of ARF-BP1 expression may be identified using screening procedures well known in the art or disclosed herein. Inhibitors of ARF-BP1 will be those drugs which prevent or downregulate expression of ARF-BP1. In this manner, candidate inhibitors also may be screened for their ability to inhibit proliferation of neoplasms using ARF-BP1 expression as an indicator that cell division or growth of cells in a neoplasm is decreasing in rate, or has stopped.

It is within the confines of the present invention that the inhibitor of ARF-BP1 expression may be linked to another agent, or administered in combination with another agent, such as an antineoplastic drug or a ribozyme, in order to increase the effectiveness of the treatment of neoplasia, increase the efficacy of targeting, and/or increase the efficacy of p53 deubiquitination. Examples of antineoplastic drugs to which the inhibitor of ARF-BP1 expression may be linked include, without limitation, carboplatin, cyclophosphamide, doxorubicin, etoposide, and vincristine.

Activity of ARF-BP1 in a subject also may be decreased in a subject by directly or indirectly decreasing levels of ARF-BP1 in vivo within the subject. By way of example, the level of ARF-BP1 in a subject may be decreased by administering a ARF-BP1 binding-protein to the subject, in an amount effective to treat neoplasia in the subject.

In accordance with the method of the present invention, ARF-BP1 inhibitors may be administered to a subject who has neoplasia, either alone or in combination with one or more antineoplastic drugs used to treat neoplasias. Examples of antineoplastic drugs with which the ARF-BP1 binding protein may be combined include, without limitation, carboplatin, cyclophosphamide, doxorubicin, etoposide, and vincristine.

In the method of the present invention, an inhibitor of ARF-BP1 expression, a ARF-BP1 protein, or a nucleic acid sequence encoding ARF-BP1 is administered to a subject who has neoplasia in an amount effective to treat the neoplasia in the subject. As used herein, the phrase "effective to treat the neoplasia" means effective to ameliorate or minimize the clinical impairment or symptoms resulting from the neoplasia. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasia; or by limiting, suspending, terminating, or otherwise controlling the maturation and proliferation of cells in the neoplasm. The amount of inhibitor of ARF-BP1 expression, ARF-BP1 protein, or nucleic acid encoding ARF-BP1 that is effective to treat neoplasia in a subject will vary depending on the particular factors of each case, including the type of neoplasia, the stage of neoplasia, the subject's weight, the severity of the subject's condition, and the method of administration. These amounts can be readily determined by the skilled artisan.

In the method of the present invention, the inhibitor of ARF-BP1 expression, the ARF-BP1 protein, or the nucleic acid sequence encoding ARF-BP1 may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. One preferred method of administration is parenteral administration, by intravenous or subcutaneous injection.

For oral administration, the formulation of the ARF-BP1 inhibitor, protein, or nucleic acid may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the ARF-BP1 inhibitor, protein, or nucleic acid may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampules or vials. The formulation also may be delivered by any mode of injection, including any of those described above.

For transdermal administration, the ARF-BP1 inhibitor, protein, or nucleic acid may be combined with skin penetration enhancers, such as propylene glycol, polyethylene glycol, isopropanol, ethanol, oleic acid, N-methylpyrrolidone, and the like, which increase the permeability of the skin to the modulator, protein, or nucleic acid, and permit the modulator, protein or nucleic acid to penetrate through the skin and into the bloodstream. The composition of enhancer and modulator, protein, or nucleic acid also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The inhibitor, protein, or nucleic acid may be administered transdermally, at or near the site on the subject where the neoplasm is localized. Alternatively, the inhibitor, protein, or nucleic acid may be administered transdermally at a site other than the affected area, in order to achieve systemic administration.

The ARF-BP1 inhibitor, protein, or nucleic acid of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the inhibitor, protein, or nucleic acid.

In the method of the present invention, where the inhibitor of ARF-BP1 expression is a protein, or where ARF-BP1 protein is the therapeutic of choice, the protein also may be administered or introduced to the subject by introducing into a sufficient number of cells of the subject a nucleic acid encoding the protein, in a manner permitting expression of the protein in the subject. The amount of nucleic acid encoding the therapeutic protein is an amount that will produce the protein in an amount effective to treat neoplasia, as defined above, in the subject. This amount may be readily determined by the skilled artisan.

Nucleic acid encoding the inhibitor of ARF-BP1 expression, or the ARF-BP1 protein, as well as any nucleotide modulators of ARF-BP1 expression, all may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of such viruses as retrovirus, HSV, adenovirus, adeno-associated virus, Semiliki Forest virus, cytomegalovirus, and vaccinia virus.

It is within the confines of the present invention that a nucleic acid encoding an inhibitor of ARF-BP1 expression, or encoding the ARF-BP1 protein itself, may be introduced into suitable cells in vitro, using conventional procedures, to achieve expression of the therapeutic protein in the cells. Cells expressing the inhibitor of ARF-BP1 expression, or the ARF-BP1 protein, then may be introduced into a subject to treat neoplasia in vivo. In such an ex vivo gene therapy approach, the cells are preferably removed from the subject, subjected to DNA techniques to incorporate nucleic acid encoding the therapeutic protein, and then reintroduced into the subject.

It is also within the confines of the present invention that a formulation containing a ARF-BP1 inhibitor, protein, or nucleic acid may be further associated with a pharmaceutically-acceptable carrier, thereby comprising a pharmaceutical composition. Accordingly, the present invention further provides a pharmaceutical composition, comprising an inhibitor of ARF-BP1 expression, or a ARF-BP1 protein or a nucleic acid sequence encoding ARF-BP1, and a pharmaceutically-acceptable carrier. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical arts. For example, the ARF-BP1 inhibitor, protein, or nucleic acid may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the ARF-BP1 inhibitor, protein, or nucleic acid of the present invention to a subject to treat neoplasia. The ARF-BP1 inhibitor, protein, or nucleic acid is provided in an amount that is effective to treat neoplasia in a subject to whom the pharmaceutical composition is administered. That amount may be readily determined by the skilled artisan, as described above.

The present invention further provides a method for treating neoplasia in a subject, by increasing or enhancing activity of p53 in the subject, wherein activity of p53 is increased or enhanced in the subject by inhibiting ARF-ARF-BP1 or p53-ARF-BP1 interaction in the subject. Preferably, p53 activity in the subject is increased or enhanced by at least 10% in the method of the present invention. More preferably, p53 activity is increased or enhanced by at least 20%. The neoplasia may be any of those described above, without regard to p53 status.

As disclosed herein, the inventor has used mass-spectrometry analysis of affinity-purified p53-associated factors to determine that ARF-BP1 bind and ubiquitates p53. ARF-BP1 inhibition strongly activates p53, even in the presence of excess Mdm2, and induces p53-dependent and p-53 independent cell-growth repression and apoptosis. Significantly, ARF-BP1 has an intrinsic enzymatic activity that specifically ubiquitinates p53, both in vitro and in vivo. In contrast, expression of a catalytically-inactive ARF-BP1 point mutant in cells increases the decreased levels of p53 ubiquitination, and stabilizes p53. These findings reveal an important mechanism by which p53 can be stabilized by direct deubiquitination. In view of the foregoing, the present invention further provides a method for deubiquitinating and/or stabilizing p53 in a cell containing p53. The method comprises contacting the cell with an ARF-BP1 inhibitor, in an amount effective to deubiquitinate and/or stabilize p53.

The method of the present invention may be used to deubiquitinate p53, or remove ubiquitin from p53, in vitro, or in vivo in a subject. Deubiquitination of p53 may be detected by known procedures, including any of the methods, molecular procedures, and assays disclosed herein. The ability of ARF-BP1 inhibition to modulate deubiquitination of p53 renders ARF-BP1 particularly useful for treating neoplasias, particularly p53-associated neoplasias, as described above. Accordingly, in one embodiment of the present invention, the subject is a human with neoplasia, and the ARF-BP1 inhibition treats the neoplasia.

The method of the present invention may be used to modulate deubiquitination of p53 (i.e., by removing ubiquitin from p53, or adding ubiquitin to p53) in vitro, or in vivo in a subject. As disclosed herein, where deubiquitination of p53 is increased, stability of p53 will also be increased. The ubiquitination and deubiquitination of p53 may be detected by known procedures, including any of the methods, molecular procedures, and assays disclosed herein.

The present invention also provides a method for identifying an agent that is reactive with p53, by assessing the ability of a candidate agent to inhibit ARF-BP1-p53 interaction. Unless otherwise indicated, "p53" includes both a p53 protein (GenBank Accession No. CAA38095), including conservative substitutions thereof, and a p53 analogue. A "p53 analogue" is a functional variant of the p53 protein, having p53 biological activity, that has 60% or greater (preferably, 70% or greater) amino-acid-sequence homology with the p53 protein. As further used herein, the term "p53 biological activity" refers to the activity of a protein or peptide that demonstrates detectable binding with ARF-BP1 (i.e., binding of approximately two fold, or, more preferably, approximately five fold, above the background binding of a negative control), under the conditions of the assays described herein, although affinity may be different from that of p53.

In one embodiment, in a competitive binding assay, standard methodologies may be used in order to assess the ability of a candidate agent to displace or replace ARF-BP1 in its binding to p53, thereby inhibiting the interaction of ARF-BP1 and p53. In such a competitive binding assay, the candidate agent competes with ARF-BP1 for binding to p53, and, once bound to p53, may sterically hinder binding of ARF-BP1 to p53, thereby preventing ubiquitination of p53 by ARF-BP1, otherwise stabilizing p53. A competitive binding assay represents a convenient way to assess inhibition of ARF-BP1-p53 interaction, since it allows the use of crude extracts containing p53 and ARF-BP1.

Accordingly, the present invention further comprises the steps of: (c) contacting the candidate agent with one or more cells comprising ARF, ARF-BP1, or p53; and (d) determining if the agent has an effect on one or more ARF, ARF-BP1-, or p53-associated biological events in the one or more cells. As used herein, a "ARF-BP1-associated biological event" includes a biochemical or physiological process in which ARF-BP1 activity has been implicated (e.g., neoplasia). In one embodiment of the present invention, for example, the method may further comprise the steps of: (c) contacting the candidate agent with one or more cells of a neoplasm (neoplastic cells); and (d) determining if the agent has an effect on proliferation of the neoplastic cells. As further used herein, a cell "comprising ARF-BP1" is a cell in which ARF-BP1, or a derivative or homologue thereof, is naturally expressed or naturally occurs.

The following materials and methods were used to generate the data described herein.

Plasmids and Antibodies

To clone the cDNA of ARF-BPI, five overlapped cDNA sequences that cover the full-length ARF-BPI were amplified by PCR from Marathon-Ready HeLa cDNA (Clontech, BD) and subcloned into pcDNA3.1/V5-His-Topo vector (Invitrogen). After sequence verification, the cDNA sequences were assembled and further cloned into expression vectors. To prepare mutant constructs (ARF-BPI (M), ARF-BP1(R), ARF-BP1M (R), cDNA sequences corresponding to different regions were amplified by PCR from above constructs using QuikChange Site-Directed Mutagenesis Kit (Stratagene), and subcloned into full length ARF-BP1 using specific restriction enzymes. For the HA-ARF-Flag construct, the HA and Flag sequence were introduced to the N terminus and C terminus ARF respectively by PCR and subcloned into the pCIN4 vector. To construct the Flag-p53, GST-ARF and GST-Mdm2 vectors, cDNA sequences corresponding to the full-length proteins were amplified by PCR from other expression vectors, and subcloned into either a pET-Flag or pGEX (GST) vector for expression in bacteria (Li et al., 2003, supra). To prepare GST-ARF mutant constructs, cDNA sequences corresponding to different regions were amplified by PCR from the ARF (wt) constructs. To construct adenovirus-ARF, the cDNA ARF was first cloned into pShuttle-IRES-hrGFP-1 vector (Stratagene). The resulting plasmid was then transformed for recombination into E. coli strain BJ5183 containing the adenoviral backbone plasmid pAdEasy-1. AD-293 cells were used for amplification of recombinant adenoviral ARF.

To prepare the ARF-BP1 antiserum, DNA sequences corresponding to 191 amino acids of ARF-BPI (residues 3435-3626) were amplified by PCR and subcloned into pGEX-2T (Luo, J. et al., Cell 107:137-48, 2001). α-ARF-BP1 antiserum was raised in rabbits against the purified GST-ARF-BP1 (3435-3626) fusion protein (Covance) and further affinity-purified on the antigen column. p53-specific monoclonal (DO-1) and polyclonal (FL-393) antibodies, anti-p21 polyclonal, anti-Mdm2 (SMP40) monoclonal antibody, Myc polyclonal antibody were purchased from Santa Cruz. Anti-GFP monoclonal and anti-GST monoclonal antibody were purchased from Clontech. Anti-V5 monoclonal antibody was purchased from Invitrogen. Mouse monoclonal (4C 6/4) p14ARF and rabbit polyclonal p14ARF (ab470) antibodies were purchased from Abcam.

Purification of ARF-Complexes From Human Cells

The epitope-tagging strategy to isolate ARF-containing protein complexes from human cells was performed essentially as previously described with some modifications (Luo, J. et al., Nature 408:377-81, 2000; Nikolaev, A. Y. et al., Cell 112:29-40, 2003). In brief, to obtain an HA-ARF-Flag expressing cell line, p53 null H1299 cells were transfected with pCIN4-HA-ARF-Flag and selected for 2 weeks in 1 mg/ml G418 (GIBCO). The tagged ARF protein levels were detected by Western blot analysis. The stable cell lines were chosen to expand for complex purification based on the fact that the expression levels of the ectopic ARF protein in H1299 cells were very close to the levels of endogenous protein. Thus, the cells were grown in DMEM with 10% fetal bovine serum and harvested near confluence. The cell pellet was resuspended in buffer A (10 mM HEPES pH 7.9, 10 mM KCl, 0.1 mM EDTA, 1 mM DTT, 0.5 mM PMSF and protein inhibitor mixture [Sigma]). The cells were allowed to swell on ice for 15 min, after which 10% NP 40 (Fluka) was added until a final concentration of 0.5%. The tube was vigorously vortex for 1 min. The homogenate was centrifuged for 10 min at 4,000 rpm. The nuclear pellet was resuspended in ice-cold buffer C (20 mM HEPES pH 7.9, 0.4 M NaCl, 1 mM EDTA, 1 mM DTT, 1 mM PMSF and protein inhibitor mixture) and the tube was vigorously rocked at 4° C. for 45 min. The nuclear extract was diluted with buffer D (20 mM HEPES [pH 7.9], 1 mM EDTA) to the 100 mM final NaCl concentration, ultra-centrifuged 25,000 rpm for 2 hr at 4° C. After filtered with 0.45/μm syringe filters (NALGENE), the supernatants were used as nuclear extracts for M2 immunoprecipitations by anti-FLAG antibody-conjugated agarose (Sigma). The bound polypeptides were eluted with the FLAG peptide and were further affinity purified by anti-HA antibody-conjugated agarose (Sigma). The final elutes from the HA-beads with HA peptides were resolved by SDS-PAGE on a 4%-20% gradient gel (Novex) for silver staining or colloidal-blue staining analysis. Specific bands were cut out from the gel and subjected to mass-spectrometry peptide sequencing.

Ablation of Endogenous ARF-BP1 by RNAI in Both P53-Null Cells and p53 Expressing Cells p53-null cell lines (H1299 and Saos-2), and p53-expressing cells (U2OS, MCF-7 and A549) were maintained in DMEM medium supplemented with 10% fetal bovine serum. The HCT116 and HCT116-p53(−/−) cell lines were kindly provided by B. Vogelstein's lab. The RNAi-mediated ablation of endogenous ARF-BP1 was performed essentially as previously described (Elbashir, S. M. et al., Nature 411:494-498, 2001). A 21-nucleotide siRNA duplex with 3'dTdT overhangs corresponding to ARF-BP1 mRNA (ARF-BP1 #1) (AAUUGCUAUGUCUCUGGGACA (SEQ ID NO:18)) or (ARF-BP1 #2) (AAGUAUCCCUACCAC-CUCAUG (SEQ ID NO:19)) was synthesized (Dharmacon). The same sequence (ARF-BP1 #1 mutant) with 2 nucleotides changed (AAUUGCCAUGUAUCUGGGACA (SEQ ID NO:20)) was used as a specific RNAi control. The sequence (AAGAGGACUCCGCUACUGACA (SEQ ID NO:21)) was used as mouse ARF-BP1 RNAi for MEF cells. The sequence AAGGUGGGAGUGAUCAAAAGG (SEQ ID NO:22) was used for Mdm2 RNAi.

BRDU Labeling

The BrdU incorporation assay was performed essentially as previously described (Yarbrough, W. G. et al., Cancer Res 62:1171-7, 2002). In brief, cells were grown in medium containing 20 gM BrdU (Calbiochem) for 2 h and then fixed in 70% ethanol. DNA was denatured, and cells were permeabilized in 2N HCl, 0.5% Triton X-100 (Sigma), neutralized in 0.1 M $Na_2B_4O_7$ (pH 8.5), and then blocked with 1% BSA in PBS. Anti-BrdU was added following the manufacturer's protocol (Amersham). After washing with 1% BSA/PBS, the cells were incubated with Alexa488 conjugated anti-mouse IgG (Molecular Probes). Finally, cells were counterstained with DAPI to visualize the nuclei.

Protein Purification of the Components for In Vitro Ubiquitination Reactions

To prepare the purified components for the in vitro ubiquitination assay (Li et al., 2003, supra), Flag-p53, E3 (GST-ARF-BP1 3760-4374), and GST-ARF were induced in Rosetta (DE3) pLys (Novagen) cells at room temperature and proteins were extracted with buffer BC500 (20 mM Tris-HCl, pH7.3, 0.2 mM EDTA, 500 mM NaCl, 10% glycerol, 1 mM DTT and 0.5 mM PMSF) containing 1% NP-40, and purified on either glutathione-Sepharose (Pharmacia) or M2 beads (Sigma). Rabbit E1 was obtained from Calbiochem. Rabbit E2 and His-Ub were purchased as a purified protein from Affinity Inc.

In Vitro Ubiquitination Assays

The in vitro ubiquitination assay was performed as described previously (Li et al, 2003, supra) with some modifications. For the self ubiquitination assay, 200 ng of bacteria-produced GST-ARF-BPI (3760-4374) or its ca mutant was mixed with other components, including E1 (10 ng), E2 (His-UbcH5a, 100 ng), and 5 µg of His-ubiquitin (affinity) in 10 µl of reaction buffer (40 mM Tris, 5 mM $MgCl_2$, 2 mM ATP, 2 mM DTT, pH 7.6). 400 ng of bacteria produced GST-ARF or GST-ARF mutant protein was added as inhibitor. The reaction was stopped after 60 min at 37° C. by addition of SDS sample buffer, and subsequently resolved by SDS-PAGE gels for Western blot analysis.

For p53 ubiquitination, 20 ng of the bacteria produced Flag-p53 was mixed with other components, including E1 (100 ng), E2 (His-UbcH5a, 1 µg), E3 (bacteria produced GST-ARF-BP1 (3760-4374) (400 ng), and 20 µg of bacteria produced His-HA-ubiquitin in 100 µl of reaction buffer (40 mM Tris, 5 mM $MgCl_2$, 2 mM ATP, 2 mM DTT, pH 7.6). 1 µg of bacteria produced GST-ARF or GST-ARF mutant protein was added as an inhibitor. After 2 hr incubation at 37° C., 15 µl of anti-FLAG antibody-conjugated agarose was added following addition of 500 µl Flag lysis buffer, and subsequently rotated at 4° C. overnight. The elutes were analyzed by Western blot with anti-p53 (DO-1) antibody.

The present invention is described in greater detail in the examples which follow, which should be considered as illustrative and nonlimiting.

EXAMPLE 1

This example demonstrates identification of ARF-BP1 as a major component of the ARF-associated nuclear complexes from p-53-null cells To identify the in vivo targets for ARF-mediated function an epitope tagging procedure was used to isolate ARF-containing protein complexes from human cells. The method was developed by the present inventor to purify protein complexes such as the HDACl and p53 complexes (Gu, W., Malik, S., Ito, M., Yuan, C. X., Fondeil, J. D., Zhang, X., Martinez, E., Qin, J., Roeder, R. G., Mol Cell 3:97-108, 1999; Luo, J., Su, P., Chen, D., Shiloh, A., Gu. W. Nature 408:377-81, 2000; Nikolaev, A. Y., Li, M., Puskas, N., Qin, J., Gu, W., Cell 11:29-40, 2003); nevertheless, some modifications were made to improve the stoichiometry of the protein complexes. In particular, a derivative of the human lung carcinoma p53-null H1299 cell line that stably expresses a double-tagged human ARF protein containing a N-terminal HA- and C-terminal FLAG epitope (HA-ARF-Flag (FIG. 1A) was generated. To avoid non-physiological interactions that might occur in cells that overexpress ARF, H1299 derivatives that express the ectopic ARF protein at levels similar to those of endogenous ARF (FIG. 1B) were used. As such, the tagged protein complexes reflected native conditions of the endogenous ARF complexes.

To isolate protein complexes containing ARF, nuclear extracts from HA-ARF-Flag expressing H1299 cells and from control cells (parental H1299) were first subjected to affinity chromatography on M2 (Flag antibody) agarose beads. The bound proteins were eluted with the FLAG peptide, and the elutes were chromatographed on a HA-affinity column. Finally, the bound proteins were eluted from the column with an HA peptide, fractionated by SDS-PAGE, and visualized by silver staining (FIG. 1C). B23/necleoplasmin (NPM), a known ARF-binding protein, was identified from the complexes (FIG. 1C). Unexpectedly, a major protein band of ~500 kDa (p500) also co-purified with ARF from HA-ARF-Flag-expressing H1299 cells (lane 2) but not from parental H1299 cells (lane 1) was found suggesting that this protein is a specific binding partner of ARF. The protein was designated as ARF-BP1 (ARF-binding protein 1). Significant levels of Mdm2 were not detected in these complexes by Western blot analysis, and mass spectrometric analysis of additional minor bands that co-purified with ARF (FIG. 1C), failed to identify Mdm2 sequences. Thus, these data suggest that ARF-BP1 is a major component of the ARF-associated complexes of these cells.

EXAMPLE 2

This example demonstrates the initial characterization of ARF-BP1, a novel ubiquitin E3 ligase.

Peptide sequencing of the ARF-BP1 band by mass spectrometry revealed two peptide sequences, matched a single partial cDNA clone in the GeneBank database (accession number Gi 22090626). A small fragment of this protein named UREB1 (upstream initiator-like sequence binding protein 1) was originally identified by the present inventor as a binding protein of the preprodynorphin gene promoter, but its biological functions were previously unknown (Gu, J., Ren, K., Dubner, R., and Iadarola, M. J., Brain Res Mol Brain Res. 24:77-88, 1994).

A full-length human ARF-BP1 cDNA was assembled by RACE (Rapid amplification of cDNA ends) and homology alignment with the partial cDNA sequences in the database. The human ARF-BP1) cDNA encodes a 4374 amino acid protein (FIGS. 2A and 3) and the full length protein of ARF-BP1 is more than 3000 amino acids longer than the published UREB1 sequences (Gu et al., 1994, supra). SEQ ID NO: 1 represents the DNA sequence encoding the human ARF-BP1 protein (FIG. 2A)). SEQ ID NO: 2 represents the amino acid sequence of the human ARF-BP1 protein (FIG. 3).

Figure 2:
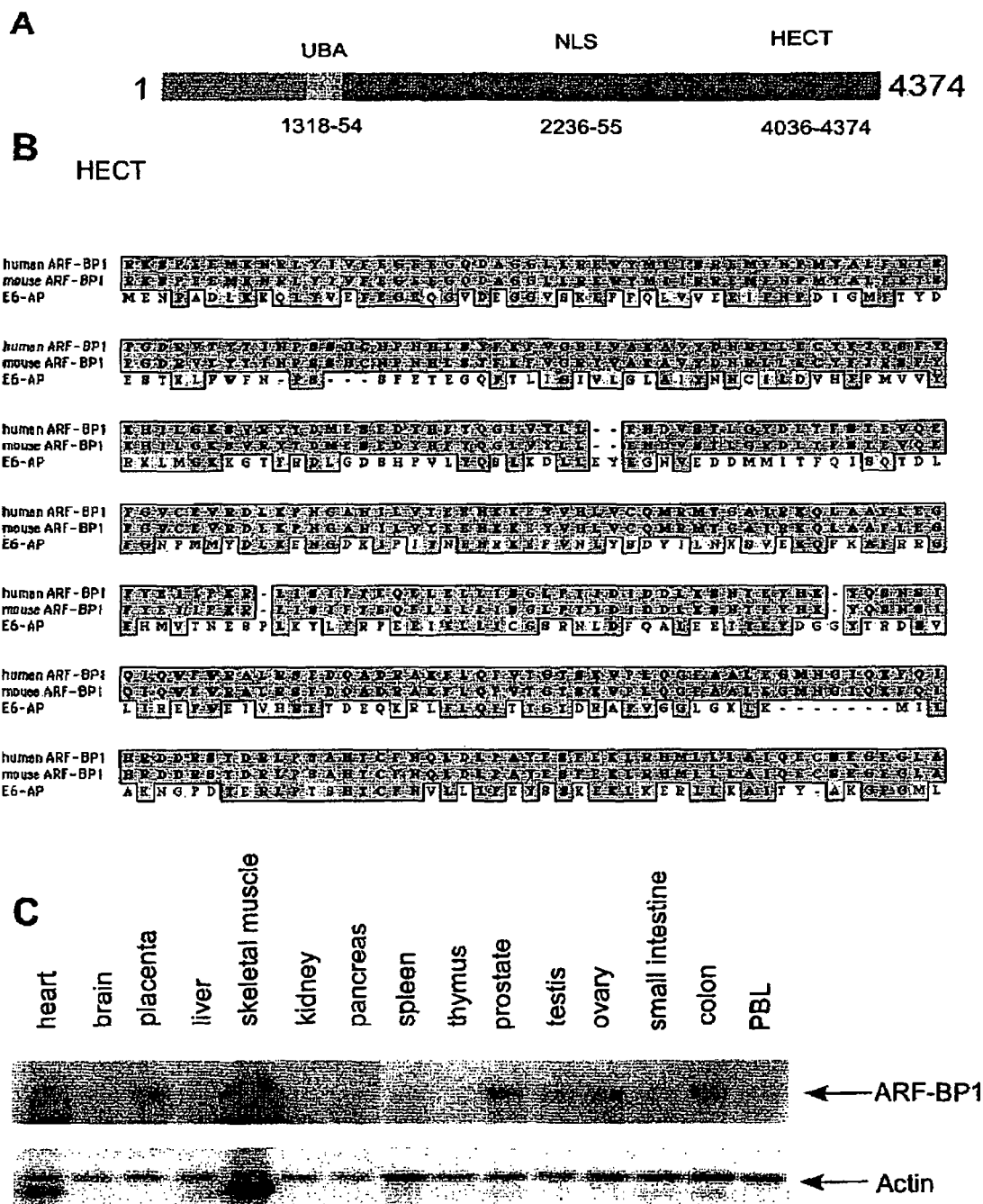
FIGS. 2A-C demonstrate that ARF-BP1 contains a signature HECT-motif and a UBA domain.

The C-terminal sequences of ARF-BP1 possess a signature motif (the HECT domain) common to a number of ubiquitin E3 ligases (FIGS. 2A and 2B). The HECT domain sharing a conserved about 350-amino acid, harbors the Cys residue that forms a catalytic thiol ester with Ub and is regarded as a bona fide E3 ligase enzymatic motif. ARF-BP1 also contains the ubiquitin associated domain (UBA) (FIGS. 2A and 4), a small sequence motif found in various proteins linked to the ubiquitination pathway, such as the DNA repair protein Rad23 or the Cb1 ubiquitin ligase (Hicke, L., and Dunn. R., *Annu Rev Cell Dev Biol* 19:141-172, 2003; Buchberger, A., *Trends in Cell Biol.* 12:216-221, 2002. Northern blot analysis showed that the ARF-BP1 mRNA is ubiquitously expressed in different types of human tissues (FIG. 2C).

EXAMPLE 3

This example demonstrates that ARF-BP1 interacts with ARF both in vitro and in vivo.

Figure 5:
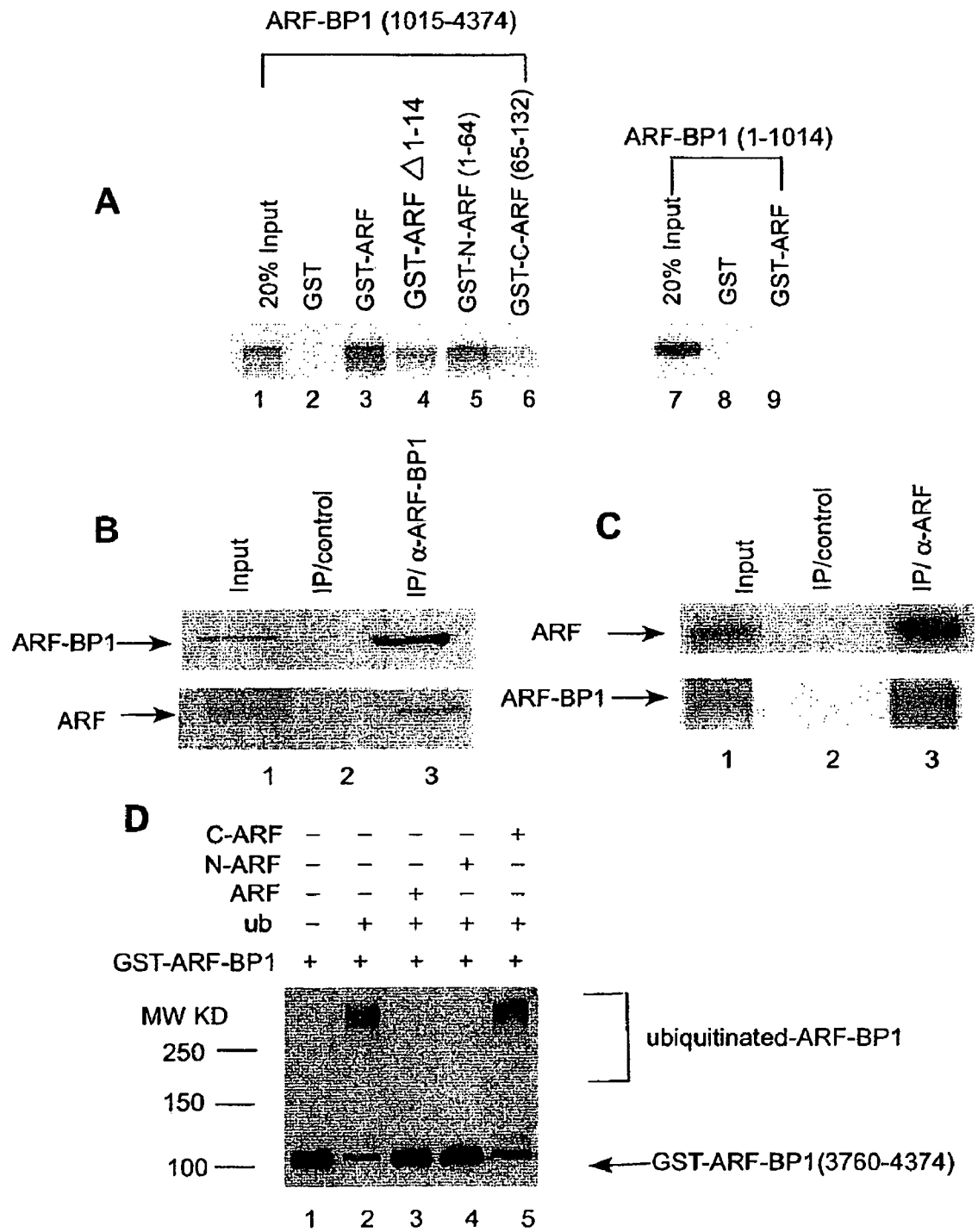
FIGS. 5A-D shows that ARF interacts with ARF-BP1 in vitro and in vivo and ARF-BP1-mediated ubiquitin ligase activity is inhibited by ARF.

To confirm the physical interaction between ARF and ARP-BP1, the in vitro binding of ARF-BP1 to ARF was evaluated. The ARF polypeptide can be roughly divided into two major functional domains: an N-terminus region encoded by the unique 1β exon (N-ARF: residues1-64), which are critical for ARF-mediated p53 activation as well as p53-independent ARF functions, and a C-terminal region (C-ARF:residues 65-132), not conserved between human and mouse counterparts and of uncertain function. As shown in FIG. 5A, $^{35}$S-labeled ARF-BP1(1-1014), a polypeptide comprising the N-terminal 1014 residues of ARB-BP1, did not associate with immobilized GST-ARF (lanes 7-9). In contrast, however, $^{35}$S-labeled ARF-BP1 (1015-4574) strongly bound both full-length ARF (GST-ARF, lane 3) and the N-terminal ARF domain (GST-N-ARF, lane 5) but not the C-terminal ARF domain (GST-C-ARF, lane 6) or GST alone (lane 2). Interestingly, ARF-BP1 weakly bound the ARF mutant (GST-ARFΔ1-14; (lane 4), indicating that deletion of the first 14 amino acids significantly compromises but does not completely eliminate the ARF and ARF-BP1 interaction.

To confirm the interaction between ARF and ARF-BP1 in vivo, an affinity-purified polyclonal antiserum was raised against the 191 amino acid segment of ARF-BP1 (residues 3435-3626), a region that shows no apparent homology with any known proteins. Upon Western blot analysis, this antibody specifically detected ARF-BP1 polypepetides in human cells (lane 1, FIG. 5B). To investigate the interaction between endogenous ARF-BP1 and ARF polypeptides, cell extracts from native H1299 cells were immunoprecipitated with α-ARF-BP1 or with the control IgG. Western blot analysis revealed that this antibody immunoprecipitated endogenous ARF-BP1 (lane 3, upper panel, FIG. 5B); more importantly, ARF was clearly detected in the immunoprecipitations obtained with the α-ARF-BP1 antiserum (lane 3, lower panel, FIG. 5B) but not the control IgG (lane 2, lower panel, FIG. 5B). Conversely, endogenous ARF-BP1 was readily immunoprecipitated with the ARF-specific antibody (lane 3, FIG. 5C), but not with a control antibody (lane 2, FIG. 5C). These data indicate that ARF and ARF-BP1 interact both in vitro and in vivo.

EXAMPLE 4

This example demonstrates that the HECT domain of ARF-BP1 has an ubiquitin ligase activity that is strongly inhibited by ARF.

ARF can stabilize p53 by sequestering Mdm2 in the nucleolus and can also stabilize p53 by directly inhibiting the enzymatic activity of Mdm2. To examine whether ARF can also inhibit the ubiquitin ligase activity of ARF-BP1, ARF-BP1 was tested for enzymatic activity in an in vitro assay using purified components. The GST-ARF-BP1 (3760-4374) polypeptide (FIG. 3; SEQ ID NO: 2), which includes the HECT domain of ARF-BP1, was expressed in bacteria and purified to near homogenicity. As shown in FIG. 5D, ubiquitin-conjugated forms of ARF-BP1 were readily formed when GST-ARF-BP1 (3760-4374) was incubated in the presence of ubiquitin, E1, and an E2 (UbcH5c) (lane 2). Notably, this activity was strongly represented by recombinant full-length ARF (lane 3). Moreover, consistent with the binding results (FIG. 5A), the evolutionarily conserved N-terminal region of ARF, but not the C-terminal region, also inhibited ARF-BP1-mediated autoubiquitination (lanes 4, 5). These data suggest that ARF functions as a potent inhibitor of the ARF-BP1 ubiquitin ligase activity.

EXAMPLE 5

This example demonstrates that inactivation of ARF-BP1 induces cell growth repression in p53-null cells.

Figure 6:
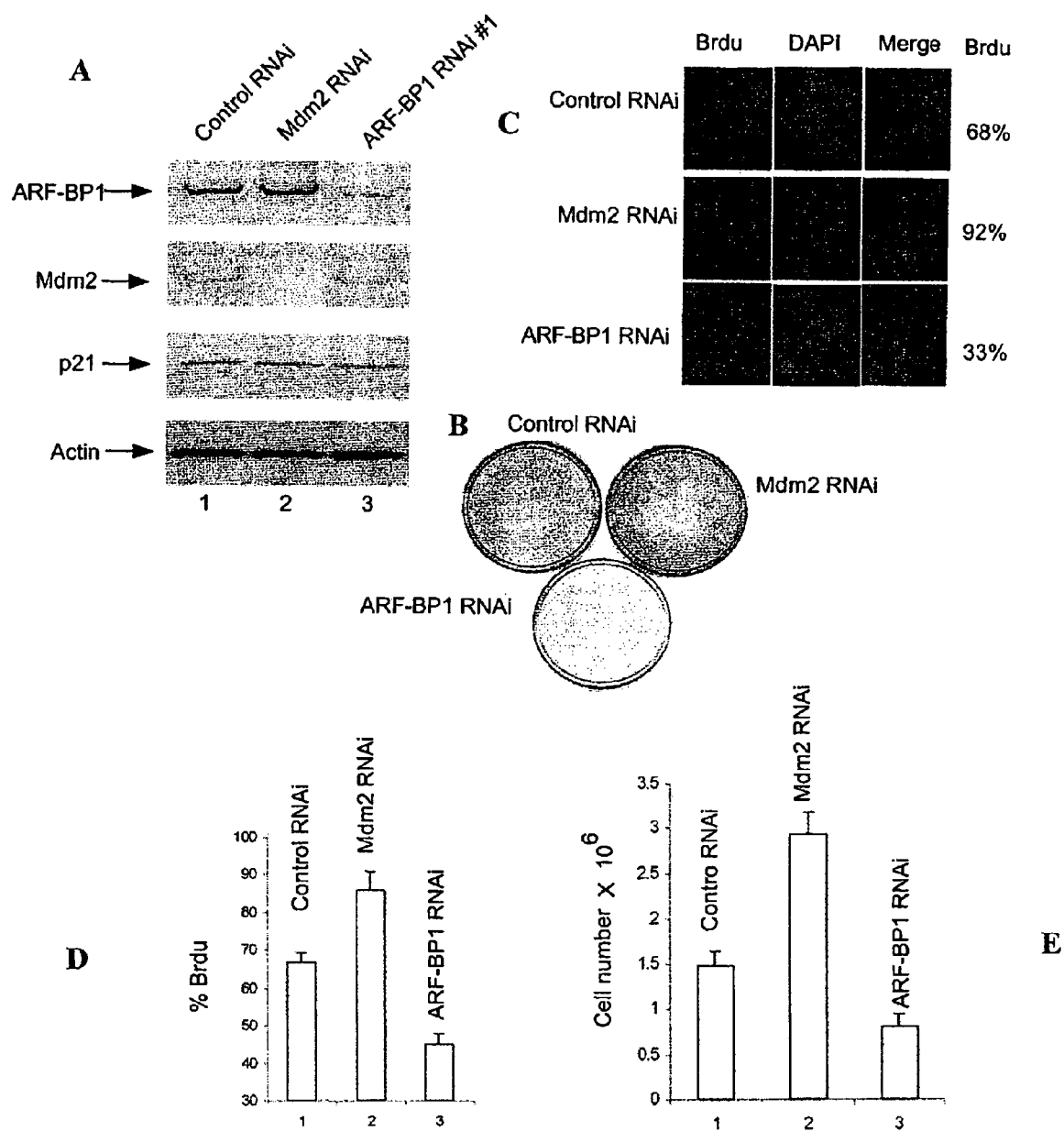
FIGS. 6A-E illustrate that inactivation of endogenous ARF-BP1, but not Mdm2, induces cell growth arrest in p53-null H1299 cells.
Figure 7:
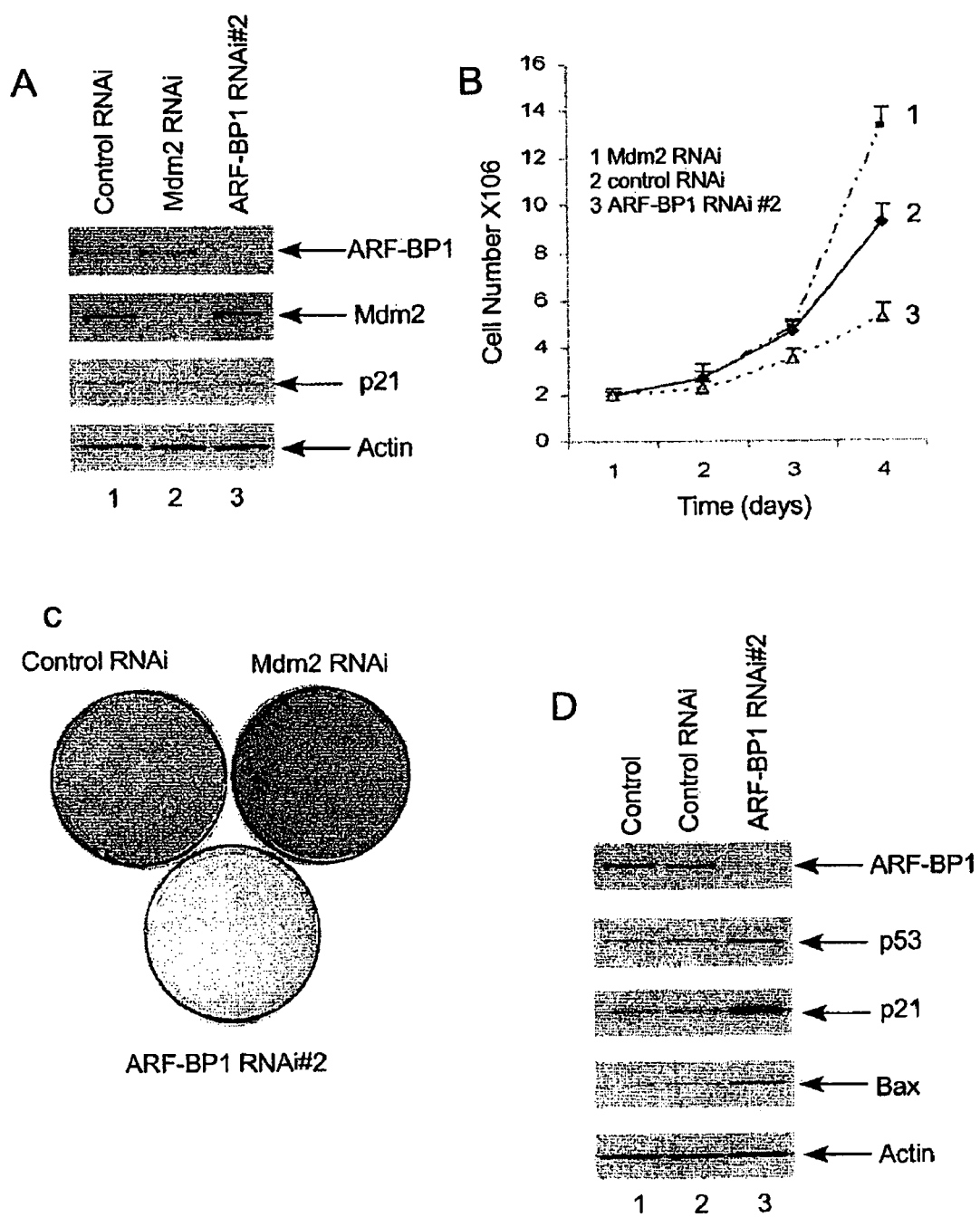
FIGS. 7A-D demonstrate that inactivation of endogenous ARF-BP1, but not Mdm2, induces cell growth arrest in p53-null H1299 cells and stabilizes p53 in U20S cells.

Although in normal cells ARF stabilizes and activates p53 by inhibiting Mdm2 function, ARF can also inhibit the growth of p53-null cells. To determine whether ARF induces p53-independent growth suppression by inhibiting ARF-BP1 function, the present invention examined whether inactivation of endogenous ARF-BP1 also represses cell growth in p53-null cells in a manner reminiscent of ARF induction. p53-null H1299 cells were transfected with either an ARF-BP1-specific (ARF-BP1-RNAi# 1) or a control (GFP-RNAi) siRNA. As shown in FIG. 6A, the levels of endogenous ARF-BP1 polypeptides were severely reduced after three consecutive transfections (upper panels, lane 3 vs. lane 2) with ARF-BP1-RNAi#1. The steady state levels of p21 and Mdm2, two transcriptional targets of p53, were unaffected by ARF-BP1 ablation. Unexpectedly, ARF-BP1-RNAi treatment significantly reduced the growth rate of these cells (FIG. 6B), suggesting that ARF-BP1 inactivation induces cell growth repression. These cells grew slightly faster when endogenous Mdm2 expression was diminished with RNAi in these cells (FIG. 6A, 6B). By monitoring BrdU incorporation (FIG. 6C), the present inventor discovered that ARF-BP1 knockout inhibits, while Mdm2 knockdown modestly promotes, the growth of p53-null cells. Similar results were also obtained with another p53-null cell line (SaoS-2, FIG. 6D and 6E) and another siRNA (RNAi/ARF-BP1 #2) that recognizes a different region of the ARF-BP1 mRNA (FIG. 7A-D).

Figure 8:
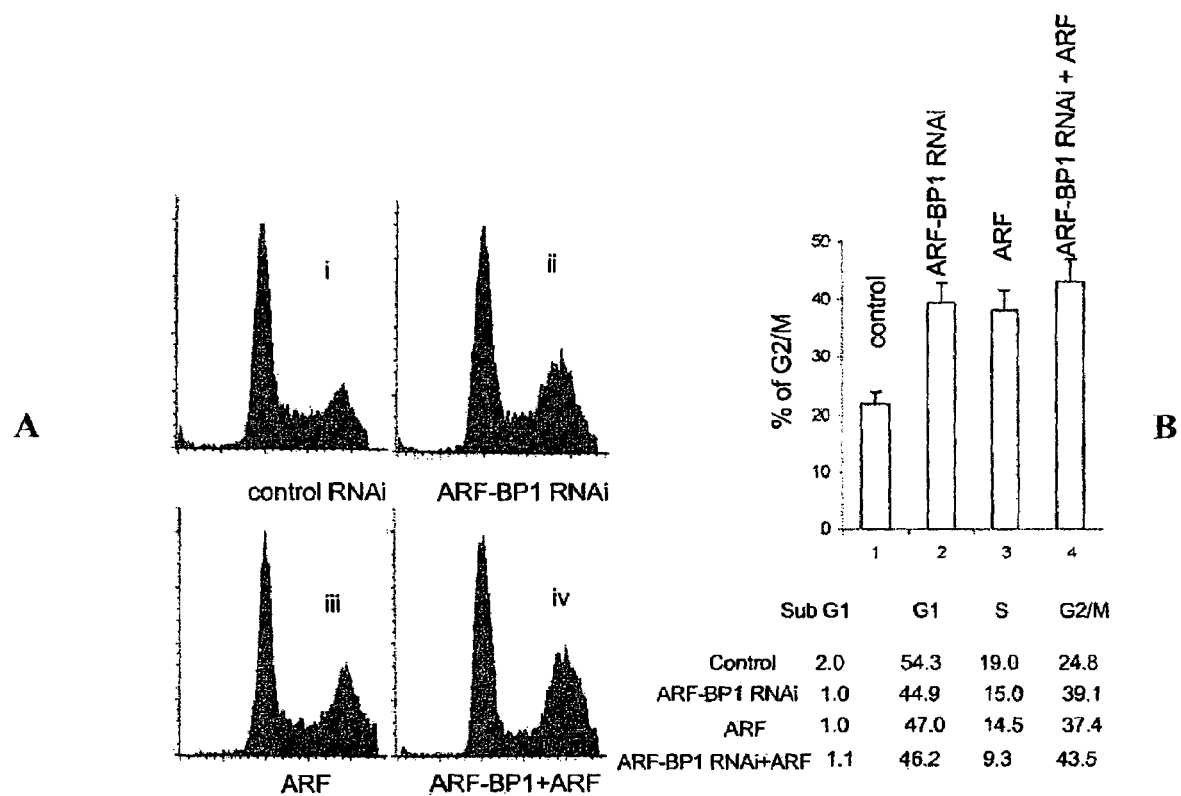
FIGS. 8A-B illustrate that inactivation of ARF-BP1 induces G2M arrest in H1299 cells, similar to overexpression of ARF.

ARF-mediated cell growth in p53-null cells is not well characterized and there is evidence that ARF expression induces G2/M arrest in a number of p53-null human cell lines (Normand, G. et al., 2005). To analyze the nature of cell growth arrest mediated by ARF-BP1 inactivation in H1299 cells, the effect of ARF expression in these cells was examined. As shown in FIG. 8, ARF expression induced G2/M accumulation of these cells but no obvious apoptotic cells (Sub-G1) were observed (iii vs i). Unexpectedly, inactivation of ARF-BP1 by ARF-BP1 RNAi in these cells also led to G2/M arrest at similar levels (FIG. 8). These results show that inactivation of ARF-BP1, inhibits the growth of these p53-null cells in a manner reminiscent of ARF induction.

EXAMPLE 6

This example demonstrates that inactivation of endogenous ARF-BP1 in normal cells stabilizes p53 and induces p53-dependent apoptosis.

Figure 9:
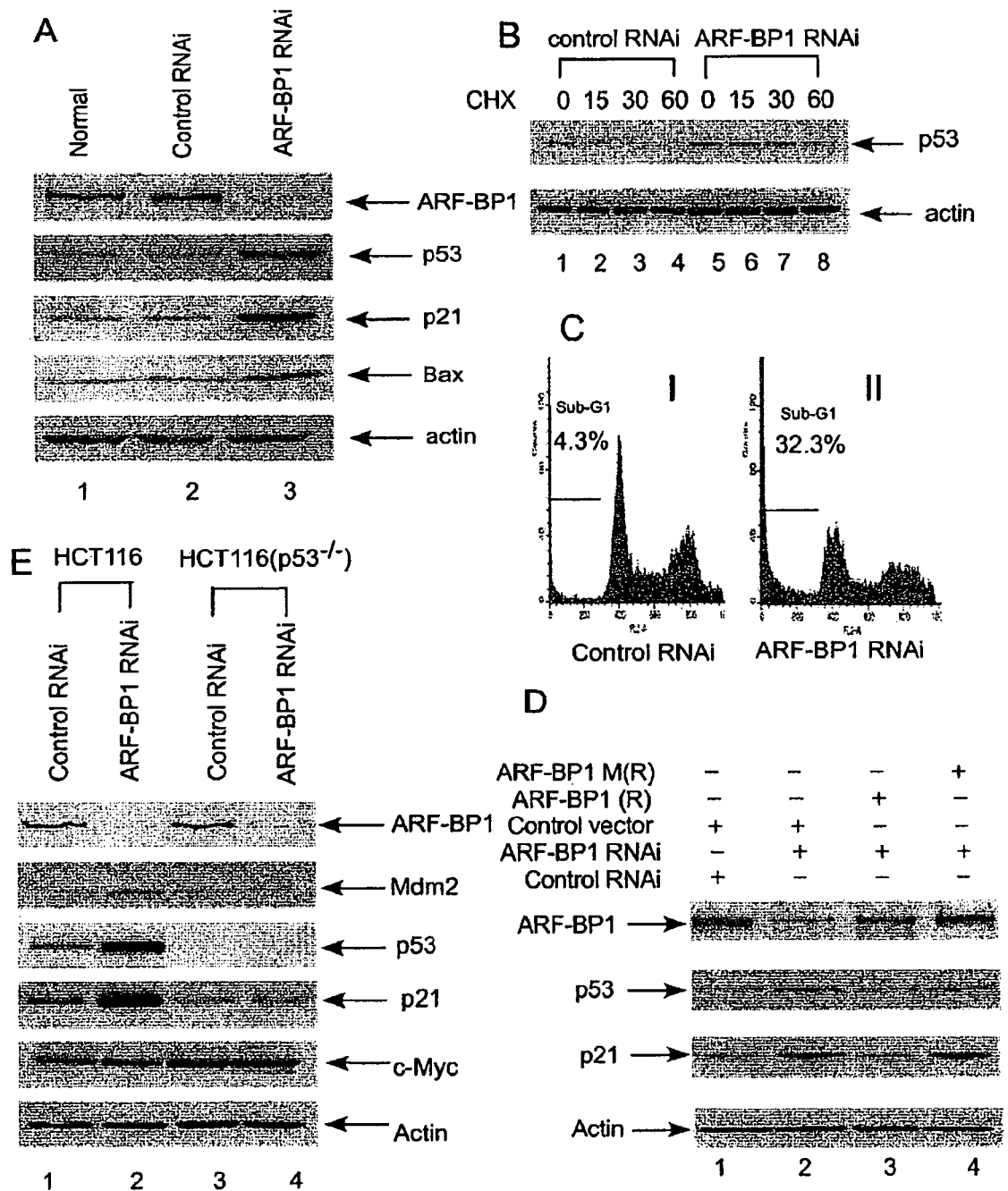
FIGS. 9A-E demonstrate that inactivation of ARF-BP1 stabilizes p53 and induces p53-dependent apoptosis. FIG.
Figure 10:
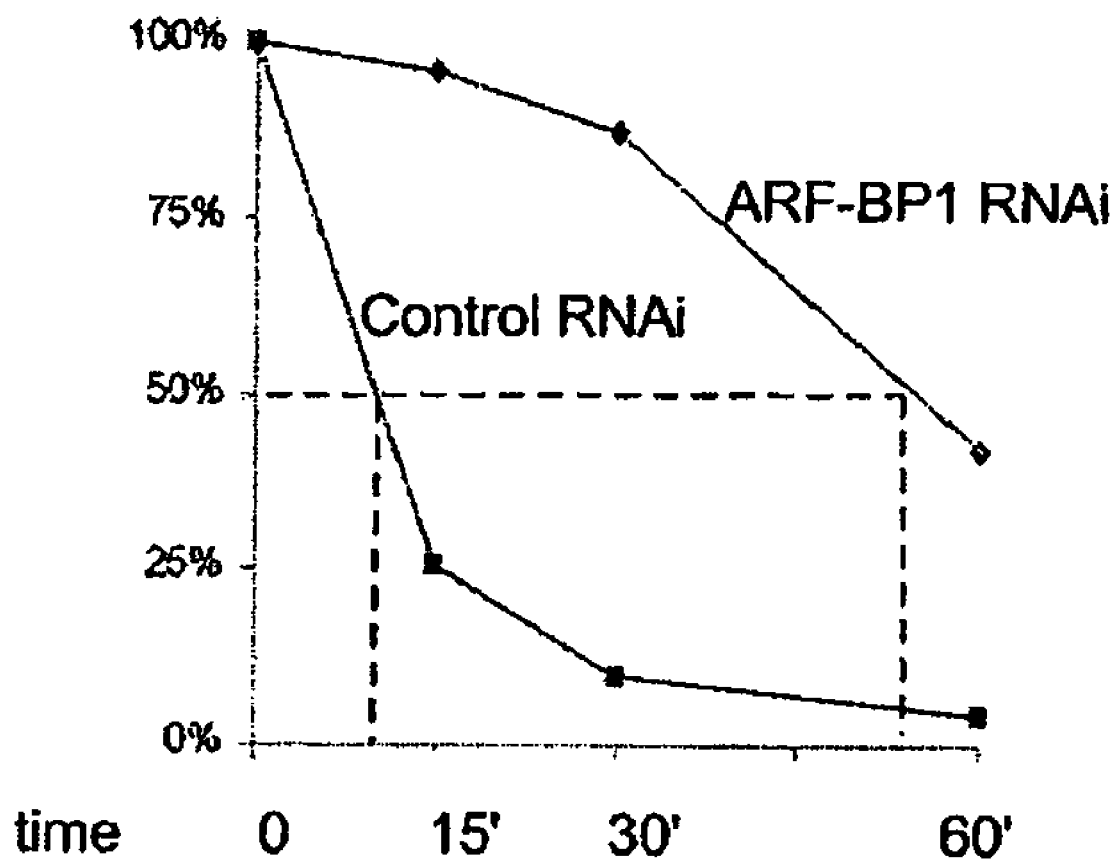
FIG. 10 is a line graph showing the quantitation of the p53 half-life in the cells treated with control RNAi or ARF-BP1 RNAi.

To further investigate the role of the ARF and ARF-BP1 interaction in p53-positive cells, the functional consequences of ARF-BP1 inactivation in cells expressing wild-type p53 was tested. Human osteosarcoma U2OS cells were transfected with either an ARF-BP1-specific siRNA (ARF-BP1-RNAi#1) or control siRNA (GFP-RNAi). Unexpectedly, RNAi-mediated knockdown of ARF-BP1 expression elevated the steady-state levels of endogenous p53 (FIG. 9A) and extended the half-life of p53 polypeptides (FIGS. 9B and 10). The expressions of p21 and BAX, the transcriptional targets of p53, were strongly induced by ARF-BP1 inactivation (FIG. 9A). ARF-BP1 ablation also induced programmed cell death; as shown in FIG. 9C, 32.3% of the ARF-BP1-RNAi#1-treated U2OS cells underwent apoptosis (II), while no significant apoptosis was observed in control transfected cells (I). These data indicate that inactivation of ARF-BP1 stabilizes p53 and activates its mediated functions.

Given that Mdm2 is considered the primary target in ARF-mediated p53 activation, these results were unexpected. To verify the specific effects induced by ARF-BP1 ablation, control experiments were conducted.

Figure 11:
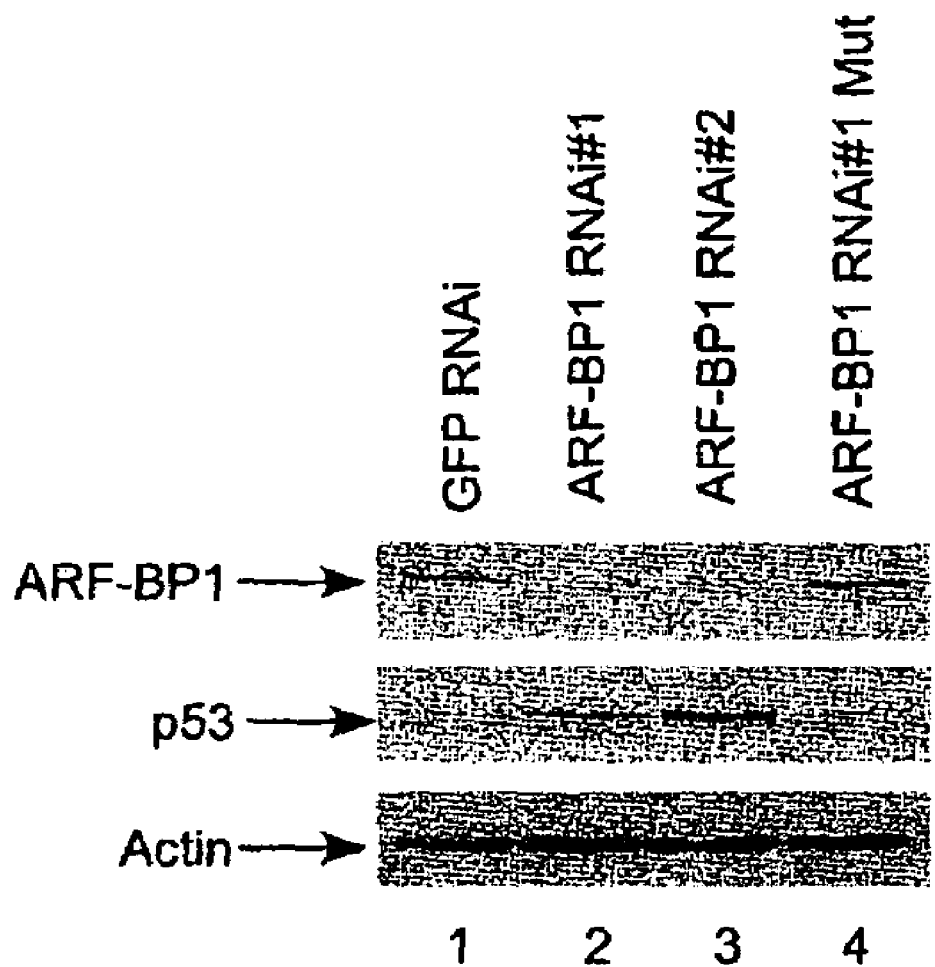
FIG. 11 depicts the effects of different ARF-BP1 RNAi oligonucleotides and shows Western blot analysis of cell extracts from U2OS cells treated with control-RNAi (GFP-RNAi) (lane 1), ARF-BP1-RNAi #1 (lane 2), ARF-BP1-RNAi#2 (lane 3), or ARF-BP1-RNAi#1 mutant (lane 4).
Figure 12:
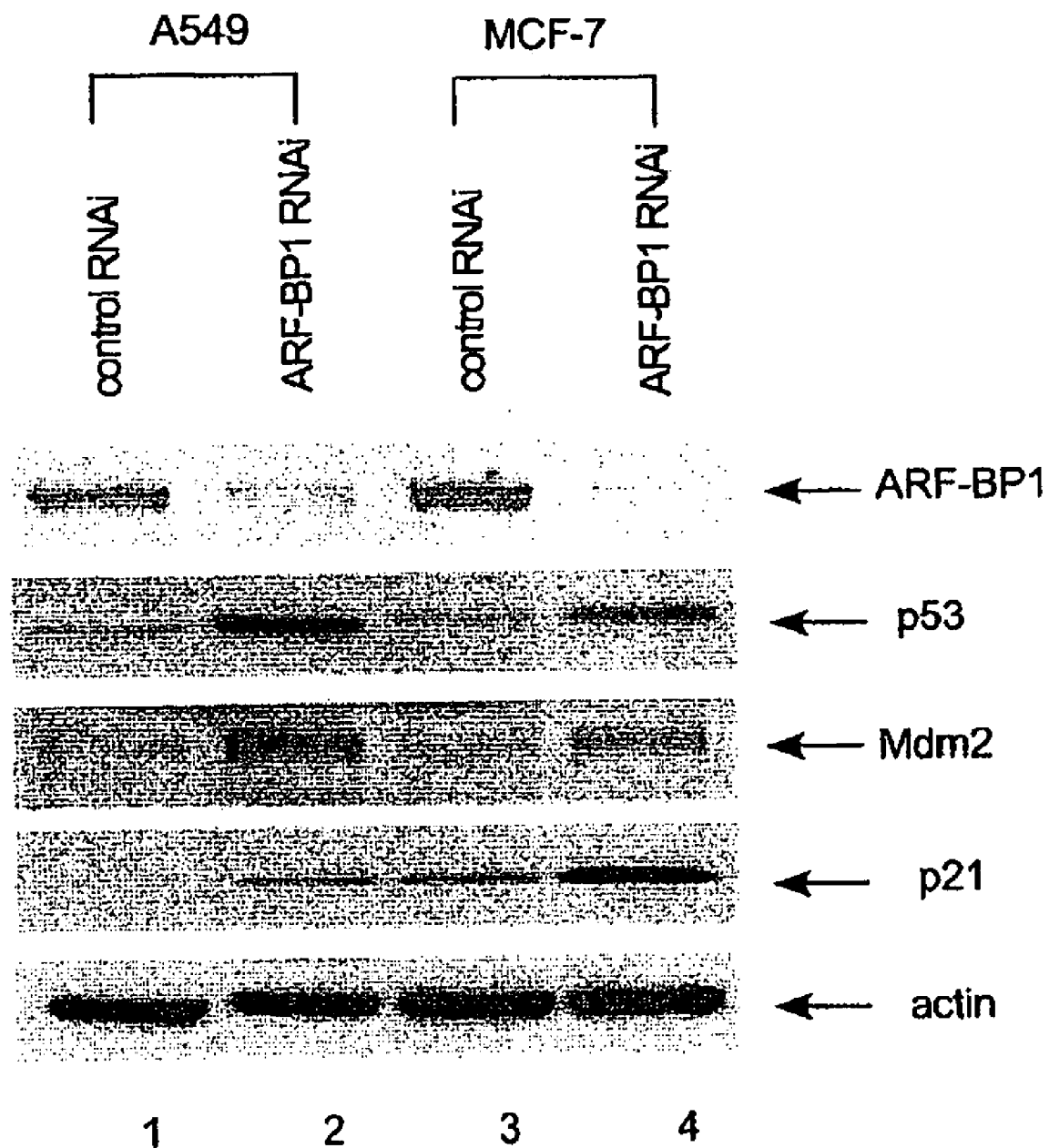
FIG. 12 depicts that RNAi-mediated ablation of ARF-BP1 induces p53 activation in A549 and MCF-7 cells showing whole cells extracts from human lung adenocarcinoma A549 (lane 1, 2) or human breast cancer MCF-7 cells (lanes 3, 4) treated with either ARF-BP1-RNAi (lane 2, 4) or control-RNAi (lane 1, 3) immunoblotted with anti-ARF-BP1, anti-p53 (DO-1), anti-Mdm2, anti-p21, and anti-actin (AC-15) antibodies.
Figure 13:
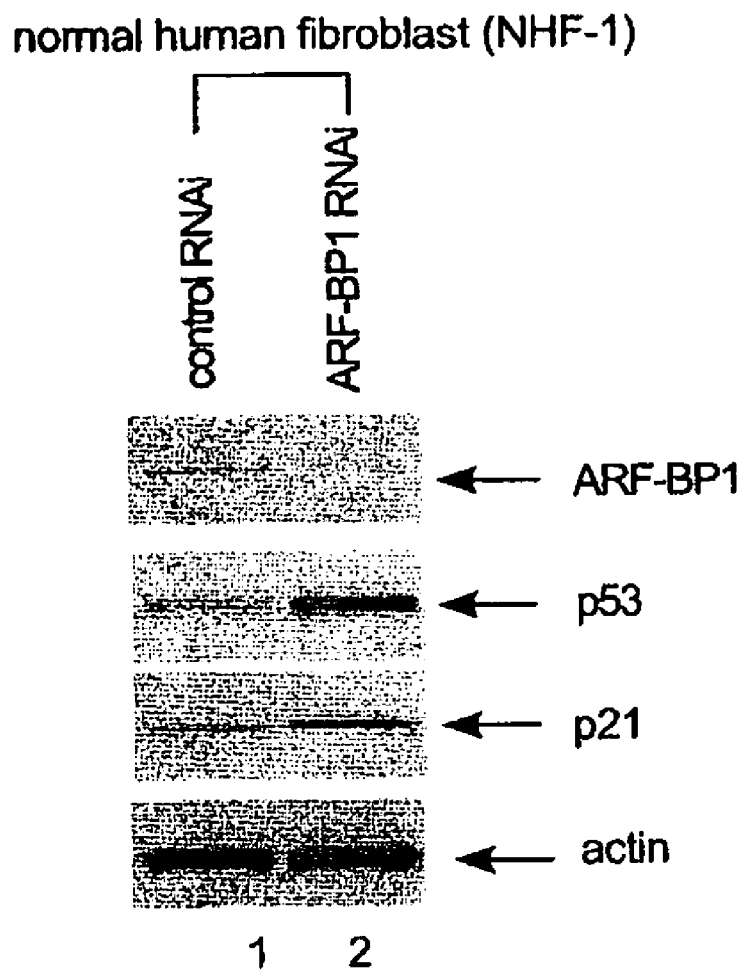
FIG. 13 demonstrates that RNAi-mediated ablation of ARF-BP1 induces p53 activation in normal human fibroblast (NHF-1) cells. Western blot analysis of cell extracts from normal human fibroblast cells (NHF-1) treated with ARF-BP1-RNAi (lane 2) or control-RNAi (lane 1) by anti-ARF-BP1, anti-p53 (DO-1), anti-p21, and anti-actin antibodies.

Using another ARF-BP1-specific siRNA (RNAi/ARF-BP1 #2), which recognizes a different region of ARF-BP1 mRNA (see Methods), but not with a point mutant form of the siRNA (ARF-BP1-RNAi#1mut) (FIGS. 7D and 11), knockdown levels of endogenous ARF-BP1 proteins were performed. The levels of p53 were elevated in those cells. Similar results were obtained using a variety of different cell lines that retain wild-type p53 function, including MCF-7 human breast carcinoma cells (FIG. 12), A549 human lung adenocarcinoma cells (FIG. 12) and normal human fibroblast cells (NHF-1) (FIG. 13).

Figure 14:
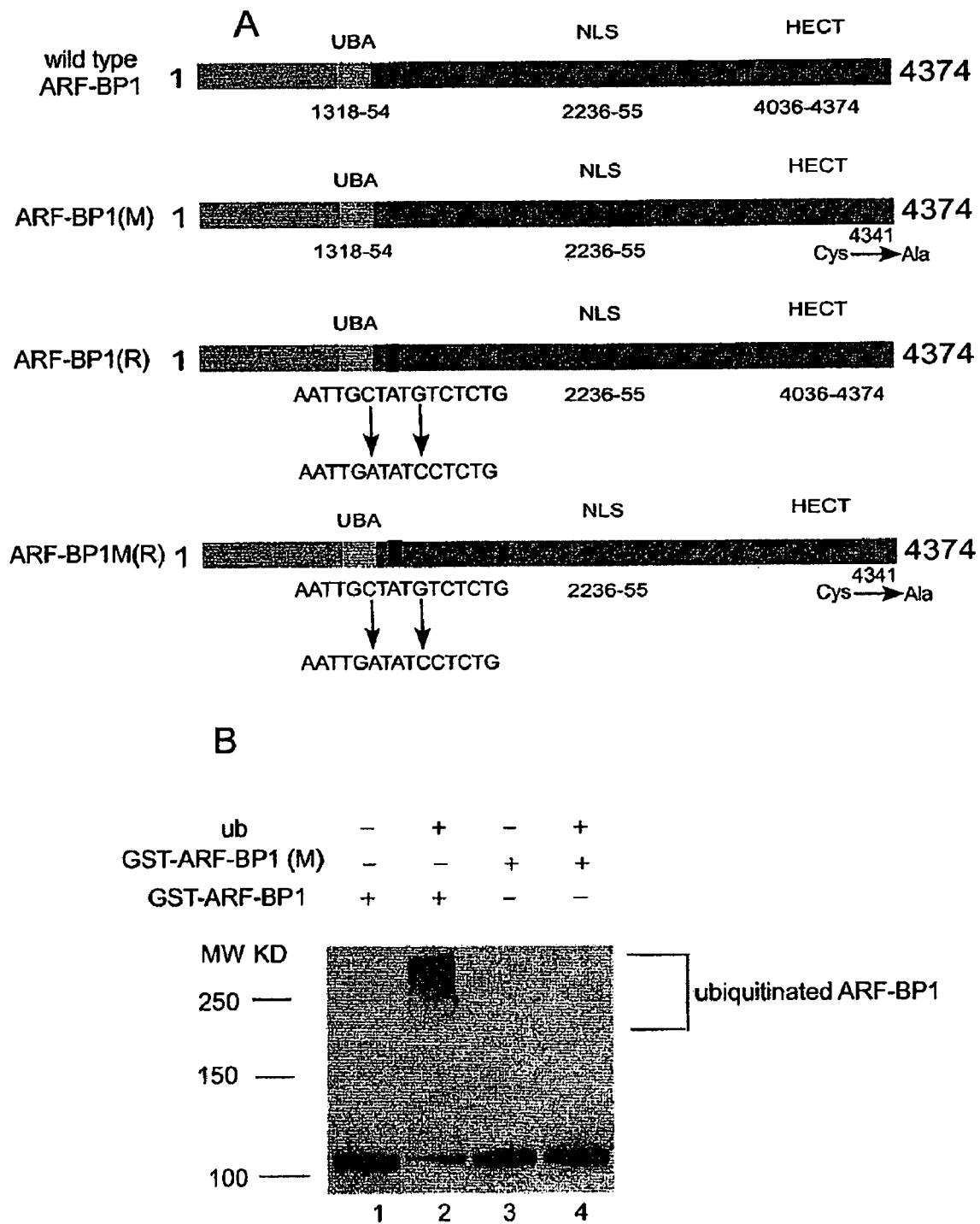
FIGS. 14A-D demonstrate that the HECT domain is critical for the ubiquitin ligase activity of ARF-BP1 and that re-introduction of ARF-BP1(R) abrogates cell growth arrest by ARF-BP1 RNAi in p53-null H1299 cells.
Figure 14:
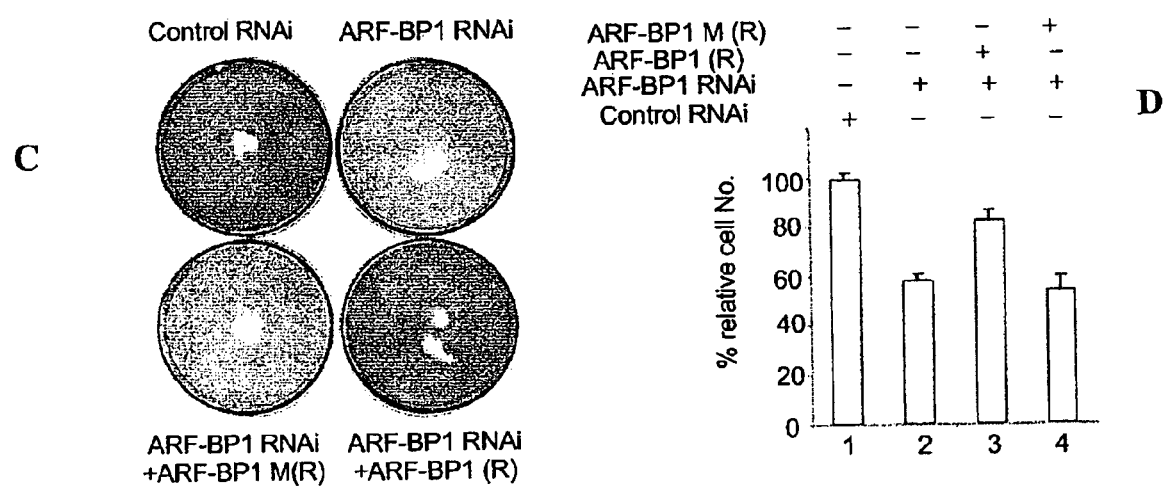

To further demonstrate the specificity of ARF-BR-RN1-mediated effects, rescue experiments were performed. A new expression vector for ARF-BP1 which contains a point mutation at the RNAi#1 targeting region (ARF-BR1(R) was made (FIG. 14). This mutant was immune to the effect by the ARF-BP1 RNAi#1. To further elucidate the importance of ubiquitin ligase activity of ARF-BP1 another mutant (ARF-BP1 M (R) was made, in which the conserved Cystine residue at the HECT domain was replaced by Alanine (FIG. 14A). Via in vitro ubiquitination assay, it was confirmed that this mutation at the HECT domain abrogates the ubiquitin ligase activity of ARF-BP1 (FIG. 14B).

To perform the "rescue experiments", the RNAi assay in U2OS cells with ARF-BP1-RNAi#1 was employed. Rescue was attempted by expressing the ARF-BP1 mutant (ARF-BP1 (R)). As indicated in FIG. 9D, after the ARF-BP1 RNAi#1 treatment, endogenous p53 was stabilized and p21 was activated. ARF-BP1 (R) expression reversed the effect on the p53 stabilization and p21 induction induced by the ARF-BP1 RNAi#1 (lane 3 vs. lane 2). The HECT mutant form (ARF-BP1M(R)) which was expressed at similar levels, failed to rescue the effects (lane 4 vs. lane 2) (FIG. 9D). This approach was utilized for p53-independent function in H1299 cells. The cell growth inhibition induced by the ARF-BP1 RNAi#1 treatment was rescued by expression of ARF-BP1(R), but not the HECT mutant form (ARF-BP1M (R)). This demonstrates not only the specificity of the ARF-BP1-RNAi medicated effects but also the importance of the ubiquitin ligase activity in ARF-BP1-mediated functions.

Figure 15:
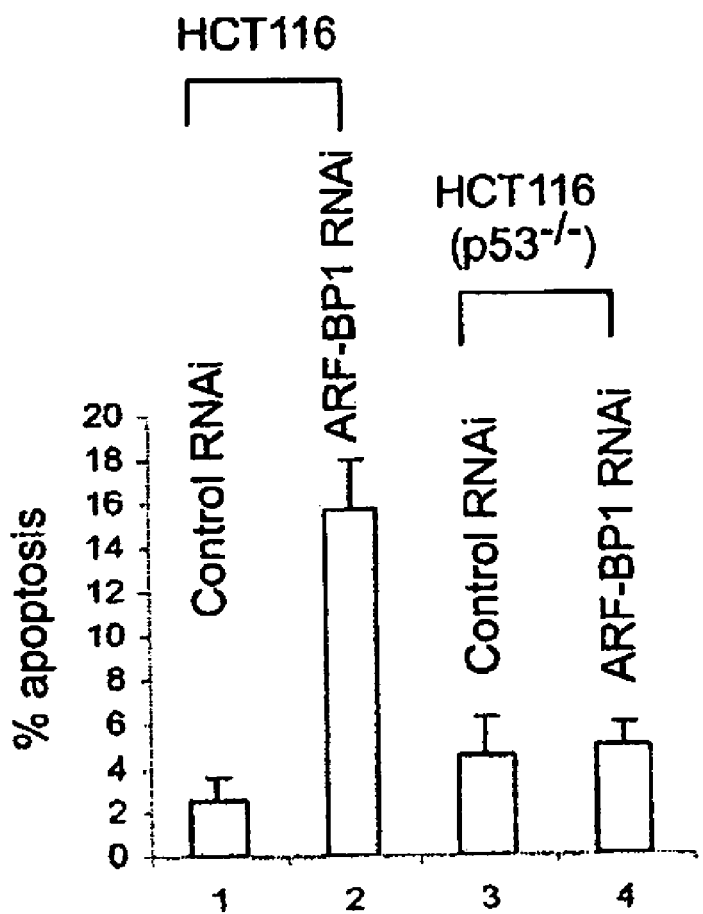
FIG. 15 is a bar graph showing that inactivation of ARF-BP1 induces p53-dependent apoptosis in HCT116 cells. Quantitation of apoptotic cells from HCT116 and HCT116-p53 (−/−) cells treated with either ARF-BP1-RNAi or control-RNAi (GFP-RNAi) where apoptotic cells were counted by FACS analysis (SubG1) and averaged from three independent experiments.

To confirm that these effects of ARF-BP1 are p53-dependent, the siRNA assay was performed in a pair of isogenic human colorectal carcinoma lines that do or do not express wild-type p53. As shown in FIG. 9E, when HCT116 parental cells and HCT116 p53(-/-) cells were subjected to RNAi treatment, ARF-BP1 knockdown stabilized p53 and induced p21 in the parental cells but not in the p53 null cells. In contrast, the levels of control proteins such as c-Mye and actin were unaffected by RNAi treatment. ARF-BP1 ablation induced apoptosis in parental HCT116 cells but not in p53-null HCT116 derivatives (FIG. 15). The steady-state levels of Mdm2 were also induced by ARF-BP1 inactivation in the parental cells, consistent with the fact that Mdm2 is a transcription target of p53. Mdm2 levels in the p53 null cells were unaffected by ARF-BP1 ablation (FIG. 9E), suggesting that inactivation of ARP-BP1 induces p53 stabilization but has no effect on Mdm2 stabilization. By demonstrating that ARF-BP1 inactivation is sufficient to stabilize and activate p53 in normal cells, these data demonstrate that the ARF/ARF-BP1 interaction contributes, at least in part, to p53 activation induced by ARF.

EXAMPLE 7

This example demonstrates that ARF-BP1 directly binds and ubiquitinates p53, and ARF-BP1-mediated ubiquitination of p53 is inhibited by ARF.

Figure 16:
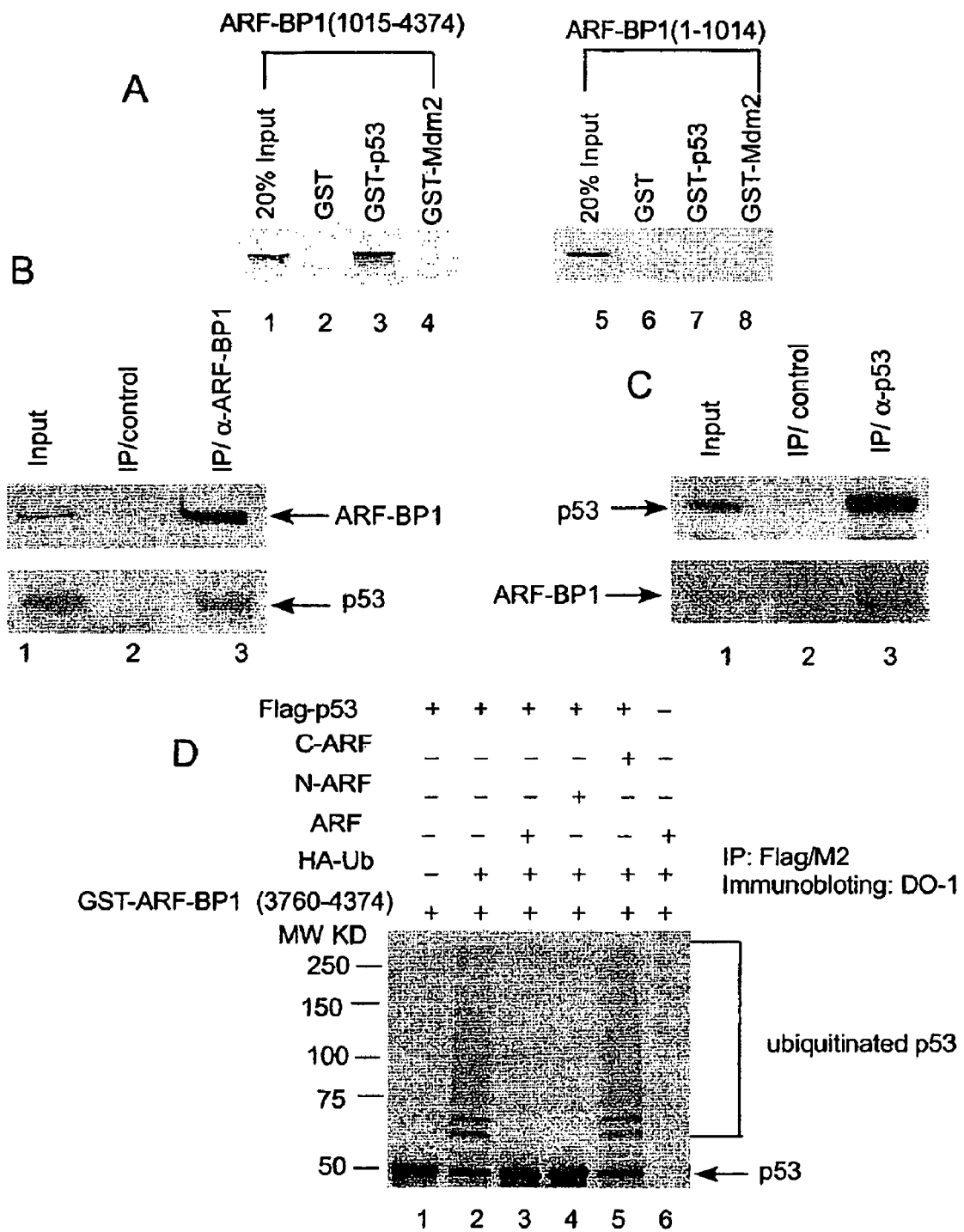
FIGS. 16A-D illustrate that ARF-BP1 binds and ubiquitates p53, and ARF-BP1-mediated ubiquitation of p53 is inhibited by ARF.

The functional relationship between p53 and ARF-BP1 was evaluated by determining whether ARF-BP1 can bind p53 in the absence of ARF. As shown in FIG. 16, $^{35}$S-labeled in vitro-translated ARF-BP1 (1015-4374) strongly bound an immobilized GST-p53 polypeptide but not GST alone (lane 3 vs. lane 2). Conversely, no significant binding was detected between ARF-BP1 and GST-Mdm2 (lane 4).

To test for the interaction between endogenous p53 and ARF-BP1 proteins in human cells, cell extracts from U2OS cells, were immunoprecipitated with α-ARF-BP1 or with control IgG. As seen in FIG. 16B, p53 was clearly detected in the immunoprecipitates obtained with the α-ARF-BP1 antiserum (lane 3) but not the control IgG (lane 2, lower panels). Conversely, endogenous ARF-BP1 was readily immunoprecipitated with the p53-specific monoclonal antibody DO-1 (lane 3, FIG. 17C), but not with a control antibody (lane 2, FIG. 16C). This data indicates that p53 can interact directly with the ARF-BP1 protein both in vitro and in vivo.

To test if ARF-BP1-mediated E3 ubiquitin ligase was involved in p53 degradation, ARF-BP1 direct induction of p53 ubiquitination in the absence of Msm2 by was examined via a standard in vitro ubiquitination assay using all purified components. Flag-p53 was incubated with GST-ARF-BP1 in the presence of HA-tagged ubiquitin (HA-Ub), E1 and an E2 (UbcH5c). The ubiquitin-conjugated p53 products of the reaction were immunoprecipitated with Flag/M2 beads and visualized by Western blot analysis with a p-53-specific antibody. As indicated in FIG. 16D, high levels of ubiquitinated p53 were generated by ARF-BP1 (lane 2). ARF-BP1 mediated p53 ubiquitination was strongly repressed in the presence of ARF (lane 3). Consistent with the binding data shown in FIG. 5A, the N-terminal region of ARF (N-ARF) retained full inhibition of ARF-BP1-mediated p53 ubiquitination whereas the C-terminal region (C-ARF) showed no effect (lanes 4 and5). These data demonstrate that ARF-BP1 is an ubiquitin ligase for p53 and that ARF-BP1 mediated ubiquitination of p53 is repressed by ARF.

EXAMPLE 8

This example demonstrates that ARF-BP1 is critical for ARF-mediated p53 stabilization in Mdm2-null cells.

Since ARF-BP1 binds and unbiquitates p53 in the absence of Mdm2, whether the ARF/BP1 interaction stabilizes p53 in an Mdm2-independent manner was evaluated. To determine whether ARF expression induces p53 stabilization in Mdm2-null cells, p53/Mdm2 double-null MEF cells were transfected with expression vectors encoding p53 alone, or both p53 and ARF. p53 protein levels were significantly elevated in these cells by ARF overexpression (FIG. 17A), indicating that ARF stabilizes p53 in an Mdm2-independent manner.

Figure 17:
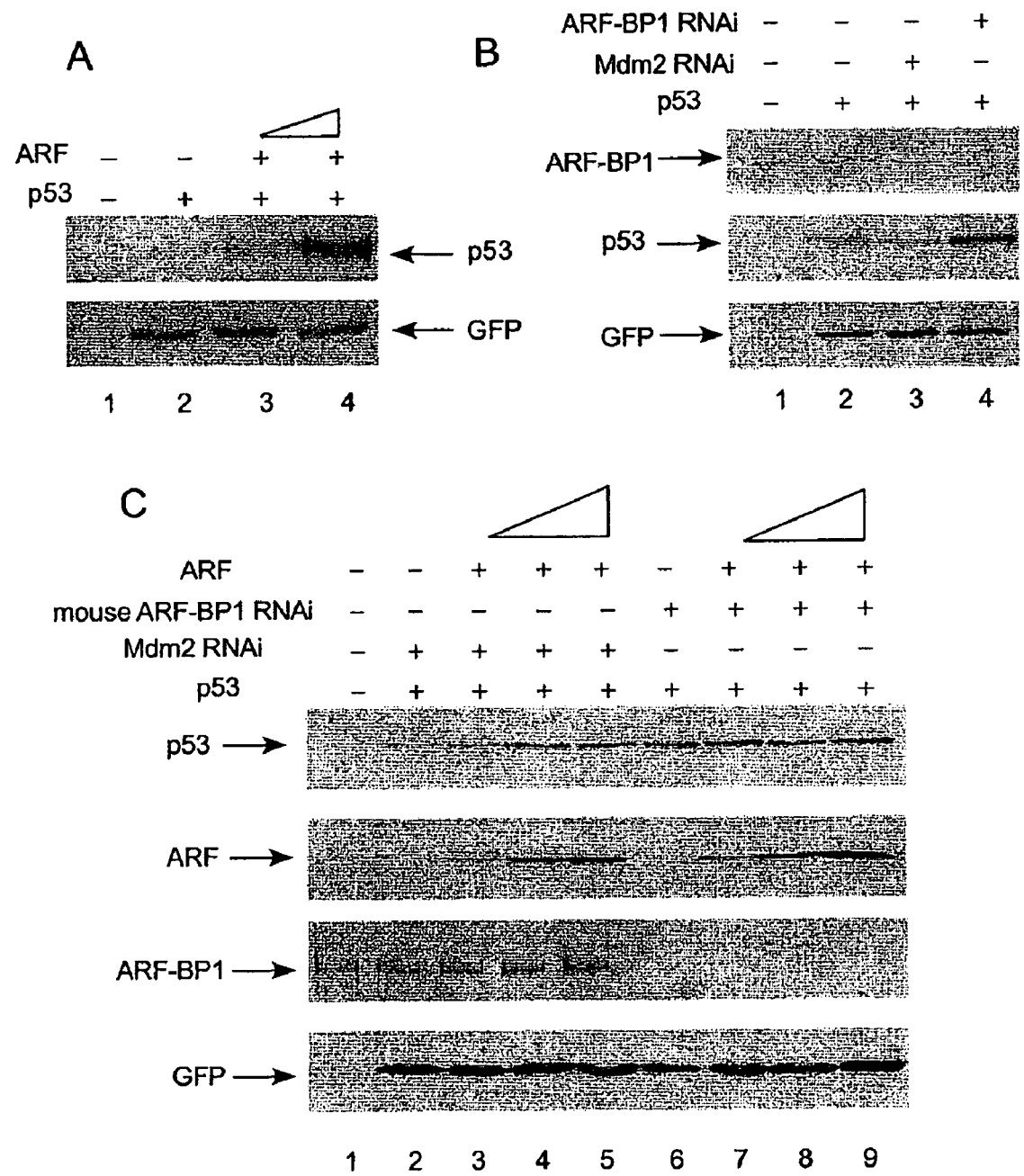
FIGS. 17A-C demonstrate that ARF induces p53 stabilization in an Mdm2-independent manner, and ARF-BP1 is critical for ARF-mediated p53 stabilization in Mdm2-null cells.
Figure 18:
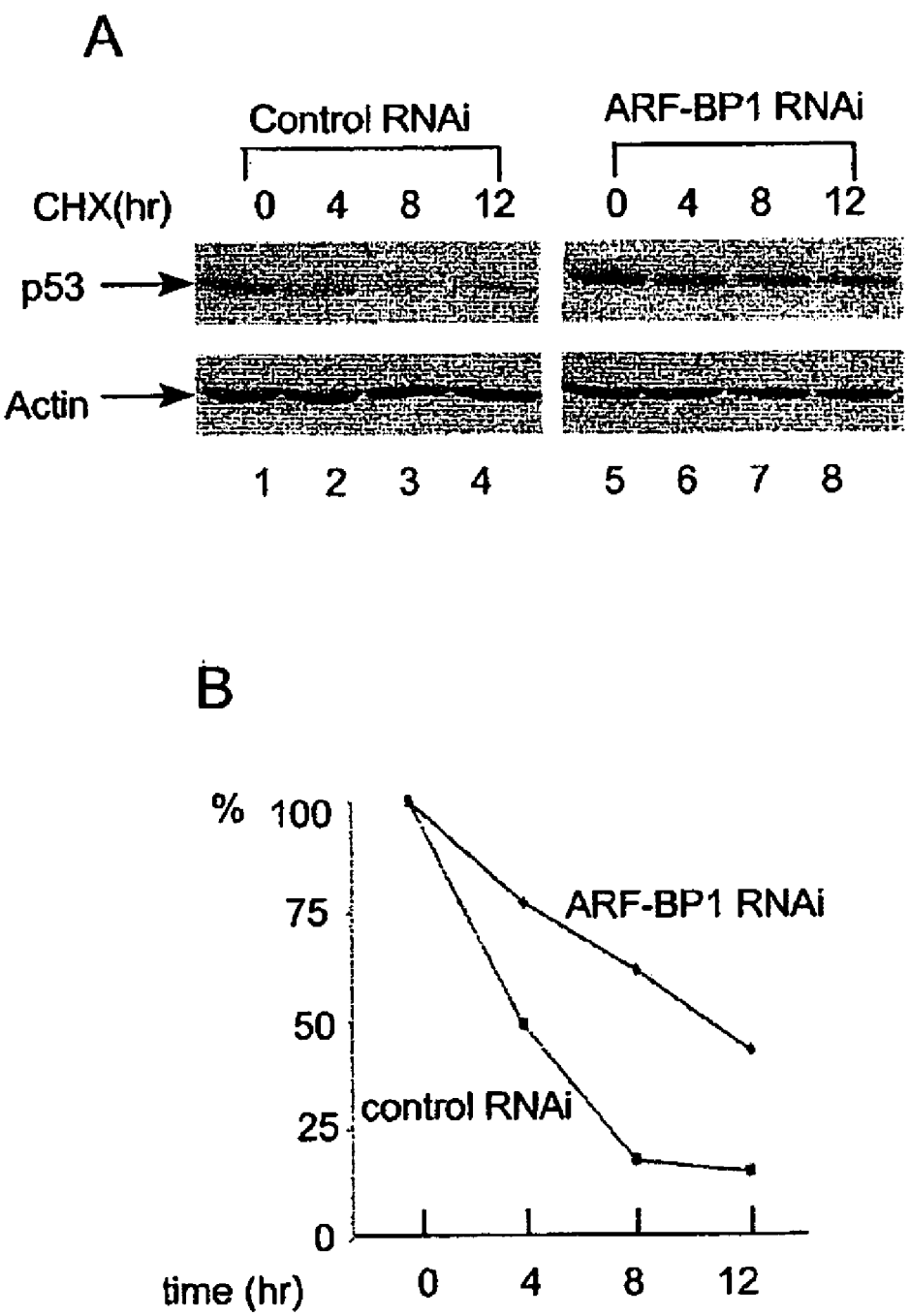
FIGS. 18A-B demonstrate that inactivation of ARF-BP1 extends the half-life of transfected p53 protein.

The role of endogenous ARF-BP1 in p53 degradation in the absence of Mdm2 was verified by examination of whether inactivation of ARF-BP1 is sufficient to stabilize p53 in Mdm2-null cells. Mdm2/p53 double null cells were co-transfected with a p53 expression vector and siRNA specific for either ARF-BP1 or Mdm2. Ablation of endogeneous ARF-BP1 expression in the cells caused a marked stabilization of p53 (FIGS. 17B and 18A and B). Treatment with Mdm2-specific siRNAs had no effect on p53 levels in Mdm2/p53-null cells (lane 3, FIG. 17B), confirming the specificity of p53 stabilization by ARF-BP1 inactivation.

To provide direct evidence that ARF-BP1 is involved in the Mdm2-independent p53 stabilization induced by ARF, the requirement for ARF-BP1 for ARF-mediated p53 stabilization in Mdm2-null cells was examined. p53/Mdm2 double-null cells were co-transfected with ARF-BP1-specific siRNAs and expression vectors encoding p53 and ARF. As indicated in FIG. 17C, the p53 stabilization induced by ARF was clearly attenuated in ARF-BP1 knockdown cells (lanes 6-9), indicating that ARF-BP1 is critical for ARF-mediated p53 stabilization in these cells. In contrast, ARF-mediated p53 stabilization was intact in cells treated with Mdm2 RNAi (lanes 2-5, FIG. 17C). These results indicate that ARF-BP1 is critical for the ARF-mediated, Mdm2-independent, stabilization of p53.

EXAMPLE 9

This example demonstrates that NPM/B23 protein is not the enzymatic target of the ARF-BP1 ubiquitin ligase activity.

Figure 21:
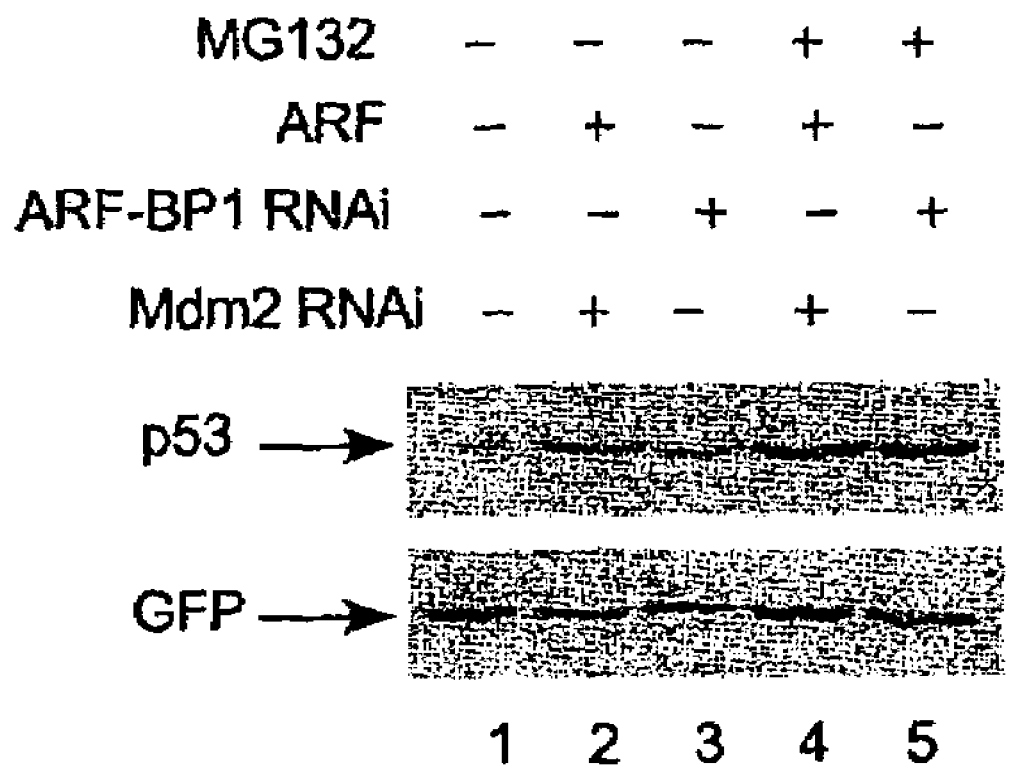
FIG. 21 demonstrates that ARF-BP1 does not target the NPM/B23 protein for degradation and that the NPM/B23 protein is not the enzymatic target of the ARF-BP1 ubiquitin ligase activity. Proteasome inhibition stabilized p53 beyond what is achieved by ARF or ARF-BP1 RNAi as shown via Western blot analysis of cell extracts from MEF p53/Mdm2-double null cells transfected with expression vectors of p53 and ARF (lane 2, 4), together with either ARF-BP1 RNAi (lane 3, 5) or Mdm2 RNAi (lane 2, 4), by anti-p53 (DO-1) and anti-GFP antibodies.
Figure 22:
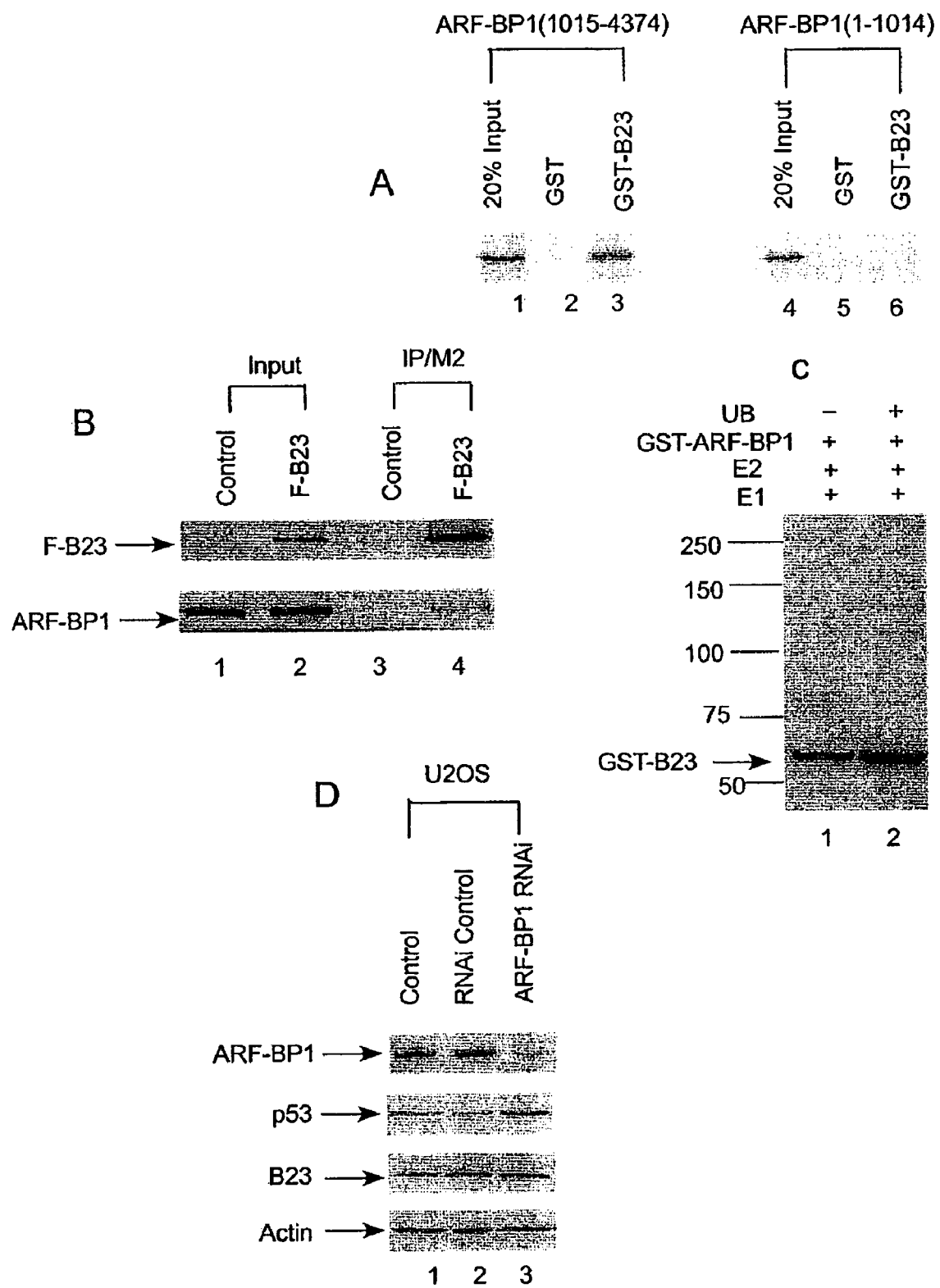
FIGS. 22A-D illustrate that ARF-BP1 interacts with B23 in vivo and in vitro, but does not ubiquitinate and degrade B23.

Several recent studies have indicated that NPM/B23 might be the key target for p53-independent functions mediated by ARF (Bertwistle et al., *MCB* 23:8097, 2004; Kuo et al., *Genes Dev.* 18:1862, 2004). Additionally, the data in FIG. 1C shows that NPM/B23 is the major component of the ARF-associated nuclear complexes. To examine how ARF-BP1 loss leads to cell cycle arrest in p53 null cells and whether there are other targets of its E3 activity, as well as whether ARF-BP1 induces degradation of NPM/B23 for p53-independent functional regulation, a series of experiments were conducted. The results are shown in FIGS. 21 and 22. Using the GST-pull-down-assay (FIG. 22A), NPM/B23 was found to interact directly with ARF-BP1. Using the coimmunoprecipitation assay to assess the in vivo interaction between ARF-BP1 and NPM/B23 (FIG. 22B), it was found via Western blot analysis that endogenous ARF-BP1 is coimmunosuppressed with B23. After transfecting the expression vector of Flag-B23 into 293 cells, the B23 protein was immunoprecipitated by M2-beads. To examine whether NPM/B23 is a substrate of ARF-BP1, the enzymatic activity of ARF-BP1 was determined using an in vitro assay. The NPM/B23 polypeptide, which was expressed in bacteria and purified to near homogeneity, was incubated with GST-ARF-BP1 in the presence of ubiquitin, E1, and an E2 (UbcH5C). As shown in FIG. 22C, no significant ubiquitination of NPM/B23 was detected by Western blot analysis with the anti-NPM/B23 antibody. These results indicate that ARF-BP1 fails to induce ubiquitination of NPM/B23. Consistent with the above results, RNAi-mediated knock-down of endogenous ARF-BP1 had no effect on the stability of endogenous NPM/B23 as shown in FIG. 22D. These results indicate that ARF-BP1 is not involved in NPM/B23 degradation. These results further indicate that NPM/B23 is not the enzymatic target for ARF-BP1 ubiquitin ligase activity.

While the foregoing invention has been described in some detail for purposes and understanding, it will be appreciated by one skilled in the art, from a reading of sure, that various changes in form and detail can be made without departing from cope of the invention in the appended claims.

What is claimed is:

1. An isolated ARF-BP1 polypeptide having the amino acid sequence of SEQ ID NO: 2.

2. A method for identifying an inhibitor of p53-ARF-BP1 interaction, comprising the steps of: (a) obtaining or generating an in vitro system comprising p53 and an ARF-BP1 polypeptide having the amino acid sequence of SEQ ID NO:2; (b) contacting the in vitro system with a candidate inhibitor; and (c) determining if the candidate inhibitor inhibits p53-ARF-BP1 interaction in the in vitro system.

3. The method of claim 2, wherein the determination in step (c) is made by comparing p53-ARF-BP1 interaction in the in vitro system of step (b) with p53-ARF-BP1 interaction in a second in vitro system comprising p53 and an ARF-BP1 polypeptide having the amino acid sequence of SEQ ID NO:2 in the absence of the candidate inhibitor.

4. The method of claim 2, wherein the determination in step (c) is made by comparing p53-ARF-BP1 interaction in the in vitro system of step (b) with p53-ARF-BP1 interaction in a second in vitro system comprising p53, an ARF-BP1 polypeptide having the amino acid sequence of SEQ ID NO:2, the candidate inhibitor, and an anti-p53 or anti-ARF-BP1 antibody.

5. A method for identifying an agent that inhibits the binding between ARF-BP1 and p53, comprising the steps of: (a) contacting a candidate agent with p53, in the presence of an ARF-BP1 polypeptide having the amino acid sequence of SEQ ID NO:2; and (b) assessing the ability of the candidate agent to inhibit p53-ARF-BP1 interaction.

6. A method for identifying an agent that inhibits the binding between ARF and ARF-BPI, comprising the steps of: (a) contacting a candidate agent with an ARF-BP1 polypeptide having the amino acid sequence of SEQ ID NO:2, in the presence of ARF; and (b) assessing the ability of the candidate agent to inhibit ARF-BP1-ARF interaction.

* * * * *

SEQUENCE LISTING

```
<160> NUMBER OF SEQ ID NOS: 22

<210> SEQ ID NO 1
<211> LENGTH: 13128
<212> TYPE: DNA
<213> ORGANISM: homo sapiens
<220> FEATURE:
<221> NAME/KEY: misc_feature
<222> LOCATION: (3370)..(3372)
<223> OTHER INFORMATION: CODES FOR A PROLINE AS COMPARED TO A LEUCINE AT
      AMINO ACID RESIDUE 1124 OF SEQ ID NO:2
<220> FEATURE:
<221> NAME/KEY: misc_feature
<222> LOCATION: (7918)..(7920)
<223> OTHER INFORMATION: CODES FOR A LYSINE AS COMPARED TO A THREONINE
      AT AMINO ACID RESIDUE 2640 OF SEQ ID NO:2
<220> FEATURE:
<221> NAME/KEY: misc_feature
<222> LOCATION: (7921)..(7923)
<223> OTHER INFORMATION: CODES FOR A PHENYLALANINE AS COMPARED TO A
      LEUCINE AT AMINO ACID RESIDUE 2641 OF SEQ ID NO:2
<220> FEATURE:
<221> NAME/KEY: misc_feature
<222> LOCATION: (7924)..(7926)
```

```
<223> OTHER INFORMATION: CODES FOR A VALINE AS COMPARED TO A SERINE AT
      AMINO ACID RESIDUE 2642 OF SEQ ID NO:2
<220> FEATURE:
<221> NAME/KEY: misc_feature
<222> LOCATION: (7927)..(7929)
<223> OTHER INFORMATION: CODES FOR A CYSTEINE AS COMPARED TO A SERINE AT
      AMINO ACID RESIDUE 2643 OF SEQ ID NO:2
<220> FEATURE:
<221> NAME/KEY: misc_feature
<222> LOCATION: (9955)..(9957)
<223> OTHER INFORMATION: CODES FOR AN ASPARTIC ACID AS COMPARED TO A
      GLYCINE AT AMINO ACIDRESIDUE 3319 OF SEQ ID NO:2
<220> FEATURE:
<221> NAME/KEY: misc_feature
<222> LOCATION: (11293)..(11295)
<223> OTHER INFORMATION: CODES FOR AN ALANINE AS COMPARED TO A VALINE AT
      AMINO ACID RESIDUE 3765 OF SEQ ID NO:2

<400> SEQUENCE: 1
atgaaagtag acaggactaa actgaagaag acacctactg aggctcctgc agactgcaga      60
gccttaatag acaaactcaa agtttgtaat gatgagcaac ttctcttgga actgcagcag     120
atcaaaacat ggaacattgg aaagtgcgag ttatatcact gggtggacct gttggaccgc     180
ttcgatggaa tactggcaga tgctggacag acagtggaga atatgtcatg gatgctcgta     240
tgtgataggc cagaaagaga gcaactgaaa atgcttctct ggctgtgtt gaacttcaca      300 gccttgctca ttgagtacag cttttcccgg catctgtaca gttccataga gcatttgaca     360
actttattgg cttcctctga tatgcaagtg gtgctggcag tcctcaatct cctatatgta     420
tttagcaaaa gatcaaacta catcactcgt ctgggatctg acaagaggac cccgctgcta     480
actcggctac aacatttggc agagagctgg ggtggaaagg agaatggctt tggacttgca     540
gaatgttgca gagacttgca tatgatgaaa tatccaccca gtgcaactac actcactttt     600
gaattctatg cagatcctgg ggccgaggtc aaaattgaga aaggacaac tagtaacaca      660 ctacattata ttcacataga gcaacttgac aagatttcag aaagcccttc tgaaatcatg     720
gaatctctta ccaaaatgta cagcattcct aaggataagc agatgctgtt atttacacac     780
atacgactgg cccatggctt ttctaatcac aggaagcgat gcaggcagt tcaggccaga      840 ctgcatgcaa tatctatatt agtgtattcc aatgccttgc aggaatcagc aaacagtatc     900
ttgtataatg gcttgataga ggagttggta gatgtccttc agataacgga taagcagctt     960
atggagatta aagcagcttc tttacgaaca ttaacatcaa ttgtccactt ggagagaact    1020
cccaaactca gcagtattat tgactgtact ggaactgcct cctaccatgg atttttgcca    1080
gtgcttgtaa ggaactgtat ccaggccatg attgatcctt ccatggatcc ataccctcac    1140
cagtttgcca ctgctctctt ctctttttta taccatctgg ccagctacga tgctggtggt    1200
gaagccttgg tctcctgtgg aatgatggaa gccttattga aggtcataaa gtttcttggc    1260
gatgaacagg accagataac atttgtcacc agagccgtca gagtggttga ccttatcacc    1320
aacctggata tggcagcttt tcaatcccat agtggacttt ctatcttcat ttatagactt    1380
gagcatgaag tagatttgtg ccgaaaagaa tgtccgtttg tgatcaagcc aaagatccag    1440
agacccaata ctacacaaga aggagaggaa atggaaactg atatggatgg agtccagtgt    1500
attccacaac gagcagcact tctgaaatcc atgttgaatt cctcaagaa ggccatccaa     1560 gaccctgctt tctcagatgg catacgacat gtgatggatg gttctctgcc tacctccctg    1620
aaacacatca tcagcaatgc agaatactat ggcccatcac tcttcctcct agctactgaa    1680
gtggtgactg tgtttgtatt tcaagaacca tcactgctct cctcactcca ggacaatgga    1740
ttgacagatg tcatgctgca tgcactgctt atcaaagatg ttcctgctac ccgtgaagtc    1800
```

```
cttggctccc tcccaaatgt attcagtgca ctctgtttga atgcccgagg tcttcagtct    1860
tttgttcagt gtcagccttt tgaacgcctc ttcaaagttc ttctgtctcc agattacctc    1920
ccagccatgc ggaggaggag aagttctgat cccttgggg atactgcatc caacctgggg     1980
agtgctgtcg atgagctcat gagacatcag cccacccta aaacagatgc aacgactgcc     2040
atcatcaagt tacttgaaga atctgtaat cttggaaggg accccaaata catctgtcag     2100
aagccatcaa tccagaaggc agatggcact gccactgctc ctccccaag gtctaatcat     2160 gccgcagaag aagcctctag tgaggatgag aggaagagg aagtacaggc catgcagagc      2220
tttaattcta cccagcaaaa tgaaactgag cctaatcagc aggttgttgg tacagaggaa     2280
cgtattccta ttcccctcat ggattacatc cttaatgtga tgaaatttgt ggaatctatt     2340
ctgagcaaca atacaacaga tgaccactgc caggaatttg tgaatcagaa aggactgttg     2400
cctttggtta ccattttggg tcttcccaat ctgcccattg actttccac atctgctgcc      2460 tgtcaggctg ttgcaggtgt ctgcaaatcc atattgacac tgtcacatga acccaaagtc     2520
cttcaagagg gtctccttca gttggactcc atcctctcct ccctggagcc cttacaccgc     2580
cccattgaat cccctggggg ctcagtgttg ttgcgagaac tggcttgcgc aggcaatgtt     2640
gctgatgcta ccctctcagc ccaggccaca cctctgctgc atgcactcac tgctgcccat     2700
gcctacatca tgatgtttgt tcatacttgc agagttggac agagtgaaat tcgttccatc     2760
tccgtaaacc agtggggctc tcaattgggt ctgagtgttt tgagcaagct gagccagtta     2820
tactgttccc tggtgtggga aagcactgtc ctcctctctc tgtgtacccc aaacagccta     2880
ccatctgggt gtgaatttgg ccaggcagat atgcagaaac tggttccaaa ggatgagaag     2940
gcaggtacga cccagggcgg aaaaagatca gatggggaac aggatggagc agctggaagt     3000
atggatgctt ctacccaggg cttattagaa ggcattgggc tagatggtga cacattggct     3060
cccatggaga cagatgaacc tactgcttca gactctaagg gcaaatctaa aatcacacca     3120
gcaatggctg ccagaattaa gcaaatcaag cctttgttat cagcttcctc cagattaggc     3180
cgagcacttg ctgagctatt tggacttctt gttaaacttt tgtgtgggatc tcctgtccgc    3240 cagagaagga gccatcatgc tgccagcacc actacagcac cgacacctgc cgcgcgatca     3300
acagcctcag ctctcactaa gctcttgact aaggggttat cttggcagcc cccaccatat     3360
acacctactc cccgattcag gctgacattc ttcatctgtt cagttggttt cacatcccca     3420
atgctgtttg atgagaggaa gtatccctac cacctcatgc tgcaaaaatt tctctgctcc     3480
ggaggccaca atgctctttt tgaaactttc aactgggctc tgtccatggg aggtaaagtt     3540
cctgtttctg agggattgga acactcagac ttgcctgatg gcacaggaga attcctagat     3600
gcctggctta tgctggtgga agatggtg aatcccacca cggtgcttga atctccacat       3660
tcgctgcctg ccaaattgcc tggaggtgtc cagaactttc cccagttcag tgcactgcgc     3720
ttccttgtgg taactcagaa agcagccttt acttgcatca aaaacttatg gaaccggaaa     3780
cccctgaagg tatatggtgg acgaatggct gaatcgatgc tggccattct atgccacatc     3840
ctccgaggag aacctgtgat tcgagagaga ctaagcaagg agaaggaggg gtctcgagga     3900
gaagaggata cagggcaaga ggaaggtggc tcccgccggg aacctcaagt caaccagcaa     3960
caactgcaac agctcatgga catgggcttc acaagggaac atgcaatgga ggcactgttg     4020
aacaccagca ccatggagca ggccacagag tacctttaa cccacccctcc tccaatcatg     4080 ggaggagttg ttcgggatct cagcatgtct gaagaggacc agatgatgag agcaattgct     4140
```

```
atgtctctgg gacaggatat tccaatggat caaagggcag agtcacctga ggaagttgct    4200
tgccggaagg aggaagagga acggaaagct cgggaaaagc aggaggagga agaggctaaa    4260
tgtctagaga agttccagga tgctgacccg ttggaacaag atgagctcca cactttcaca    4320
gatactatgt tgccaggctg cttccacctt cttgatgagc tgccagacac agtataccgt    4380
gtgtgtgacc tgatcatgac agcaatcaaa cgtaatggag cagattatcg tgacatgatt    4440
ctgaagcaag tagtcaatca ggtgtgggaa gctgctgatg tattgatcaa agctgctctt    4500
cccctgacaa caagtgacac aaaaaccgtg tcagagtgga taagtcagat ggccacactg    4560
ccccaggcct ccaatttggc tactagaatc ttgcttttaa cgctactttt tgaggagttg    4620
aagctacctt gtgcttgggt ggttgaatca agtggcatcc ttaatgtcct aatcaaactc    4680
ttggaagtgg ttcagccctg cctccaggca gccaaggagc agaaggaagt ccagacccca    4740
aagtggatca caccagtgtt gctcctgatt gatttctatg aaaagacagc catctcctca    4800
aaaaggagag cccagatgac taagtacctg caatccaaca gcaacaactg cgctggttt     4860 gatgatcgct ctgggcgttg gtgtagttac agtgcaagca acaatagcac tattgattct    4920
gcctggaaat ctgagagac aagcgtgcga ttcactgcag gccgaagaag atacacggtc     4980
caattcacta caatggtgca ggttaatgag gaaacaggga accgacgccc tgtgatgctg    5040
actctcctca gggtacctcg gctgaataaa aattcaaaaa acagcaatgg acaggaacta    5100
gagaagacgc tggaagaaag caagaaatg gatatcaaac gtaaagaaaa taaaggcaat     5160
gatacccctt tggccctaga gagtacaaac actgaaaagg agacaagcct ggaggaaaca    5220
aaaatcgggg agatcctgat ccagggcttg acagaagata tggtgactgt tttaatccgg    5280
gcctgcgtga gcatgctggg agtccctgtg gacccagata cttgcatgc cacccttcgt     5340 ctctgtctga ggctcacccg ggaccacaaa tatgccatga tgtttgcaga actgaagagt    5400
acccgcatga tcttgaattt gacccagagc tcaggcttca atgggtttac tccctggtc    5460 acccttctct taagacacat cattgaggac ccctgtaccc ttcgtcatac catggaaaag    5520
gttgttcgct cagcagctac aagtggagct ggtagcacta cctctggtgt tgtgtctggc    5580
agcctcggct ctcgggagat caactacatc cttcgtgtcc ttgggccagc cgcatgccgc    5640
aatccagaca tattcacaga agtggccaac tgctgtatcc gcatcgccct tcctgccct     5700 cgaggctcag gaactgcttc agatgatgaa tttgagaatc ttagaattaa aggccctaat    5760
gctgtacagc tggtgaagac caccccttg aagccctcac ctctgcctgt catccctgat     5820
actatcaagg aagtgatcta tgatatgctg aatgctctgg ctgcatacca tgctccagag    5880
gaagcagata atctgatcc taaacctggg gttatgaccc aagaggttgg ccagctcctg     5940
caagacatgg gtgatgatgt ataccagcag taccggtcac ttacgcgtca gagcagtgac    6000
tttgatacgc agtcaggttt ttccattaat agtcaggtct ttgctgcaga tggtgcctcc    6060
actgagactt ccgcatctgg gacctcccaa ggagaggctt caactccaga ggagtctcga    6120
gatgggaaga agataaaga agggaccgg gcctctgagg aaggcaaaca gaaaggcaag      6180
ggcagcaaac ctttaatgcc tacctccact atccttcgtc ttctggcaga gttggtgagg    6240
tcctatgttg gtattgctac cctgattgcc aactacagct acactgtggg ccagtctgaa    6300
ctgatcaaag aggactgcag tgtgctagct tttgttctgg accacctgct cccacatacc    6360
cagaatgcag aagacaagga caccctgcc ttgcccgcc tgttcctcgc aagcctggct      6420
gctgcaggga gtggcacaga tgcccaggtg gccctagtga atgaagtaaa agcagccctt    6480
ggacgggcac tggctatggc tgagagtaca gagaaacatg ccaggcttca ggcagtgatg    6540
```

-continued

```
tgtatcatca gtactatcat ggagtcctgc ccctccacct ccagcttcta cagcagtgcc    6600
acagcgaaga cccagcacaa tggcatgaac aacatcattc ggcttttcct gaagaaggga    6660
ctggttaatg acctggccag agtacctcac agcttagacc tgtccagtcc caacatggcc    6720
aacacagtca atgctgctct gaagcctttg gaaacacttt cccggattgt gaaccagccc    6780
agtagccttt ttggcagcaa gagtgcttct agcaagaaca agtctgagca ggatgcccaa    6840
ggagcctctc aagattccag tagcaaccag caggacccag gcgagcctgg ggaagcagaa    6900
gtgcaggagg aggatcatga tgtcactcag acagaggtgg cagatgggga tatcatggat    6960
ggggaggctg aaaccgactc agtggtgatt gctgggcagc tgaggtgct cagttcacaa     7020 gagatgcagt tgagaatga gctggaggac ctgatagatg agttgcttga gagggatggc    7080
ggatctggga acagtacaat tatagtgagc agaagtggag aggatgaatc acaagaggac    7140
gtgctgatgg atgaagctcc ttccaacctc agccaagctt ccaccttgca ggccaaccga    7200
gaagattcca tgaatatcct ggaccctgag gatgaggagg agcacactca ggaagaggac    7260
agcagtggca gtaacgagga tgaggatgat agtcaggatg aagaggagga ggaggaggaa    7320
gatgaggaag atgatcagga ggatgatgaa ggtgaagagg gagatgaaga cgatgacgac    7380
gatggctctg agatgaatt ggatgaggat tatcctgata tgaacgcttc tcccttggtc     7440
cgatttgagc gctttgaccg ggaggatgat ctcatcattg agtttgacaa catgttctcc    7500
agtgctacag acatccccc atccccagga aatatcccta ccacccatcc actgatggtg     7560
cgccatgcag accacagttc tctgacactg ggcagtggct cttcaacaac tcgtctcacc    7620
cagggcatcg ggcgcagtca gaggacccta aggcagctga cggccaatac tggccacacc    7680
attcatgttc actaccctgg gaatcgccag cccaaccctc ctcttatact gcagaggttg    7740
cttggtccct cagctgctgc tgacatcctt cagctgagca gcagccttcc cctacaaagc    7800
cggggtcggg cccgcctcct ggtaggcaac gatgacgtcc acatcatcgc ccgttctgat    7860
gatgagctgc tggatgactt tttccatgat cagagcacag ctaccagcca agcaggcaag    7920
tttgtgtgca tccccacagc cctgacccgc tggacagaag aatgcaaagt tctcgatgct    7980
gagagcatgc atgactgtgt ttcagtggtt aaagtgtcca ttgtcaatca cctggaattc    8040
ctgagggatg aggagctgga agaaaggcga gagaagcgca ggaaacaact ggctgaggaa    8100
gaaacaaaga taactgataa aggcaaagaa gataaggaga cagggatca gagtgcacag    8160 tgtactgcat ctaagtcaaa tgactccact gaacagaatc tctcagatgg gacgcctatg    8220
cctgacagct acccaacaac cccatcttca actgatgcag ctacatctga gtccaaggag    8280
acccttggca ctctgcaatc ctcacaacag caaccaacac tcccaacccc accagctttg    8340
ggagaggttc ctcaggagct gcagtctcca gctggagaag ggggcagctc tacacagcta    8400
ttgatgcctg tagagccaga ggaattgggt cccacaaggc caagtgggga agcagaaaca    8460
actcagatgg agttatcccc agctcccact ataacctcac tttccccaga gagagctgag    8520
gattctgatg cactgacggc tgtcagcagt cagctagaag gctctcctat ggatacaagc    8580
agcctggctt cctgtacctt agaggaggct gtgggtgaca cttcagcagc tggcagttct    8640
gagcagccca gagcaggcag ctccactcct ggggatgccc caccagctgt ggcggaagtg    8700
caaggcagga gtgatgggtc aggggaatct gcccagccac ctgaggacag ctcccccacct    8760 gcatcctctg agagctcttc caccagagat tctgccgtgg ccatttctgg agcagattcc    8820
cgaggaatcc tagaagagcc gttgccttca acaagcagtg aagaagaaga tcccctcgcg    8880
```

```
ggtatcagtc tccctgaagg tgtggacccc tcttttctgg ctgccctgcc tgatgacatc    8940
cgtcgggaag ttctacagaa ccagctaggc attcgtccac caacccggac tgcccctcc     9000 acaaatagct cagcgcctgc agtggtgggg aatcctggtg tgactgaagt gagccctgag    9060
tttctggctg ccctgcctcc agccattcag gaggaagtac tggcacagca gagagctgag    9120
cagcagcgac gagaactagc acagaatgcc agctcagaca cccctatgga ccctgtgacc    9180
ttcatccaga ctctgccctc agacctgcgc cgtagtgtcc tagaggatat ggaggacagt    9240
gtgttagctg tgatgccacc tgacattgca gctgaggctc aagccctgag acgagagcaa    9300
gaagcccggc agcgacagct catgcatgag cgtctgtttg ggcacagtag cacctccgca    9360
ctctctgcta ttctccgaag cccggctttc accagtcgct taagtggcaa ccgtggggtc    9420
cagtatactc gccttgctgt gcagagaggt ggcaccttcc agatgggggg tagcagcagc    9480
cataacaggc cttctggcag taatgtagat actctcctcc gcctccgagg acggctcctt    9540
ctggaccacg aagcccttc ttgtctcttg gtcctacttt ttgtggatga gccaaagctc     9600
aatactagcc gtctacaccg agtactgaga aatctctgct accatgccca gacccgccac    9660
tgggtcatcc gcagtctgct ctccatcttg cagcgcagca gtgagagtga gctatgcatt    9720
gaaacaccca aactcactac aagtgaggaa aagggcaaaa agtcgagcaa gagctgtggg    9780
tcaagtagcc atgagaaccg tcccctggac ctgctacaca agatggagtc aaagagctcc    9840
aaccagcttt cctggctctc agtatccatg gatgcagccc taggctgcag gactaatata    9900
tttcagatcc agcgttcagg ggggcgtaaa cataccgaga agcatgcaag cggtgactcc    9960
accgtccaca tccatcccca agctgcacct gttgtctgca gacacgtttt ggatacactc   10020
attcaattgg ccaaggtatt tcccagccac ttcacacagc agcggaccaa agaaacaaac   10080
tgtgagagtg atcgggaaag gggcaataag gcctgtagcc catgctcctc acagtcctcc   10140
agcagtggca tttgcacaga cttctgggac ttattggtaa aactggacaa catgaatgtc   10200
agccggaaag gcaagaactc cgtgaagtca gtgccagtga gcgctggcgg tgagggggaa   10260
acctctccat acagcctcga ggcctctcca ctggggcagc tcatgaacat gttgtcacac   10320
ccagtcatcc gccggagctc tctcttaact gagaaactcc tcagactcct ttctctcatc   10380
tcaattgctc tcccagaaaa caaggtgtca gaagcacagg ctaattctgg cagcggtgct   10440
tcctccacca ccactgccac ctcaaccaca tctaccacca ccaccactgc cgcctccacc   10500
acgcccacac cccctactgc acccaccccct gtcacttctg ctccagccct ggttgctgcc   10560
acggctattt ccaccattgt cgtagctgct tcgaccacag tgactacccc cacgactgct   10620
accactactg tttcaatttc tcccactact aagggcagca atctccagc gaaggtgagt     10680 gatgggggca gcagcagtac agactttaag atggtgtcct ctggcctcac tgaaaaccag   10740
ctacagctct ctgtagaggt gttgacatcc cactcttgtt ctgaggaagg cttagaggat   10800
gcagccaacg tactactgca gctctcccgg ggggactctg gacccggga cactgttctc     10860 aagctgctac tgaatggagc ccgccatctg ggttataccc tttgtaaaca aataggtacc   10920
ctgctggccg agctgcggga atacaacctc gagcagcagc ggcgagccca atgtgaaacc   10980
ctctctcctg atggcctgcc tgaggagcag ccacagacca ccaagctgaa gggcaaaatg   11040
cagagcaggt ttgacatggc tgagaatgtg gtaattgtgg catctcagaa gcgacctttg   11100
ggtggccggg agctccagct gccttctatg tccatgttga catccaagac atctacccag   11160
aagttcttct tgagggtact acaggtcatc atccagctcc gggacgacac gcgccgggct   11220
aacaagaaag ccaagcagac aggcaggcta ggttcctccg gtttaggctc agctagcagc   11280
```

-continued

```
atccaggcag ctgctcggca gctggaggct gaggctgatg ccattataca aatggtacgt    11340
gagggtcaaa gggcgcggag acagcaacaa gcagcaacgt cggagtctag ccagtcagag    11400
gcgtctgtcc ggagggagga atcacccatg gatgtggacc agccatctcc cagtgctcaa    11460
gatactcaat ccattgcctc cgatggaacc ccacaggggg agaaggaaaa ggaagaaaga    11520
ccacctgagt taccccctgct cagcgagcag ctgagtttgg acgagctgtg ggacatgctt    11580
ggggagtgtc taaaggaact agaggaatcc catgaccagc atgcggtgct agtgctacag    11640
cctgctgtcg aggccttctt tctggtccat gccacagagc gggagagcaa gcctcctgtc    11700
cgagacaccc gtgagagcca gctggcacac atcaaggacg agcctcctcc actctcccct    11760 gccccttaa ccccagccac gccttcctcc cttgacccat tcttctcccg ggagccctca    11820
tctatgcaca tctcctcaag cctgccccct gacacacaga agttccttcg ctttgcagag    11880
actcaccgca ctgtgttaaa ccagatccta cggcagtcca cgacccacct tgctgatggg    11940 cctttttgctg tcctggtaga ctacattcgt gtcctcgact ttgatgtcaa gcgcaaatat    12000
ttccgccaag agctggagcg tttagatgag gggctccgga agaagacat ggctgtgcat    12060 gtccgtcgtg accatgtgtt tgaagactcc tatcgtgagc tgcatcgcaa atccccgaa    12120 gaaatgaaga atcgattgta tatagtattt gaaggagaag aagggcagga tgctggtggg    12180
ctcctgcggg agtggtatat gatcatctct cgagagatgt ttaaccctat gtatgccttg    12240
ttccgtacct cacctggtga tcgagtcacc tacaccatca atccatcttc ccactgcaac    12300
cccaaccacc tcagctactt caagtttgtc ggacgcattg tggccaaagc tgtatatgac    12360
aaccgtcttc tggagtgcta ctttactcga tccttttaca aacacatctt gggcaagtca    12420
gtcagatata cagatatgga gagtgaagat taccacttct accaaggtct ggtttatctg    12480
ctggaaaatg atgtctccac actaggctat gacctcacct tcagcactga ggtccaagag    12540
tttggagttt gtgaagttcg tgacctcaaa cccaatgggg ccaacatctt ggtaacagag    12600
gagaataaga aggagtatgt acacctggta tgccagatga aatgacagg agccatccgc    12660 aagcagttgg cggctttctt agaaggcttc tatgagatca ttccaaagcg cctcattcc    12720 atcttcactg agcaggagtt agagctgctt atatcaggac tgcccaccat tgacatcgat    12780
gatctgaaat ccaacactga ataccacaag taccagtcca actctattca gatccagtgg    12840
ttctggagag cattgcgttc tttcgatcaa gctgaccgtg ccaagttcct ccagtttgtc    12900
acgggtactt ccaaggtacc cctgcaaggc tttgctgccc tcgaaggcat gaatggcatt    12960
cagaagtttc agatccatcg agatgacagg tccacagatc gcctgccttc agctcacaca    13020
tgttttaatc agctggatct gcctgcctat gagagctttg agaagctccg ccacatgcta    13080
ctgttggcta tccaggagtg ctctgaaggc tttgggctgg cctaataa                 13128
```

<210> SEQ ID NO 2
<211> LENGTH: 4373
<212> TYPE: PRT
<213> ORGANISM: homo sapiens

<400> SEQUENCE: 2

Met Lys Val Asp Arg Thr Lys Leu Lys Lys Thr Pro Thr Glu Ala Pro
1               5                   10                  15

Ala Asp Cys Arg Ala Leu Ile Asp Lys Leu Lys Val Cys Asn Asp Glu
            20                  25                  30

Gln Leu Leu Leu Glu Leu Gln Gln Ile Lys Thr Trp Asn Ile Gly Lys
        35                  40                  45

```
Cys Glu Leu Tyr His Trp Val Asp Leu Asp Arg Phe Asp Gly Ile
 50                  55                  60

Leu Ala Asp Ala Gly Gln Thr Val Glu Asn Met Ser Trp Met Leu Val
 65                  70                  75                  80

Cys Asp Arg Pro Glu Arg Glu Gln Leu Lys Met Leu Leu Leu Ala Val
                 85                  90                  95

Leu Asn Phe Thr Ala Leu Leu Ile Glu Tyr Ser Phe Ser Arg His Leu
            100                 105                 110

Tyr Ser Ser Ile Glu His Leu Thr Thr Leu Leu Ala Ser Ser Asp Met
        115                 120                 125

Gln Val Val Leu Ala Val Leu Asn Leu Leu Tyr Val Phe Ser Lys Arg
130                 135                 140

Ser Asn Tyr Ile Thr Arg Leu Gly Ser Asp Lys Arg Thr Pro Leu Leu
145                 150                 155                 160

Thr Arg Leu Gln His Leu Ala Glu Ser Trp Gly Gly Lys Glu Asn Gly
                165                 170                 175

Phe Gly Leu Ala Glu Cys Cys Arg Asp Leu His Met Met Lys Tyr Pro
            180                 185                 190

Pro Ser Ala Thr Thr Leu His Phe Glu Phe Tyr Ala Asp Pro Gly Ala
        195                 200                 205

Glu Val Lys Ile Glu Lys Arg Thr Thr Ser Asn Thr Leu His Tyr Ile
210                 215                 220

His Ile Glu Gln Leu Asp Lys Ile Ser Glu Ser Pro Ser Glu Ile Met
225                 230                 235                 240

Glu Ser Leu Thr Lys Met Tyr Ser Ile Pro Lys Asp Lys Gln Met Leu
                245                 250                 255

Leu Phe Thr His Ile Arg Leu Ala His Gly Phe Ser Asn His Arg Lys
            260                 265                 270

Arg Leu Gln Ala Val Gln Ala Arg Leu His Ala Ile Ser Ile Leu Val
        275                 280                 285

Tyr Ser Asn Ala Leu Gln Glu Ser Ala Asn Ser Ile Leu Tyr Asn Gly
290                 295                 300

Leu Ile Glu Glu Leu Val Asp Val Leu Gln Ile Thr Asp Lys Gln Leu
305                 310                 315                 320

Met Glu Ile Lys Ala Ala Ser Leu Arg Thr Leu Thr Ser Ile Val His
                325                 330                 335

Leu Glu Arg Thr Pro Lys Leu Ser Ser Ile Ile Asp Cys Thr Gly Thr
            340                 345                 350

Ala Ser Tyr His Gly Phe Leu Pro Val Leu Val Arg Asn Cys Ile Gln
        355                 360                 365

Ala Met Ile Asp Pro Ser Met Asp Pro Tyr Pro His Gln Phe Ala Thr
370                 375                 380

Ala Leu Phe Ser Phe Leu Tyr His Leu Ala Ser Tyr Asp Ala Gly Gly
385                 390                 395                 400

Glu Ala Leu Val Ser Cys Gly Met Met Glu Ala Leu Leu Lys Val Ile
                405                 410                 415

Lys Phe Leu Gly Asp Glu Gln Asp Gln Ile Thr Phe Val Thr Arg Ala
            420                 425                 430

Val Arg Val Val Asp Leu Ile Thr Asn Leu Asp Met Ala Ala Phe Gln
        435                 440                 445

Ser His Ser Gly Leu Ser Ile Phe Ile Tyr Arg Leu Glu His Glu Val
450                 455                 460
```

-continued

```
Asp Leu Cys Arg Lys Glu Cys Pro Phe Val Ile Lys Pro Lys Ile Gln
465                 470                 475                 480

Arg Pro Asn Thr Thr Gln Glu Gly Glu Met Glu Thr Asp Met Asp
                485                 490                 495

Gly Val Gln Cys Ile Pro Gln Arg Ala Ala Leu Leu Lys Ser Met Leu
                500                 505                 510

Asn Phe Leu Lys Lys Ala Ile Gln Asp Pro Ala Phe Ser Asp Gly Ile
                515                 520                 525

Arg His Val Met Asp Gly Ser Leu Pro Thr Ser Leu Lys His Ile Ile
                530                 535                 540

Ser Asn Ala Glu Tyr Tyr Gly Pro Ser Leu Phe Leu Ala Thr Glu
545                 550                 555                 560

Val Val Thr Val Phe Val Phe Gln Glu Pro Ser Leu Leu Ser Ser Leu
                565                 570                 575

Gln Asp Asn Gly Leu Thr Asp Val Met Leu His Ala Leu Leu Ile Lys
                580                 585                 590

Asp Val Pro Ala Thr Arg Glu Val Leu Gly Ser Leu Pro Asn Val Phe
                595                 600                 605

Ser Ala Leu Cys Leu Asn Ala Arg Gly Leu Gln Ser Phe Val Gln Cys
                610                 615                 620

Gln Pro Phe Glu Arg Leu Phe Lys Val Leu Leu Ser Pro Asp Tyr Leu
625                 630                 635                 640

Pro Ala Met Arg Arg Arg Ser Ser Asp Pro Leu Gly Asp Thr Ala
                645                 650                 655

Ser Asn Leu Gly Ser Ala Val Asp Glu Leu Met Arg His Gln Pro Thr
                660                 665                 670

Leu Lys Thr Asp Ala Thr Thr Ala Ile Ile Lys Leu Leu Glu Glu Ile
                675                 680                 685

Cys Asn Leu Gly Arg Asp Pro Lys Tyr Ile Cys Gln Lys Pro Ser Ile
                690                 695                 700

Gln Lys Ala Asp Gly Thr Ala Thr Ala Pro Pro Arg Ser Asn His
705                 710                 715                 720

Ala Ala Glu Glu Ala Ser Ser Glu Asp Glu Glu Glu Glu Val Gln
                725                 730                 735

Ala Met Gln Ser Phe Asn Ser Thr Gln Gln Asn Glu Thr Glu Pro Asn
                740                 745                 750

Gln Gln Val Val Gly Thr Glu Glu Arg Ile Pro Ile Pro Leu Met Asp
                755                 760                 765

Tyr Ile Leu Asn Val Met Lys Phe Val Glu Ser Ile Leu Ser Asn Asn
                770                 775                 780

Thr Thr Asp Asp His Cys Gln Glu Phe Val Asn Gln Lys Gly Leu Leu
785                 790                 795                 800

Pro Leu Val Thr Ile Leu Gly Leu Pro Asn Leu Pro Ile Asp Phe Pro
                805                 810                 815

Thr Ser Ala Ala Cys Gln Ala Val Ala Gly Val Cys Lys Ser Ile Leu
                820                 825                 830

Thr Leu Ser His Glu Pro Lys Val Leu Gln Glu Gly Leu Leu Gln Leu
                835                 840                 845

Asp Ser Ile Leu Ser Ser Leu Glu Pro Leu His Arg Pro Ile Glu Ser
850                 855                 860

Pro Gly Gly Ser Val Leu Leu Arg Glu Leu Ala Cys Ala Gly Asn Val
865                 870                 875                 880

Ala Asp Ala Thr Leu Ser Ala Gln Ala Thr Pro Leu Leu His Ala Leu
```

-continued

```
                885                 890                 895
Thr Ala Ala His Ala Tyr Ile Met Met Phe Val His Thr Cys Arg Val
            900                 905                 910
Gly Gln Ser Glu Ile Arg Ser Ile Ser Val Asn Gln Trp Gly Ser Gln
            915                 920                 925
Leu Gly Leu Ser Val Leu Ser Lys Leu Ser Gln Leu Tyr Cys Ser Leu
            930                 935                 940
Val Trp Glu Ser Thr Val Leu Leu Ser Leu Cys Thr Pro Asn Ser Leu
945                 950                 955                 960
Pro Ser Gly Cys Glu Phe Gly Gln Ala Asp Met Gln Lys Leu Val Pro
            965                 970                 975
Lys Asp Glu Lys Ala Gly Thr Thr Gln Gly Gly Lys Arg Ser Asp Gly
            980                 985                 990
Glu Gln Asp Gly Ala Ala Gly Ser Met Asp Ala Ser Thr Gln Gly Leu
            995                1000                1005
Leu Glu Gly Ile Gly Leu Asp Gly Asp Thr Leu Ala Pro Met Glu
        1010                1015                1020
Thr Asp Glu Pro Thr Ala Ser Asp Ser Lys Gly Lys Ser Lys Ile
        1025                1030                1035
Thr Pro Ala Met Ala Ala Arg Ile Lys Gln Ile Lys Pro Leu Leu
        1040                1045                1050
Ser Ala Ser Ser Arg Leu Gly Arg Ala Leu Ala Glu Leu Phe Gly
        1055                1060                1065
Leu Leu Val Lys Leu Cys Val Gly Ser Pro Val Arg Gln Arg Arg
        1070                1075                1080
Ser His His Ala Ala Ser Thr Thr Thr Ala Pro Thr Pro Ala Ala
        1085                1090                1095
Arg Ser Thr Ala Ser Ala Leu Thr Lys Leu Leu Thr Lys Gly Leu
        1100                1105                1110
Ser Trp Gln Pro Pro Tyr Thr Pro Thr Leu Arg Phe Arg Leu
        1115                1120                1125
Thr Phe Phe Ile Cys Ser Val Gly Phe Thr Ser Pro Met Leu Phe
        1130                1135                1140
Asp Glu Arg Lys Tyr Pro Tyr His Leu Met Leu Gln Lys Phe Leu
        1145                1150                1155
Cys Ser Gly Gly His Asn Ala Leu Phe Glu Thr Phe Asn Trp Ala
        1160                1165                1170
Leu Ser Met Gly Gly Lys Val Pro Val Ser Glu Gly Leu Glu His
        1175                1180                1185
Ser Asp Leu Pro Asp Gly Thr Gly Glu Phe Leu Asp Ala Trp Leu
        1190                1195                1200
Met Leu Val Glu Lys Met Val Asn Pro Thr Thr Val Leu Glu Ser
        1205                1210                1215
Pro His Ser Leu Pro Ala Lys Leu Pro Gly Gly Val Gln Asn Phe
        1220                1225                1230
Pro Gln Phe Ser Ala Leu Arg Phe Leu Val Val Thr Gln Lys Ala
        1235                1240                1245
Ala Phe Thr Cys Ile Lys Asn Leu Trp Asn Arg Lys Pro Leu Lys
        1250                1255                1260
Val Tyr Gly Gly Arg Met Ala Glu Ser Met Leu Ala Ile Leu Cys
        1265                1270                1275
His Ile Leu Arg Gly Glu Pro Val Ile Arg Glu Arg Leu Ser Lys
        1280                1285                1290
```

-continued

```
Glu Lys Glu Gly Ser Arg Gly Glu Glu Asp Thr Gly Gln Glu Glu
    1295                1300                1305

Gly Gly Ser Arg Arg Glu Pro Gln Val Asn Gln Gln Gln Leu Gln
    1310                1315                1320

Gln Leu Met Asp Met Gly Phe Thr Arg Glu His Ala Met Glu Ala
    1325                1330                1335

Leu Leu Asn Thr Ser Thr Met Glu Gln Ala Thr Glu Tyr Leu Leu
    1340                1345                1350

Thr His Pro Pro Pro Ile Met Gly Gly Val Val Arg Asp Leu Ser
    1355                1360                1365

Met Ser Glu Glu Asp Gln Met Met Arg Ala Ile Ala Met Ser Leu
    1370                1375                1380

Gly Gln Asp Ile Pro Met Asp Gln Arg Ala Glu Ser Pro Glu Glu
    1385                1390                1395

Val Ala Cys Arg Lys Glu Glu Glu Arg Lys Ala Arg Glu Lys
    1400                1405                1410

Gln Glu Glu Glu Glu Ala Lys Cys Leu Glu Lys Phe Gln Asp Ala
    1415                1420                1425

Asp Pro Leu Glu Gln Asp Glu Leu His Thr Phe Thr Asp Thr Met
    1430                1435                1440

Leu Pro Gly Cys Phe His Leu Leu Asp Glu Leu Pro Asp Thr Val
    1445                1450                1455

Tyr Arg Val Cys Asp Leu Ile Met Thr Ala Ile Lys Arg Asn Gly
    1460                1465                1470

Ala Asp Tyr Arg Asp Met Ile Leu Lys Gln Val Val Asn Gln Val
    1475                1480                1485

Trp Glu Ala Ala Asp Val Leu Ile Lys Ala Ala Leu Pro Leu Thr
    1490                1495                1500

Thr Ser Asp Thr Lys Thr Val Ser Glu Trp Ile Ser Gln Met Ala
    1505                1510                1515

Thr Leu Pro Gln Ala Ser Asn Leu Ala Thr Arg Ile Leu Leu Leu
    1520                1525                1530

Thr Leu Leu Phe Glu Glu Leu Lys Leu Pro Cys Ala Trp Val Val
    1535                1540                1545

Glu Ser Ser Gly Ile Leu Asn Val Leu Ile Lys Leu Leu Glu Val
    1550                1555                1560

Val Gln Pro Cys Leu Gln Ala Ala Lys Glu Gln Lys Glu Val Gln
    1565                1570                1575

Thr Pro Lys Trp Ile Thr Pro Val Leu Leu Leu Ile Asp Phe Tyr
    1580                1585                1590

Glu Lys Thr Ala Ile Ser Ser Lys Arg Arg Ala Gln Met Thr Lys
    1595                1600                1605

Tyr Leu Gln Ser Asn Ser Asn Asn Trp Arg Trp Phe Asp Asp Arg
    1610                1615                1620

Ser Gly Arg Trp Cys Ser Tyr Ser Ala Ser Asn Ser Thr Ile
    1625                1630                1635

Asp Ser Ala Trp Lys Ser Gly Glu Thr Ser Val Arg Phe Thr Ala
    1640                1645                1650

Gly Arg Arg Arg Tyr Thr Val Gln Phe Thr Thr Met Val Gln Val
    1655                1660                1665

Asn Glu Glu Thr Gly Asn Arg Arg Pro Val Met Leu Thr Leu Leu
    1670                1675                1680
```

```
Arg Val Pro Arg Leu Asn Lys Asn Ser Lys Asn Ser Asn Gly Gln
1685                1690                1695

Glu Leu Glu Lys Thr Leu Glu Glu Ser Lys Glu Met Asp Ile Lys
1700                1705                1710

Arg Lys Glu Asn Lys Gly Asn Asp Thr Pro Leu Ala Leu Glu Ser
1715                1720                1725

Thr Asn Thr Glu Lys Glu Thr Ser Leu Glu Glu Thr Lys Ile Gly
1730                1735                1740

Glu Ile Leu Ile Gln Gly Leu Thr Glu Asp Met Val Thr Val Leu
1745                1750                1755

Ile Arg Ala Cys Val Ser Met Leu Gly Val Pro Val Asp Pro Asp
1760                1765                1770

Thr Leu His Ala Thr Leu Arg Leu Cys Leu Arg Leu Thr Arg Asp
1775                1780                1785

His Lys Tyr Ala Met Met Phe Ala Glu Leu Lys Ser Thr Arg Met
1790                1795                1800

Ile Leu Asn Leu Thr Gln Ser Ser Gly Phe Asn Gly Phe Thr Pro
1805                1810                1815

Leu Val Thr Leu Leu Leu Arg His Ile Ile Glu Asp Pro Cys Thr
1820                1825                1830

Leu Arg His Thr Met Glu Lys Val Val Arg Ser Ala Ala Thr Ser
1835                1840                1845

Gly Ala Gly Ser Thr Thr Ser Gly Val Val Ser Gly Ser Leu Gly
1850                1855                1860

Ser Arg Glu Ile Asn Tyr Ile Leu Arg Val Leu Gly Pro Ala Ala
1865                1870                1875

Cys Arg Asn Pro Asp Ile Phe Thr Glu Val Ala Asn Cys Cys Ile
1880                1885                1890

Arg Ile Ala Leu Pro Ala Pro Arg Gly Ser Gly Thr Ala Ser Asp
1895                1900                1905

Asp Glu Phe Glu Asn Leu Arg Ile Lys Gly Pro Asn Ala Val Gln
1910                1915                1920

Leu Val Lys Thr Thr Pro Leu Lys Pro Ser Pro Leu Pro Val Ile
1925                1930                1935

Pro Asp Thr Ile Lys Glu Val Ile Tyr Asp Met Leu Asn Ala Leu
1940                1945                1950

Ala Ala Tyr His Ala Pro Glu Glu Ala Asp Lys Ser Asp Pro Lys
1955                1960                1965

Pro Gly Val Met Thr Gln Glu Val Gly Gln Leu Leu Gln Asp Met
1970                1975                1980

Gly Asp Asp Val Tyr Gln Gln Tyr Arg Ser Leu Thr Arg Gln Ser
1985                1990                1995

Ser Asp Phe Asp Thr Gln Ser Gly Phe Ser Ile Asn Ser Gln Val
2000                2005                2010

Phe Ala Ala Asp Gly Ala Ser Thr Glu Thr Ser Ala Ser Gly Thr
2015                2020                2025

Ser Gln Gly Glu Ala Ser Thr Pro Glu Glu Ser Arg Asp Gly Lys
2030                2035                2040

Lys Asp Lys Glu Gly Asp Arg Ala Ser Glu Glu Gly Lys Gln Lys
2045                2050                2055

Gly Lys Gly Ser Lys Pro Leu Met Pro Thr Ser Thr Ile Leu Arg
2060                2065                2070

Leu Leu Ala Glu Leu Val Arg Ser Tyr Val Gly Ile Ala Thr Leu
```

-continued

```
         2075                2080                2085
Ile Ala  Asn Tyr Ser Tyr Thr Val Gly Gln Ser Glu  Leu Ile Lys
         2090                2095                2100

Glu Asp  Cys Ser Val Leu Ala Phe Val Leu Asp His  Leu Leu Pro
         2105                2110                2115

His Thr  Gln Asn Ala Glu Asp Lys Asp Thr Pro Ala  Leu Ala Arg
         2120                2125                2130

Leu Phe  Leu Ala Ser Leu Ala Ala Ala Gly Ser Gly  Thr Asp Ala
         2135                2140                2145

Gln Val  Ala Leu Val Asn Glu Val Lys Ala Ala Leu  Gly Arg Ala
         2150                2155                2160

Leu Ala  Met Ala Glu Ser Thr Glu Lys His Ala Arg  Leu Gln Ala
         2165                2170                2175

Val Met  Cys Ile Ile Ser Thr Ile Met Glu Ser Cys  Pro Ser Thr
         2180                2185                2190

Ser Ser  Phe Tyr Ser Ser Ala Thr Ala Lys Thr Gln  His Asn Gly
         2195                2200                2205

Met Asn  Asn Ile Ile Arg Leu Phe Leu Lys Lys Gly  Leu Val Asn
         2210                2215                2220

Asp Leu  Ala Arg Val Pro His Ser Leu Asp Leu Ser  Ser Pro Asn
         2225                2230                2235

Met Ala  Asn Thr Val Asn Ala Ala Leu Lys Pro Leu  Glu Thr Leu
         2240                2245                2250

Ser Arg  Ile Val Asn Gln Pro Ser Ser Leu Phe Gly  Ser Lys Ser
         2255                2260                2265

Ala Ser  Ser Lys Asn Lys Ser Glu Gln Asp Ala Gln  Gly Ala Ser
         2270                2275                2280

Gln Asp  Ser Ser Ser Asn Gln Gln Asp Pro Gly Glu  Pro Gly Glu
         2285                2290                2295

Ala Glu  Val Gln Glu Glu Asp His Asp Val Thr Gln  Thr Glu Val
         2300                2305                2310

Ala Asp  Gly Asp Ile Met Asp Gly Glu Ala Glu Thr  Asp Ser Val
         2315                2320                2325

Val Ile  Ala Gly Gln Pro Glu Val Leu Ser Ser Gln  Glu Met Gln
         2330                2335                2340

Val Glu  Asn Glu Leu Glu Asp Leu Ile Asp Glu Leu  Leu Glu Arg
         2345                2350                2355

Asp Gly  Gly Ser Gly Asn Ser Thr Ile Ile Val Ser  Arg Ser Gly
         2360                2365                2370

Glu Asp  Glu Ser Gln Glu Asp Val Leu Met Asp Glu  Ala Pro Ser
         2375                2380                2385

Asn Leu  Ser Gln Ala Ser Thr Leu Gln Ala Asn Arg  Glu Asp Ser
         2390                2395                2400

Met Asn  Ile Leu Asp Pro Glu Asp Glu Glu His Thr  Gln Glu
         2405                2410                2415

Glu Asp  Ser Ser Gly Ser Asn Glu Asp Glu Asp Ser  Gln Asp
         2420                2425                2430

Glu Glu  Glu Glu Glu Glu Glu Asp Glu Glu Asp Asp  Gln Glu Asp
         2435                2440                2445

Asp Glu  Gly Glu Glu Gly Asp Glu Asp Asp Asp Asp  Asp Gly Ser
         2450                2455                2460

Glu Met  Glu Leu Asp Glu Asp Tyr Pro Asp Met Asn  Ala Ser Pro
         2465                2470                2475
```

-continued

```
Leu Val Arg Phe Glu Arg Phe Asp Arg Glu Asp Leu Ile Ile
    2480            2485            2490

Glu Phe Asp Asn Met Phe Ser Ser Ala Thr Asp Ile Pro Pro Ser
    2495            2500            2505

Pro Gly Asn Ile Pro Thr Thr His Pro Leu Met Val Arg His Ala
    2510            2515            2520

Asp His Ser Ser Leu Thr Leu Gly Ser Gly Ser Ser Thr Thr Arg
    2525            2530            2535

Leu Thr Gln Gly Ile Gly Arg Ser Gln Arg Thr Leu Arg Gln Leu
    2540            2545            2550

Thr Ala Asn Thr Gly His Thr Ile His Val His Tyr Pro Gly Asn
    2555            2560            2565

Arg Gln Pro Asn Pro Pro Leu Ile Leu Gln Arg Leu Leu Gly Pro
    2570            2575            2580

Ser Ala Ala Asp Ile Leu Gln Leu Ser Ser Ser Leu Pro Leu
    2585            2590            2595

Gln Ser Arg Gly Arg Ala Arg Leu Leu Val Gly Asn Asp Asp Val
    2600            2605            2610

His Ile Ile Ala Arg Ser Asp Asp Glu Leu Leu Asp Asp Phe Phe
    2615            2620            2625

His Asp Gln Ser Thr Ala Thr Ser Gln Ala Gly Thr Leu Ser Ser
    2630            2635            2640

Ile Pro Thr Ala Leu Thr Arg Trp Thr Glu Glu Cys Lys Val Leu
    2645            2650            2655

Asp Ala Glu Ser Met His Asp Cys Val Ser Val Lys Val Ser
    2660            2665            2670

Ile Val Asn His Leu Glu Phe Leu Arg Asp Glu Glu Leu Glu Glu
    2675            2680            2685

Arg Arg Glu Lys Arg Arg Lys Gln Leu Ala Glu Glu Thr Lys
    2690            2695            2700

Ile Thr Asp Lys Gly Lys Glu Asp Lys Glu Asn Arg Asp Gln Ser
    2705            2710            2715

Ala Gln Cys Thr Ala Ser Lys Ser Asn Asp Ser Thr Glu Gln Asn
    2720            2725            2730

Leu Ser Asp Gly Thr Pro Met Pro Asp Ser Tyr Pro Thr Thr Pro
    2735            2740            2745

Ser Ser Thr Asp Ala Ala Thr Ser Glu Ser Lys Glu Thr Leu Gly
    2750            2755            2760

Thr Leu Gln Ser Ser Gln Gln Gln Pro Thr Leu Pro Thr Pro Pro
    2765            2770            2775

Ala Leu Gly Glu Val Pro Gln Glu Leu Gln Ser Pro Ala Gly Glu
    2780            2785            2790

Gly Gly Ser Ser Thr Gln Leu Leu Met Pro Val Glu Pro Glu Glu
    2795            2800            2805

Leu Gly Pro Thr Arg Pro Ser Gly Glu Ala Glu Thr Thr Gln Met
    2810            2815            2820

Glu Leu Ser Pro Ala Pro Thr Ile Thr Ser Leu Ser Pro Glu Arg
    2825            2830            2835

Ala Glu Asp Ser Asp Ala Leu Thr Ala Val Ser Ser Gln Leu Glu
    2840            2845            2850

Gly Ser Pro Met Asp Thr Ser Ser Leu Ala Ser Cys Thr Leu Glu
    2855            2860            2865
```

-continued

Glu Ala Val Gly Asp Thr Ser Ala Ala Gly Ser Ser Glu Gln Pro
2870                2875                2880

Arg Ala Gly Ser Ser Thr Pro Gly Asp Ala Pro Pro Ala Val Ala
2885                2890                2895

Glu Val Gln Gly Arg Ser Asp Gly Ser Gly Glu Ser Ala Gln Pro
2900                2905                2910

Pro Glu Asp Ser Ser Pro Pro Ala Ser Ser Glu Ser Ser Ser Thr
2915                2920                2925

Arg Asp Ser Ala Val Ala Ile Ser Gly Ala Asp Ser Arg Gly Ile
2930                2935                2940

Leu Glu Glu Pro Leu Pro Ser Thr Ser Ser Glu Glu Glu Asp Pro
2945                2950                2955

Leu Ala Gly Ile Ser Leu Pro Glu Gly Val Asp Pro Ser Phe Leu
2960                2965                2970

Ala Ala Leu Pro Asp Asp Ile Arg Arg Glu Val Leu Gln Asn Gln
2975                2980                2985

Leu Gly Ile Arg Pro Pro Thr Arg Thr Ala Pro Ser Thr Asn Ser
2990                2995                3000

Ser Ala Pro Ala Val Val Gly Asn Pro Gly Val Thr Glu Val Ser
3005                3010                3015

Pro Glu Phe Leu Ala Ala Leu Pro Pro Ala Ile Gln Glu Glu Val
3020                3025                3030

Leu Ala Gln Gln Arg Ala Glu Gln Gln Arg Arg Glu Leu Ala Gln
3035                3040                3045

Asn Ala Ser Ser Asp Thr Pro Met Asp Pro Val Thr Phe Ile Gln
3050                3055                3060

Thr Leu Pro Ser Asp Leu Arg Arg Ser Val Leu Glu Asp Met Glu
3065                3070                3075

Asp Ser Val Leu Ala Val Met Pro Pro Asp Ile Ala Ala Glu Ala
3080                3085                3090

Gln Ala Leu Arg Arg Glu Gln Glu Ala Arg Gln Arg Gln Leu Met
3095                3100                3105

His Glu Arg Leu Phe Gly His Ser Ser Thr Ser Ala Leu Ser Ala
3110                3115                3120

Ile Leu Arg Ser Pro Ala Phe Thr Ser Arg Leu Ser Gly Asn Arg
3125                3130                3135

Gly Val Gln Tyr Thr Arg Leu Ala Val Gln Arg Gly Gly Thr Phe
3140                3145                3150

Gln Met Gly Gly Ser Ser Ser His Asn Arg Pro Ser Gly Ser Asn
3155                3160                3165

Asp Thr Leu Leu Arg Leu Arg Gly Arg Leu Leu Leu Asp His Glu
3170                3175                3180

Ala Leu Ser Cys Leu Leu Val Leu Leu Phe Val Asp Glu Pro Lys
3185                3190                3195

Leu Asn Thr Ser Arg Leu His Arg Val Leu Arg Asn Leu Cys Tyr
3200                3205                3210

His Ala Gln Thr Arg His Trp Val Ile Arg Ser Leu Leu Ser Ile
3215                3220                3225

Leu Gln Arg Ser Ser Glu Ser Glu Leu Cys Ile Glu Thr Pro Lys
3230                3235                3240

Leu Thr Thr Ser Glu Glu Lys Gly Lys Lys Ser Ser Lys Ser Cys
3245                3250                3255

Gly Ser Ser Ser His Glu Asn Arg Pro Leu Asp Leu Leu His Lys

```
                3260            3265            3270
Met Glu Ser Lys Ser Ser Asn Gln Leu Ser Trp Leu Ser Val Ser
        3275            3280            3285
Met Asp Ala Ala Leu Gly Cys Arg Thr Asn Ile Phe Gln Ile Gln
        3290            3295            3300
Arg Ser Gly Gly Arg Lys His Thr Glu Lys His Ala Ser Gly Gly
        3305            3310            3315
Ser Thr Val His Ile His Pro Gln Ala Ala Pro Val Val Cys Arg
        3320            3325            3330
His Val Leu Asp Thr Leu Ile Gln Leu Ala Lys Val Phe Pro Ser
        3335            3340            3345
His Phe Thr Gln Gln Arg Thr Lys Glu Thr Asn Cys Glu Ser Asp
        3350            3355            3360
Arg Glu Arg Gly Asn Lys Ala Cys Ser Pro Cys Ser Ser Gln Ser
        3365            3370            3375
Ser Ser Ser Gly Ile Cys Thr Asp Phe Trp Asp Leu Leu Val Lys
        3380            3385            3390
Leu Asp Asn Met Asn Val Ser Arg Lys Gly Lys Asn Ser Val Lys
        3395            3400            3405
Ser Val Pro Val Ser Ala Gly Gly Glu Gly Glu Thr Ser Pro Tyr
        3410            3415            3420
Ser Leu Glu Ala Ser Pro Leu Gly Gln Leu Met Asn Met Leu Ser
        3425            3430            3435
His Pro Val Ile Arg Arg Ser Ser Leu Leu Thr Glu Lys Leu Leu
        3440            3445            3450
Arg Leu Leu Ser Leu Ile Ser Ile Ala Leu Pro Glu Asn Lys Val
        3455            3460            3465
Ser Glu Ala Gln Ala Asn Ser Gly Ser Gly Ala Ser Ser Thr Thr
        3470            3475            3480
Thr Ala Thr Ser Thr Thr Ser Thr Thr Thr Thr Ala Ala Ser
        3485            3490            3495
Thr Thr Pro Thr Pro Pro Thr Ala Pro Thr Pro Val Thr Ser Ala
        3500            3505            3510
Pro Ala Leu Val Ala Ala Thr Ala Ile Ser Thr Ile Val Val Ala
        3515            3520            3525
Ala Ser Thr Thr Val Thr Thr Pro Thr Thr Ala Thr Thr Thr Val
        3530            3535            3540
Ser Ile Ser Pro Thr Thr Lys Gly Ser Lys Ser Pro Ala Lys Val
        3545            3550            3555
Ser Asp Gly Gly Ser Ser Ser Thr Asp Phe Lys Met Val Ser Ser
        3560            3565            3570
Gly Leu Thr Glu Asn Gln Leu Gln Leu Ser Val Glu Val Leu Thr
        3575            3580            3585
Ser His Ser Cys Ser Glu Glu Gly Leu Glu Asp Ala Ala Asn Val
        3590            3595            3600
Leu Leu Gln Leu Ser Arg Gly Asp Ser Gly Thr Arg Asp Thr Val
        3605            3610            3615
Leu Lys Leu Leu Leu Asn Gly Ala Arg His Leu Gly Tyr Thr Leu
        3620            3625            3630
Cys Lys Gln Ile Gly Thr Leu Leu Ala Glu Leu Arg Glu Tyr Asn
        3635            3640            3645
Leu Glu Gln Gln Arg Arg Ala Gln Cys Glu Thr Leu Ser Pro Asp
        3650            3655            3660
```

-continued

```
Gly Leu Pro Glu Glu Gln Pro Gln Thr Thr Lys Leu Lys Gly Lys
    3665                3670                3675

Met Gln Ser Arg Phe Asp Met Ala Glu Asn Val Val Ile Val Ala
    3680                3685                3690

Ser Gln Lys Arg Pro Leu Gly Gly Arg Glu Leu Gln Leu Pro Ser
    3695                3700                3705

Met Ser Met Leu Thr Ser Lys Thr Ser Thr Gln Lys Phe Phe Leu
    3710                3715                3720

Arg Val Leu Gln Val Ile Ile Gln Leu Arg Asp Asp Thr Arg Arg
    3725                3730                3735

Ala Asn Lys Lys Ala Lys Gln Thr Gly Arg Leu Gly Ser Ser Gly
    3740                3745                3750

Leu Gly Ser Ala Ser Ser Ile Gln Ala Ala Val Arg Gln Leu Glu
    3755                3760                3765

Ala Glu Ala Asp Ala Ile Ile Gln Met Val Arg Glu Gly Gln Arg
    3770                3775                3780

Ala Arg Arg Gln Gln Gln Ala Ala Thr Ser Glu Ser Ser Gln Ser
    3785                3790                3795

Glu Ala Ser Val Arg Arg Glu Glu Ser Pro Met Asp Val Asp Gln
    3800                3805                3810

Pro Ser Pro Ser Ala Gln Asp Thr Gln Ser Ile Ala Ser Asp Gly
    3815                3820                3825

Thr Pro Gln Gly Glu Lys Glu Lys Glu Glu Arg Pro Pro Glu Leu
    3830                3835                3840

Pro Leu Leu Ser Glu Gln Leu Ser Leu Asp Glu Leu Trp Asp Met
    3845                3850                3855

Leu Gly Glu Cys Leu Lys Glu Leu Glu Glu Ser His Asp Gln His
    3860                3865                3870

Ala Val Leu Val Leu Gln Pro Ala Val Glu Ala Phe Phe Leu Val
    3875                3880                3885

His Ala Thr Glu Arg Glu Ser Lys Pro Pro Val Arg Asp Thr Arg
    3890                3895                3900

Glu Ser Gln Leu Ala His Ile Lys Asp Glu Pro Pro Pro Leu Ser
    3905                3910                3915

Pro Ala Pro Leu Thr Pro Ala Thr Pro Ser Ser Leu Asp Pro Phe
    3920                3925                3930

Phe Ser Arg Glu Pro Ser Ser Met His Ile Ser Ser Ser Leu Pro
    3935                3940                3945

Pro Asp Thr Gln Lys Phe Leu Arg Phe Ala Glu Thr His Arg Thr
    3950                3955                3960

Val Leu Asn Gln Ile Leu Arg Gln Ser Thr Thr His Leu Ala Asp
    3965                3970                3975

Gly Pro Phe Ala Val Leu Val Asp Tyr Ile Arg Val Leu Asp Phe
    3980                3985                3990

Asp Val Lys Arg Lys Tyr Phe Arg Gln Glu Leu Glu Arg Leu Asp
    3995                4000                4005

Glu Gly Leu Arg Lys Glu Asp Met Ala Val His Val Arg Arg Asp
    4010                4015                4020

His Val Phe Glu Asp Ser Tyr Arg Glu Leu His Arg Lys Ser Pro
    4025                4030                4035

Glu Glu Met Lys Asn Arg Leu Tyr Ile Val Phe Glu Gly Glu Glu
    4040                4045                4050
```

```
Gly Gln Asp Ala Gly Gly Leu Leu Arg Glu Trp Tyr Met Ile Ile
    4055                4060                4065
Ser Arg Glu Met Phe Asn Pro Met Tyr Ala Leu Phe Arg Thr Ser
    4070                4075                4080
Pro Gly Asp Arg Val Thr Tyr Thr Ile Asn Pro Ser Ser His Cys
    4085                4090                4095
Asn Pro Asn His Leu Ser Tyr Phe Lys Phe Val Gly Arg Ile Val
    4100                4105                4110
Ala Lys Ala Val Tyr Asp Asn Arg Leu Leu Glu Cys Tyr Phe Thr
    4115                4120                4125
Arg Ser Phe Tyr Lys His Ile Leu Gly Lys Ser Val Arg Tyr Thr
    4130                4135                4140
Asp Met Glu Ser Glu Asp Tyr His Phe Tyr Gln Gly Leu Val Tyr
    4145                4150                4155
Leu Leu Glu Asn Asp Val Ser Thr Leu Gly Tyr Asp Leu Thr Phe
    4160                4165                4170
Ser Thr Glu Val Gln Glu Phe Gly Val Cys Glu Val Arg Asp Leu
    4175                4180                4185
Lys Pro Asn Gly Ala Asn Ile Leu Val Thr Glu Glu Asn Lys Lys
    4190                4195                4200
Glu Tyr Val His Leu Val Cys Gln Met Arg Met Thr Gly Ala Ile
    4205                4210                4215
Arg Lys Gln Leu Ala Ala Phe Leu Glu Gly Phe Tyr Glu Ile Ile
    4220                4225                4230
Pro Lys Arg Leu Ile Ser Ile Phe Thr Glu Gln Glu Leu Glu Leu
    4235                4240                4245
Leu Ile Ser Gly Leu Pro Thr Ile Asp Ile Asp Asp Leu Lys Ser
    4250                4255                4260
Asn Thr Glu Tyr His Lys Tyr Gln Ser Asn Ser Ile Gln Ile Gln
    4265                4270                4275
Trp Phe Trp Arg Ala Leu Arg Ser Phe Asp Gln Ala Asp Arg Ala
    4280                4285                4290
Lys Phe Leu Gln Phe Val Thr Gly Thr Ser Lys Val Pro Leu Gln
    4295                4300                4305
Gly Phe Ala Ala Leu Glu Gly Met Asn Gly Ile Gln Lys Phe Gln
    4310                4315                4320
Ile His Arg Asp Asp Arg Ser Thr Asp Arg Leu Pro Ser Ala His
    4325                4330                4335
Thr Cys Phe Asn Gln Leu Asp Leu Pro Ala Tyr Glu Ser Phe Glu
    4340                4345                4350
Lys Leu Arg His Met Leu Leu Leu Ala Ile Gln Glu Cys Ser Glu
    4355                4360                4365
Gly Phe Gly Leu Ala
    4370

<210> SEQ ID NO 3
<211> LENGTH: 18
<212> TYPE: PRT
<213> ORGANISM: homo sapiens

<400> SEQUENCE: 3

Leu Tyr Ile Val Phe Glu Gly Glu Glu Gly Gln Asp Ala Gly Gly Leu
1               5                   10                  15

Leu Arg
```

<210> SEQ ID NO 4
<211> LENGTH: 15
<212> TYPE: PRT
<213> ORGANISM: homo sapiens

<400> SEQUENCE: 4

Leu Pro Gly Gly Val Gln Asn Phe Pro Gln Phe Ser Ala Leu Arg
1               5                   10                  15

<210> SEQ ID NO 5
<211> LENGTH: 14
<212> TYPE: PRT
<213> ORGANISM: homo sapiens

<400> SEQUENCE: 5

Met Thr Asp Gln Glu Ala Ile Gln Asp Leu Trp Gln Trp Arg
1               5                   10

<210> SEQ ID NO 6
<211> LENGTH: 13
<212> TYPE: PRT
<213> ORGANISM: homo sapiens

<400> SEQUENCE: 6

Val Asp Asn Asp Glu Asn Glu His Gln Leu Ser Leu Arg
1               5                   10

<210> SEQ ID NO 7
<211> LENGTH: 339
<212> TYPE: PRT
<213> ORGANISM: homo sapiens

<400> SEQUENCE: 7

Arg Lys Ser Pro Glu Glu Met Lys Asn Arg Leu Tyr Ile Val Phe Glu
1               5                   10                  15

Gly Glu Glu Gly Gln Asp Ala Gly Gly Leu Leu Arg Glu Trp Tyr Met
            20                  25                  30

Ile Ile Ser Arg Glu Met Phe Asn Pro Met Tyr Ala Leu Phe Arg Thr
        35                  40                  45

Ser Pro Gly Asp Arg Val Thr Tyr Thr Ile Asn Pro Ser Ser His Cys
    50                  55                  60

Asn Pro Asn His Leu Ser Tyr Phe Lys Phe Val Gly Arg Ile Val Ala
65                  70                  75                  80

Lys Ala Val Tyr Asp Asn Arg Leu Leu Glu Cys Tyr Phe Thr Arg Ser
                85                  90                  95

Phe Tyr Lys His Ile Leu Gly Lys Ser Val Arg Tyr Thr Asp Met Glu
            100                 105                 110

Ser Glu Asp Tyr His Phe Tyr Gln Gly Leu Val Tyr Leu Leu Glu Asn
        115                 120                 125

Asp Val Ser Thr Leu Gly Tyr Asp Leu Thr Phe Ser Thr Glu Val Gln
    130                 135                 140

Glu Phe Gly Val Cys Glu Val Arg Asp Leu Lys Pro Asn Gly Ala Asn
145                 150                 155                 160

Ile Leu Val Thr Glu Glu Asn Lys Lys Glu Tyr Val His Leu Val Cys
                165                 170                 175

Gln Met Arg Met Thr Gly Ala Ile Arg Lys Gln Leu Ala Ala Phe Leu
            180                 185                 190

Glu Gly Phe Tyr Glu Ile Ile Pro Lys Arg Leu Ile Ser Ile Phe Thr
        195                 200                 205

```
Glu Gln Glu Leu Glu Leu Leu Ile Ser Gly Leu Pro Thr Ile Asp Ile
    210                 215                 220

Asp Asp Leu Lys Ser Asn Thr Glu Tyr His Lys Tyr Gln Ser Asn Ser
225                 230                 235                 240

Ile Gln Ile Gln Trp Phe Trp Arg Ala Leu Arg Ser Phe Asp Gln Ala
                245                 250                 255

Asp Arg Ala Lys Phe Leu Gln Phe Val Thr Gly Thr Ser Lys Val Pro
            260                 265                 270

Leu Gln Gly Phe Ala Ala Leu Glu Gly Met Asn Gly Ile Gln Lys Phe
        275                 280                 285

Gln Ile His Arg Asp Asp Arg Ser Thr Asp Arg Leu Pro Ser Ala His
    290                 295                 300

Thr Cys Phe Asn Gln Leu Asp Leu Pro Ala Tyr Glu Ser Phe Glu Lys
305                 310                 315                 320

Leu Arg His Met Leu Leu Leu Ala Ile Gln Glu Cys Ser Glu Gly Phe
                325                 330                 335

Gly Leu Ala

<210> SEQ ID NO 8
<211> LENGTH: 339
<212> TYPE: PRT
<213> ORGANISM: mus musculus

<400> SEQUENCE: 8

Arg Lys Ser Pro Glu Glu Met Lys Asn Arg Leu Tyr Ile Val Phe Glu
1               5                   10                  15

Gly Glu Glu Gly Gln Asp Ala Gly Gly Leu Leu Arg Glu Trp Tyr Met
            20                  25                  30

Ile Ile Ser Arg Glu Met Phe Asn Pro Met Tyr Ala Leu Phe Arg Thr
        35                  40                  45

Ser Pro Gly Asp Arg Val Thr Tyr Thr Ile Asn Pro Ser Ser His Cys
    50                  55                  60

Asn Pro Asn His Leu Ser Tyr Phe Lys Phe Val Gly Arg Ile Val Ala
65                  70                  75                  80

Lys Ala Val Tyr Asp Asn Arg Leu Leu Glu Cys Tyr Phe Thr Arg Ser
                85                  90                  95

Phe Tyr Lys His Ile Leu Gly Lys Ser Val Arg Tyr Thr Asp Met Glu
            100                 105                 110

Ser Glu Asp Tyr His Phe Tyr Gln Gly Leu Val Tyr Leu Leu Glu Asn
        115                 120                 125

Asp Val Ser Thr Leu Gly Tyr Asp Leu Thr Phe Ser Thr Glu Val Gln
    130                 135                 140

Glu Phe Gly Val Cys Glu Val Arg Asp Leu Lys Pro Asn Gly Ala Asn
145                 150                 155                 160

Ile Leu Val Thr Glu Glu Asn Lys Lys Glu Tyr Val His Leu Val Cys
                165                 170                 175

Gln Met Arg Met Thr Gly Ala Ile Arg Lys Gln Leu Ala Ala Phe Leu
            180                 185                 190

Glu Gly Phe Tyr Glu Ile Ile Pro Lys Arg Leu Ile Ser Ile Phe Thr
        195                 200                 205

Glu Gln Glu Leu Glu Leu Leu Ile Ser Gly Leu Pro Thr Ile Asp Ile
    210                 215                 220

Asp Asp Leu Lys Ser Asn Thr Glu Tyr His Lys Tyr Gln Ser Asn Ser
225                 230                 235                 240
```

```
Ile Gln Ile Gln Trp Phe Trp Arg Ala Leu Arg Ser Phe Asp Gln Ala
            245                 250                 255

Asp Arg Ala Lys Phe Leu Gln Phe Val Thr Gly Thr Ser Lys Val Pro
        260                 265                 270

Leu Gln Gly Phe Ala Ala Leu Glu Gly Met Asn Gly Ile Gln Lys Phe
        275                 280                 285

Gln Ile His Arg Asp Asp Arg Ser Thr Asp Arg Leu Pro Ser Ala His
    290                 295                 300

Thr Cys Phe Asn Gln Leu Asp Leu Pro Ala Tyr Glu Ser Phe Glu Lys
305                 310                 315                 320

Leu Arg His Met Leu Leu Ala Ile Gln Glu Cys Ser Glu Gly Phe
                325                 330                 335

Gly Leu Ala

<210> SEQ ID NO 9
<211> LENGTH: 331
<212> TYPE: PRT
<213> ORGANISM: homo sapiens

<400> SEQUENCE: 9

Met Glu Asn Pro Ala Asp Leu Lys Lys Gln Leu Tyr Val Glu Phe Glu
1               5                   10                  15

Gly Glu Gln Gly Val Asp Glu Gly Gly Val Ser Lys Glu Phe Phe Gln
            20                  25                  30

Leu Val Val Glu Glu Ile Phe Asn Pro Asp Ile Gly Met Phe Thr Tyr
        35                  40                  45

Asp Glu Ser Thr Lys Leu Phe Trp Phe Asn Pro Ser Ser Phe Glu Thr
    50                  55                  60

Glu Gly Gln Phe Thr Leu Ile Gly Ile Val Leu Gly Leu Ala Ile Tyr
65                  70                  75                  80

Asn Asn Cys Ile Leu Asp Val His Phe Pro Met Val Val Tyr Arg Lys
                85                  90                  95

Leu Met Gly Lys Lys Gly Thr Phe Arg Asp Leu Gly Asp Ser His Pro
            100                 105                 110

Val Leu Tyr Gln Ser Leu Lys Asp Leu Leu Glu Tyr Glu Gly Asn Val
        115                 120                 125

Glu Asp Asp Met Met Ile Thr Phe Gln Ile Ser Gln Thr Asp Leu Phe
    130                 135                 140

Gly Asn Pro Met Met Tyr Asp Leu Lys Glu Asn Gly Asp Lys Ile Pro
145                 150                 155                 160

Ile Thr Asn Glu Asn Arg Lys Glu Phe Val Asn Leu Tyr Ser Asp Tyr
                165                 170                 175

Ile Leu Asn Lys Ser Val Glu Lys Gln Phe Lys Ala Phe Arg Arg Gly
            180                 185                 190

Phe His Met Val Thr Asn Glu Ser Pro Leu Lys Tyr Leu Phe Arg Pro
        195                 200                 205

Glu Glu Ile Glu Leu Leu Ile Cys Gly Ser Arg Asn Leu Asp Phe Gln
    210                 215                 220

Ala Leu Glu Glu Thr Thr Glu Tyr Asp Gly Gly Tyr Thr Arg Asp Ser
225                 230                 235                 240

Val Leu Ile Arg Glu Phe Trp Glu Ile Val His Ser Phe Thr Asp Glu
                245                 250                 255

Gln Lys Arg Leu Phe Leu Gln Phe Thr Thr Gly Thr Asp Arg Ala Pro
            260                 265                 270
```

```
Val Gly Gly Leu Gly Lys Leu Lys Met Ile Ile Ala Lys Asn Gly Pro
            275                 280                 285

Asp Thr Glu Arg Leu Pro Thr Ser His Thr Cys Phe Asn Val Leu Leu
        290                 295                 300

Leu Pro Glu Tyr Ser Ser Lys Glu Lys Leu Lys Glu Arg Leu Leu Lys
305                 310                 315                 320

Ala Ile Thr Tyr Ala Lys Gly Phe Gly Met Leu
                325                 330

<210> SEQ ID NO 10
<211> LENGTH: 37
<212> TYPE: PRT
<213> ORGANISM: homo sapiens

<400> SEQUENCE: 10

Asn Gln Gln Gln Leu Gln Gln Leu Met Asp Met Gly Phe Thr Arg Glu
1               5                   10                  15

His Ala Met Glu Ala Leu Leu Asn Thr Ser Thr Met Glu Gln Ala Thr
            20                  25                  30

Glu Tyr Leu Leu Thr
        35

<210> SEQ ID NO 11
<211> LENGTH: 37
<212> TYPE: PRT
<213> ORGANISM: mus musculus

<400> SEQUENCE: 11

Asn Gln Gln Gln Leu Gln Gln Leu Met Asp Met Gly Phe Thr Arg Glu
1               5                   10                  15

His Ala Met Glu Ala Leu Leu Asn Thr Ser Thr Met Glu Gln Ala Thr
            20                  25                  30

Glu Tyr Leu Leu Thr
        35

<210> SEQ ID NO 12
<211> LENGTH: 38
<212> TYPE: PRT
<213> ORGANISM: saccharomyces cerevisiae

<400> SEQUENCE: 12

Leu Ser Ser Glu Ile Glu Asn Leu Met Ser Gln Gly Tyr Ser Tyr Gln
1               5                   10                  15

Asp Ile Gln Lys Ala Leu Val Ile Ala Gln Asn Asn Ile Glu Met Ala
            20                  25                  30

Lys Asn Ile Leu Arg Glu
        35

<210> SEQ ID NO 13
<211> LENGTH: 38
<212> TYPE: PRT
<213> ORGANISM: homo sapiens
<220> FEATURE:
<221> NAME/KEY: MOD_RES
<222> LOCATION: (4)..(4)
<223> OTHER INFORMATION: Variable amino acid

<400> SEQUENCE: 13

Glu Glu Thr Xaa Leu Thr Glu Ile Met Ser Met Gly Tyr Glu Arg Glu
1               5                   10                  15
```

Arg Val Val Ala Ala Leu Arg Ala Ser Tyr Asn Asn Pro His Arg Ala
            20                  25                  30

Val Glu Tyr Leu Leu Thr
        35

<210> SEQ ID NO 14
<211> LENGTH: 38
<212> TYPE: PRT
<213> ORGANISM: homo sapiens

<400> SEQUENCE: 14

Arg Asn Glu Thr Ile Glu Arg Ile Met Glu Met Gly Tyr Gln Arg Glu
1               5                   10                  15

Glu Val Glu Arg Ala Leu Arg Ala Ala Phe Asn Asn Pro Asp Arg Ala
            20                  25                  30

Val Glu Tyr Leu Leu Met
        35

<210> SEQ ID NO 15
<211> LENGTH: 38
<212> TYPE: PRT
<213> ORGANISM: homo sapiens

<400> SEQUENCE: 15

Val Asp Ala Lys Ile Ala Lys Leu Met Gly Glu Gly Tyr Ala Phe Glu
1               5                   10                  15

Glu Val Lys Arg Ala Leu Glu Ile Ala Gln Asn Asn Val Glu Val Ala
            20                  25                  30

Arg Ser Ile Leu Glu Glu
        35

<210> SEQ ID NO 16
<211> LENGTH: 16
<212> TYPE: DNA
<213> ORGANISM: homo sapiens

<400> SEQUENCE: 16
aattgctatg tctctg                                                         16

<210> SEQ ID NO 17
<211> LENGTH: 15
<212> TYPE: DNA
<213> ORGANISM: Artificial
<220> FEATURE:
<223> OTHER INFORMATION: Description of Artificial Sequence: Synthetic
      nucleotide sequence

<400> SEQUENCE: 17
aattgatatc ctctg                                                          15

<210> SEQ ID NO 18
<211> LENGTH: 21
<212> TYPE: RNA
<213> ORGANISM: Artificial
<220> FEATURE:
<223> OTHER INFORMATION: Description of Artificial Sequence: Synthetic
      nucleotide sequence

<400> SEQUENCE: 18
aauugcuaug ucucugggac a                                                   21

<210> SEQ ID NO 19
<211> LENGTH: 21

```
<212> TYPE: RNA
<213> ORGANISM: Artificial
<220> FEATURE:
<223> OTHER INFORMATION: Description of Artificial Sequence: Synthetic
      nucleotide sequence

<400> SEQUENCE: 19
aaguaucccu accaccucau g                                          21

<210> SEQ ID NO 20
<211> LENGTH: 21
<212> TYPE: RNA
<213> ORGANISM: Artificial
<220> FEATURE:
<223> OTHER INFORMATION: Description of Artificial Sequence: Synthetic
      nucleotide sequence

<400> SEQUENCE: 20
aauugccaug uaucugggac a                                          21

<210> SEQ ID NO 21
<211> LENGTH: 21
<212> TYPE: RNA
<213> ORGANISM: Artificial
<220> FEATURE:
<223> OTHER INFORMATION: Description of Artificial Sequence: Synthetic
      nucleotide sequence

<400> SEQUENCE: 21
aagaggacuc cgcuacugac a                                          21

<210> SEQ ID NO 22
<211> LENGTH: 21
<212> TYPE: RNA
<213> ORGANISM: Artificial
<220> FEATURE:
<223> OTHER INFORMATION: Description of Artificial Sequence: Synthetic
      nucleotide sequence

<400> SEQUENCE: 22 aagguggag ugaucaaaag g                                           21
```